(12) United States Patent
Hatakeyama et al.

(10) Patent No.: US 11,801,333 B2
(45) Date of Patent: Oct. 31, 2023

(54) BIO-ELECTRODE COMPOSITION, BIO-ELECTRODE, AND METHOD FOR MANUFACTURING A BIO-ELECTRODE

(71) Applicant: SHIN-ETSU CHEMICAL CO., LTD., Tokyo (JP)

(72) Inventors: Jun Hatakeyama, Joetsu (JP); Osamu Watanabe, Joetsu (JP); Koji Hasegawa, Joetsu (JP); Motoaki Iwabuchi, Joetsu (JP); Yasuyoshi Kuroda, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 1120 days.

(21) Appl. No.: 16/351,027

(22) Filed: Mar. 12, 2019

(65) Prior Publication Data

US 2019/0298891 A1 Oct. 3, 2019

(30) Foreign Application Priority Data

Apr. 2, 2018 (JP) .................................. 2018-70818

(51) Int. Cl.
*A61L 31/10* (2006.01)
*C08K 3/04* (2006.01)
(Continued)

(52) U.S. Cl.
CPC ................ *A61L 31/10* (2013.01); *A61B 5/25* (2021.01); *A61L 31/14* (2013.01); *C08K 3/04* (2013.01);
(Continued)

(58) Field of Classification Search
None
See application file for complete search history.

(56) References Cited

U.S. PATENT DOCUMENTS 5,981,680 A 11/1999 Petroff et al.
6,096,453 A * 8/2000 Grunwald ......... H01M 10/0565
429/212

(Continued)

FOREIGN PATENT DOCUMENTS

JP H05-095924 A 4/1993
JP 2002-332305 A 11/2002
(Continued)

OTHER PUBLICATIONS

Long, Lizhen et al., "Polymer Electrolytes for Lithium Polymer Batteries", Journal of Materials Chemistry A, vol. 4, pp. 10038-10069, (2016).

(Continued)

*Primary Examiner* — Tae H Yoon
(74) *Attorney, Agent, or Firm* — Oliff PLC

(57) ABSTRACT

The present invention provides a bio-electrode composition including: (A) an ionic material; and (B) a resin other than the component (A); wherein the component (A) contains both of a repeating unit-a having a structure of any of silver salts of fluorosulfonic acid, fluorosulfonimide, and fluorosulfonamide; and a repeating unit-b having silicon. This can form a living body contact layer for a bio-electrode that is excellent in electric conductivity and biocompatibility, light in weight, manufacturable at low cost, and free from large lowering of the electric conductivity even when it is wetted with water or dried. The present invention also provides a bio-electrode in which the living body contact layer is formed from the bio-electrode composition, and a method for manufacturing the bio-electrode.

20 Claims, 2 Drawing Sheets

(51) Int. Cl.

| | | |
|---|---|---|
| *C08K 9/02* | (2006.01) | |
| *C08K 3/11* | (2018.01) | |
| *A61L 31/14* | (2006.01) | |
| *A61B 5/02* | (2006.01) | |
| *A61B 5/25* | (2021.01) | |
| *A61L 31/04* | (2006.01) | |
| *G01N 27/327* | (2006.01) | |
| *H01B 1/02* | (2006.01) | |
| *H01B 1/12* | (2006.01) | |

(52) U.S. Cl.
CPC ............... *C08K 3/046* (2017.05); *C08K 3/11* (2018.01); *C08K 9/02* (2013.01); *A61B 2562/0215* (2017.08); *A61B 2562/0285* (2013.01); *A61B 2562/125* (2013.01); *A61L 31/041* (2013.01); *A61L 2420/02* (2013.01); *C08K 2201/001* (2013.01); *G01N 27/327* (2013.01); *H01B 1/02* (2013.01); *H01B 1/122* (2013.01)

(56) References Cited

U.S. PATENT DOCUMENTS

| | | |
|---|---|---|
| 2002/0009650 A1 | 1/2002 | Michot et al. |
| 2002/0177039 A1 | 11/2002 | Lu et al. |
| 2002/0188069 A1 | 12/2002 | Sugo et al. |
| 2008/0118860 A1 | 5/2008 | Harada et al. |
| 2009/0061358 A1 | 3/2009 | Ohashi et al. |
| 2010/0252782 A1 | 10/2010 | Masahiro |
| 2014/0083750 A1* | 3/2014 | Chae ........................ H05K 1/09 174/257 |
| 2015/0275060 A1 | 10/2015 | Kuroda et al. |
| 2016/0155530 A1 | 6/2016 | Someya et al. |
| 2016/0260518 A1* | 9/2016 | Hatakeyama .......... H01B 3/301 |
| 2017/0130071 A1 | 5/2017 | Hatakeyama et al. |
| 2017/0275510 A1 | 9/2017 | Quan et al. |

FOREIGN PATENT DOCUMENTS

| | | |
|---|---|---|
| JP | 2003-225217 A | 8/2003 |
| JP | 2004-033468 A | 2/2004 |
| JP | 2004-527902 A | 9/2004 |
| JP | 2005-320418 A | 11/2005 |
| JP | 2008-111103 A | 5/2008 |
| JP | 2009-080474 A | 4/2009 |
| JP | 2011-079946 A | 4/2011 |
| JP | 2015-019806 A | 2/2015 |
| JP | 2015-100673 A | 6/2015 |
| JP | 2015-193803 A | 11/2015 |
| JP | 2016-011338 A | 1/2016 |
| JP | 2016-065238 A | 4/2016 |
| TW | 200927860 A | 7/2009 |
| TW | 201734149 A | 10/2017 |
| WO | 2013/039151 A1 | 3/2013 |

OTHER PUBLICATIONS

Jan. 11, 2021 Office Action and Search Report issued in Taiwanese Patent Application No. 108111460.

* cited by examiner

[FIG. 1]
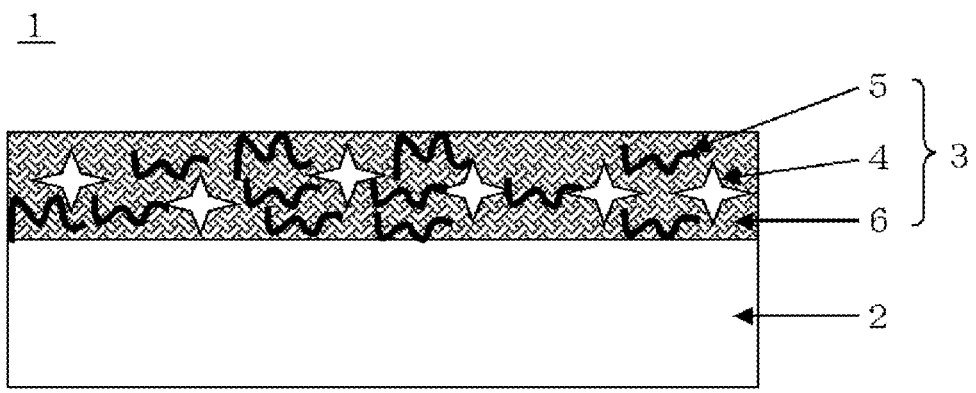
[FIG. 2]
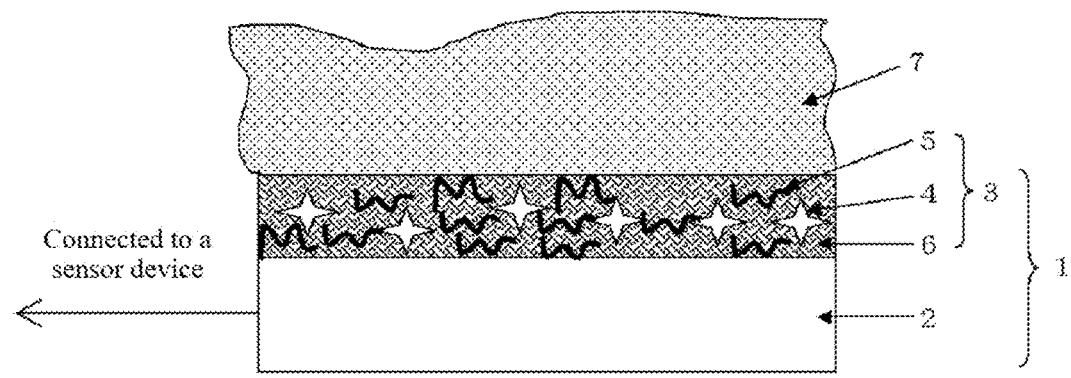
[FIG. 3A]
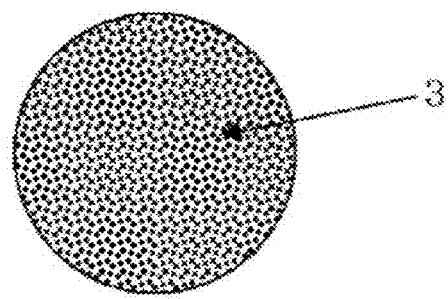

[FIG. 3B]
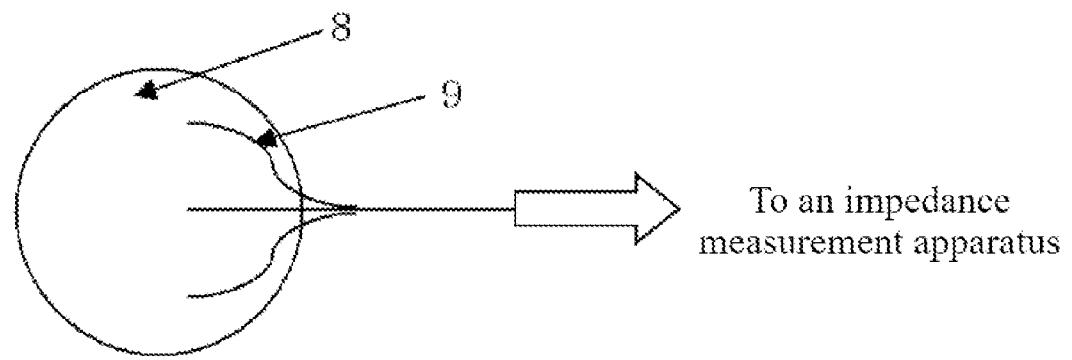
[FIG. 4]
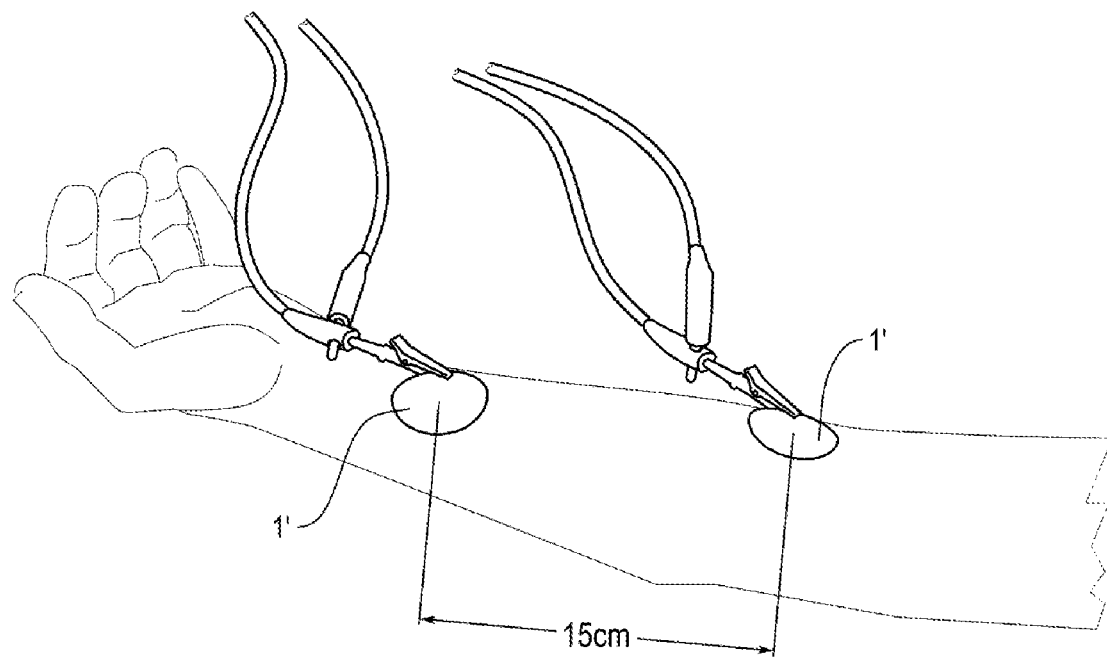

BIO-ELECTRODE COMPOSITION, BIO-ELECTRODE, AND METHOD FOR MANUFACTURING A BIO-ELECTRODE

CROSS-REFERENCE TO RELATED APPLICATION

This application claims priority to Japanese Patent Application No. 2018-70818, filed on Apr. 2, 2018, the content of which is hereby incorporated by reference in its entirety.

TECHNICAL FIELD

The present invention relates to a bio-electrode that is used in contact with the skin of a living body capable of detecting physical conditions such as heart rate by an electric signal transmitted from the skin, a method for manufacturing the bio-electrode, and a bio-electrode composition desirably used for a bio-electrode.

BACKGROUND ART

A recent growing popularity of Internet of Things (IoT) has accelerated the development of such major wearable devices as watches and glasses that allow for Internet access. Even in the fields of medicine and sports, wearable devices for constantly monitoring the user's physical state are increasingly demanded, and such technological development is expected to be further encouraged.

In the field of medicine, including an electrocardiogram for detecting an electric signal to measure the motion of the heart, use of wearable devices for monitoring the state of human organs by detecting extremely weak current has been examined. The electrocardiogram measurement is conducted by attaching an electrode coated with a conductive paste to a body, but this is a single (not continuous), short-time measurement. On the other hand, the above medical wearable device is aimed at monitoring the state of physical conditions for a few weeks. Accordingly, a bio-electrode used in a medical wearable device is required to make no changes in electric conductivity even in long-time use and cause no skin allergy. In addition to these, bio-electrodes must be light-weight and produced at low cost.

Medical wearable devices are classified into two types: direct body attachment and clothing attachment. One typical body attachment device is a bio-electrode formed of a hydrophilic gel containing water and electrolytes as ingredients of the above conductive paste (Patent Document 1). The hydrophilic gel, containing sodium, potassium, and calcium electrolytes in a hydrophilic polymer containing water, detects changes in ion concentration from the skin to convert the data into electricity. Meanwhile, one typical clothing attachment device is characterized by a method for using as an electrode a fabric including a conductive polymer, such as PEDOT-PSS (Poly-3,4-ethylenedioxythiophene-polystyrenesulfonate), and a silver paste incorporated into the fiber (Patent Document 2).

However, the use of the hydrophilic gel containing water and electrolytes unfortunately brings about loss of conductivity due to water evaporation in drying process. Meanwhile, the use of a higher ionization tendency metal such as copper can cause some users to suffer from skin allergy, as well as a conductive polymer such as PEDOT-PSS due to strong acidity.

By taking advantage of excellent conductivity, the use of electrode materials formed of metal nanowire, carbon black, or carbon nanotube has been examined (Patent Document 3, 4, and 5). With higher contact probability, metal nanowires can conduct electricity in small quantities to be added. Nevertheless, metal nanowires, formed of a pointed thin material, may cause skin allergy. Likewise, carbon nanotubes can stimulate (irritate) a living body. Although the carbon black is not as poisonous as carbon nanotube, it also stimulates the skin. Accordingly, even though these electrode materials themselves cause no allergic reaction, the biocompatibility can be degraded depending on the shape of a material and its inherent stimulation, thereby failing to satisfy both conductivity and biocompatibility.

Although metal films seem to function as an excellent bio-electrode thanks to extremely high conductivity, this is not always the case. Upon heartbeat, the human skin releases a sodium ion, a potassium ion, or a calcium ion, instead of extremely weak current. It is thus necessary to convert changes in ion concentration into current, which is what less ionized precious metals unfortunately fail to do efficiently. The resulting bio-electrode including the precious metal is characterized by high impedance and high resistance to the skin during electrical conduction.

Meanwhile, the use of a battery containing an ionic liquid has been examined (Patent Document 6). Advantageously, the ionic liquid is thermally and chemically stable, and the conductivity is excellent, providing more various battery applications. However, an ionic liquid having smaller molecular weight shown in Patent Document 6 unfortunately dissolves into water. A bio-electrode containing such an ionic liquid in use allows the ionic liquid to be extracted from the electrode by sweating, which not only lowers the conductivity, but also causes rough skin by the liquid soaking into the skin.

Batteries using a lithium salt of polymer type sulfonimide have been investigated (non-patent literature 1). Lithium has been applied to batteries because of their high ionic mobility, however, this is not a material with higher bio-compatibility.

In addition, any bio-electrode fails to get biological information when it is apart from the skin. The detection of even changes in contact area can vary quantities of electricity traveling through the electrode, allowing the baseline of an electrocardiogram (electric signal) to fluctuate. Accordingly, in order to stably detect electric signals from the body, the bio-electrode is required to be in constant contact with the skin and make no changes in contact area. This requirement is satisfied, preferably by use of adhesive biomedical electrodes. Moreover, elastic and flexible biomedical electrodes are needed to follow changes in skin expansion and flexion.

CITATION LIST

Patent Literature

Patent Literature 1: International Patent Laid-Open Publication No. WO 2013/039151
Patent Literature 2: Japanese Unexamined Patent Application Publication No. 2015-100673
Patent Literature 3: Japanese Unexamined Patent Application Publication No. H5-095924
Patent Literature 4: Japanese Unexamined Patent Application Publication No. 2003-225217
Patent Literature 5: Japanese Unexamined Patent Application Publication No. 2015-019806
Patent Literature 6: Japanese Unexamined Patent Application Publication No. 2004-527902

Non Patent Literature

Non Patent Document 1: J. Mater. Chem. A, 2016, 4, p 10038-10069

SUMMARY OF INVENTION

Technical Problem

The present invention was made in view of the situation to solve the problems, and has an object to provide a bio-electrode composition capable of forming a living body contact layer for a bio-electrode that is excellent in electric conductivity and biocompatibility, is light-weight, can be manufactured at low cost, and can control significant reduction in conductivity even though the bio-electrode is soaked in water or dried, a bio-electrode including a living body contact layer formed of the bio-electrode composition, and a method for manufacturing the bio-electrode.

Solution to Problem

To solve the above problems, the present invention provides a bio-electrode composition comprising:
(A) an ionic material; and
(B) a resin other than the component (A);
the component (A) comprising both of
  a repeating unit-a having a structure of a silver salt selected from the group consisting of silver salts of fluorosulfonic acid, fluorosulfonimide, and fluorosulfonamide; and
  a repeating unit-b having silicon.

The bio-electrode composition like this is capable of forming a living body contact layer for a bio-electrode that is excellent in electric conductivity and biocompatibility, light in weight, manufacturable at low cost, and free from large lowering of the electric conductivity even when it is wetted with water or dried.

It is preferable that the repeating unit-a have one or more structures selected from the structures shown by the following general formulae (1)-1 to (1)-4,

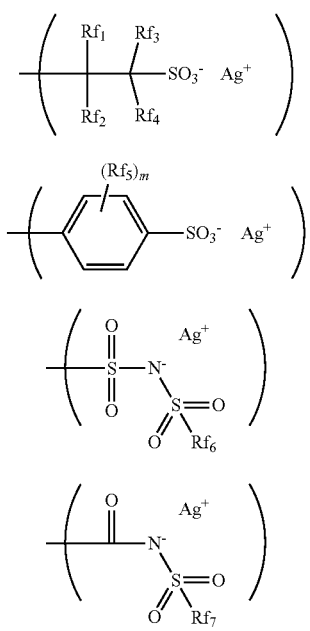

wherein $Rf_1$ and $Rf_2$ each represent a hydrogen atom, a methyl group, a fluorine atom, a trifluoromethyl group, or an oxygen atom, provided that when $Rf_2$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that one or more fluorine atoms are contained in $Rf_2$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; and "m" is an integer of 1 to 4.

The repeating unit-a having such a structure enables the bio-electrode composition to form a living body contact layer for a bio-electrode that is particularly excellent in electric conductivity and biocompatibility, light in weight, manufacturable at low cost, and free from large lowering of the electric conductivity even when it is wetted with water or dried.

It is preferable that the component (A) contain one or more repeating units selected from repeating units a1 to a7 shown by the following general formulae (2) as the repeating unit-a and a repeating unit-b1 shown by the following general formula (3) as the repeating unit-b,

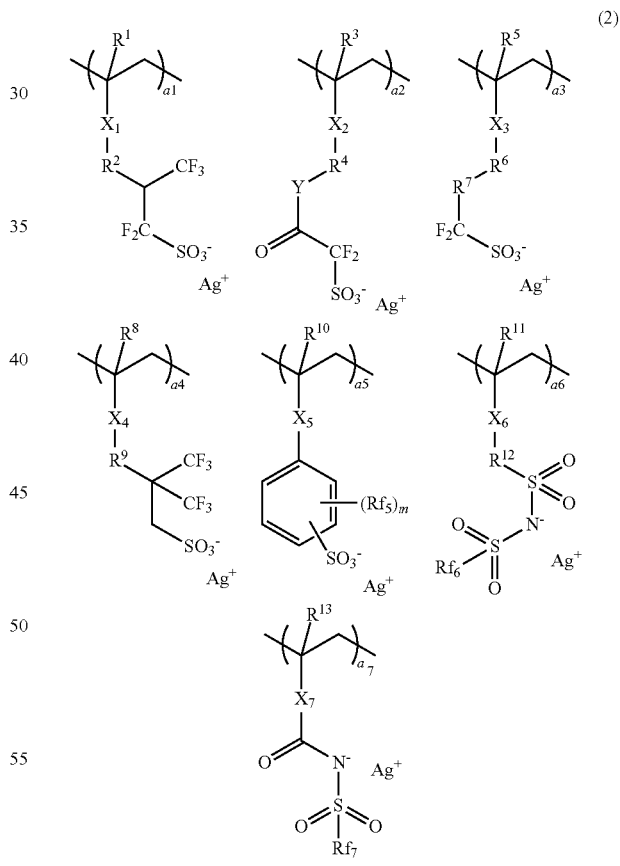

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 13 carbon atoms, optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $X_1$, $X_2$, $X_3$, $X_4$, and $X_6$ each independently represent any of a single bond, a phenylene group, a naphthylene group, an ether group, an ester group, or an amide group; $X_5$ represents any of a single bond, an ether group, or an ester group; $X_7$ represents a single bond, an arylene group having 6 to 12 carbon atoms, or —C(=O)—O—$X_{10}$—; and $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; Y represents an oxygen atom or an —$NR^{19}$— group, optionally bonded to $R^4$ to form a ring; $R^{19}$ represents a hydrogen atom, or a linear or branched alkyl group having 1 to 4 carbon atoms; $Rf_5$, $Rf_6$, and $Rf_7$ each represent a fluorine atom or a linear or branched alkyl group having 1 to 4 carbon atoms, and at least one fluorine atom is contained in $Rf_5$, $Rf_6$, and $Rf_7$; "m" is an integer of 1 to 4; a1, a2, a3, a4, a5, a6, and a7 are numbers satisfying 0≤a1<1.0, 0≤a2<1.0, 0≤a3<1.0, 0≤a4<1.0, 0≤a5<1.0, 0≤a6<1.0, 0≤a7<1.0, and 0<a1+a2+a3+a4+a5+a6+a7<1.0,

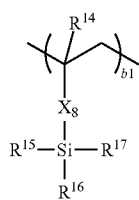

(3)

wherein $R^{14}$ represents a hydrogen atom or a methyl group; $X_8$ represents an arylene group having 6 to 12 carbon atoms, a —C(=O)—O—$R^{18}$— group, or a —C(=O)—NH—$R^{18}$— group; $R^{18}$ represents any of a single bond, a linear, branched, or cyclic alkylene group having 2 to 12 carbon atoms, or a phenylene group, optionally having one or more groups selected from an ether group, a carbonyl group, an ester group, and an amide group; $R^{15}$, $R^{16}$, and $R^{17}$ each represent a linear, branched, or cyclic alkyl group having 1 to 21 carbon atoms or an aryl group having 6 to 10 carbon atoms, optionally having one or more species selected from a siloxane bond, a silicon atom, and a halogen atom; $R^{15}$ and $R^{16}$, or $R^{15}$, $R^{16}$, and $R^{27}$ are optionally bonded to each other to form a ring or a three dimensional structure; and b1 is a number satisfying 0<b1<1.0.

With such a component (A), the effect of the present invention can be further improved.

It is also preferable that the component (A) contain a repeating unit-c shown by the following general formula (4) in addition to the repeating unit-a and the repeating unit-b,

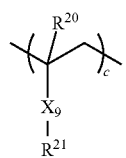

(4)

wherein $R^{20}$ represents a hydrogen atom or a methyl group; $X_9$ represents any of a single bond, a phenylene group, a naphthylene group, an ether group, an ester group, a phenylene group having an ester group, or an amide group; $R^{22}$ represents a linear, branched, or cyclic alkyl group having 1 to 40 carbon atoms, a linear, branched, or cyclic alkenyl group having 2 to 40 carbon atoms, a linear, branched, or cyclic alkynyl group having 2 to 40 carbon atoms, or an aryl group having 6 to 20 carbon atoms, optionally having an ether group, an ester group, or a hydroxy group; and "c" is a number satisfying 0<c<1.0.

Having such a repeating unit-c, the bio-electrode composition achieves higher adhesion (tackiness).

It is preferable that the component (B) contain a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit, diorganosiloxane having an alkenyl group, and organohydrogenpolysiloxane having an SiH group.

Such a component (B) securely makes the bio-electrode composition capable of preventing elution of the salt, holding an electric conductivity improver such as carbon, and achieving adhesion.

It is preferable that the bio-electrode composition further comprise an organic solvent.

The bio-electrode composition like this is further improved in the coating properties.

It is preferable that the bio-electrode composition further comprise a carbon material.

The bio-electrode composition like this is capable of forming a living body contact layer with more favorable electric conductivity.

It is preferable that the carbon material be either or both of carbon black and carbon nanotube.

In the bio-electrode composition of the present invention, these carbon materials can be used particularly favorably.

The present invention also provides a bio-electrode comprising an electro-conductive base material and a living body contact layer formed on the electro-conductive base material;

wherein the living body contact layer is a cured material of the inventive bio-electrode composition described above.

In the bio-electrode like this, the living body contact layer is formed from a bio-electrode composition that is excellent in electric conductivity and biocompatibility, light in weight, manufacturable at low cost, and free from large lowering of the electric conductivity even when it is wetted with water or dried.

It is preferable that the electro-conductive base material comprise one or more species selected from gold, silver, silver chloride, platinum, aluminum, magnesium, tin, tungsten, iron, copper, nickel, stainless steel, chromium, titanium, and carbon.

In the bio-electrode of the present invention, these electro-conductive base materials can be used particularly favorably.

The present invention also provides a method for manufacturing a bio-electrode having an electro-conductive base material and a living body contact layer formed on the electro-conductive base material, comprising:

applying the bio-electrode composition described above onto the electro-conductive base material; and curing the bio-electrode composition; thereby forming the living body contact layer.

By the method for manufacturing a bio-electrode like this, it is possible to easily manufacture a bio-electrode at low cost, in which the living body contact layer is excellent in electric conductivity and biocompatibility, light in weight, and free from large lowering of the electric conductivity even when it is wetted with water or dried.

It is preferable that the electro-conductive base material comprise one or more species selected from gold, silver, silver chloride, platinum, aluminum, magnesium, tin, tungsten, iron, copper, nickel, stainless steel, chromium, titanium, and carbon.

In the inventive method for manufacturing a bio-electrode, these electro-conductive base materials can be used particularly favorably.

Advantageous Effects of Invention

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried. The electric conductivity can be more improved by adding a carbon material. It is possible to manufacture a bio-electrode with particularly high adhesion and stretchability by combining a resin having adhesion and stretchability. Additionally, the stretchability and the adhesion to skin can be improved using an additive and so on. The stretchability and the adhesion can be controlled by adjusting the composition of the resin or the thickness of the living body contact layer appropriately. Accordingly, the inventive bio-electrode, with the living body contact layer being formed by using the inventive bio-electrode composition like this, is particularly suitable as a bio-electrode used for a medical wearable device. Moreover, the inventive method for manufacturing a bio-electrode makes it possible to manufacture such a bio-electrode easily at low cost.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3A is a schematic view of the bio-electrode produced in Examples of the present invention viewed from the living body contact layer side;

FIG. 3B is a schematic view of the bio-electrode produced in Examples of the present invention viewed from the electro-conductive base material side; and FIG. 4 is a photograph of a scene of measuring impedance on the surface of skin by using the bio-electrode produced in Examples of the present invention.

DESCRIPTION OF EMBODIMENTS

As described above, it has been desired to develop a bio-electrode composition capable of forming a living body contact layer for a bio-electrode that is excellent in electric conductivity and biocompatibility, light in weight, manufacturable at low cost, and free from large lowering of the electric conductivity even when it is wetted with water or dried; a bio-electrode in which the living body contact layer is formed from the bio-electrode composition; and a method for manufacturing the same.

The inventors have noticed ionic liquids as an ionic material (an electric conductive material) to be contained in a bio-electrode composition for forming a living body contact layer for a bio-electrode. Ionic liquids are characterized by high thermal and chemical stability as well as excellent electric conductivity, thereby having been widely used for battery uses. Illustrative examples of known ionic liquid include hydrochloric acid salt, hydrobromic acid salt, hydroiodic acid salt, trifluoromethanesulfonic acid salt, nonafluorobutanesulfonic acid salt, bis(trifluoromethanesulfonyl)imide acid salt, hexafluorophosphate salt, and tetrafluoroborate salt of sulfonium, phosphonium, ammonium, morpholinium, pyridinium, pyrrolidinium, and imidazolium. However, these salts (particularly, the ones with low molecular weight) are generally liable to hydrate. Therefore, in a bio-electrode in which the living body contact layer is formed from a bio-electrode composition containing these salts, there has been a defect of lowering the electric conductivity due to extraction of the salt with perspiration or by washing. In addition, there is the problem that the tetrafluoroborate salt is highly toxic, and the other salts have high solubility in water to easily permeate into skin, each of which causes rough dry skin (i.e., highly irritative to skin).

In neutralized salts formed from highly acidic acids, the ions are strongly polarized to improve the ionic conductivity. This is the reason why lithium salts of bis(trifluoromethanesulfonyl)imidic acid and tris(trifluoromethanesulfonyl) methide acid show high ionic conductivity as a lithium ion battery. On the other hand, the higher acidity makes the salt have stronger irritation to a body. That is, ionic conductivity and irritation to a body are in relation of trade-off. In a salt applied to a bio-electrode, however, higher ionic conductivity and lower irritation to a body have to be compatible.

Accordingly, the inventors have diligently studied the above subjects and found that a polymer compound having a repeating unit of a silver salt selected from silver salts of fluorosulfonic acid, fluorosulfonimide, and fluorosulfonamide is highly ionic conductive and less-irritative to skin due to the non-permeability to skin, thereby forming a living body contact layer through copolymerization with a monomer containing silicon followed by mixing the polymer to silicone base, acrylic base, or urethane base adhesive (resin) for example, making it possible to function as a bio-electrode that can achieve both of electric conductivity and biocompatibility, can be prevented from causing large lowering of the electric conductivity even when it is wetted with water or dried, and can be in contact with skin continually to obtain stable electric signals in a long period; thereby completing the present invention.

That is, the present invention is a bio-electrode composition comprising:
(A) an ionic material; and
(B) a resin other than the component (A);
the component (A) comprising both of
  a repeating unit-a having a structure of a silver salt selected from the group consisting of silver salts of fluorosulfonic acid, fluorosulfonimide, and fluorosulfonamide; and
  a repeating unit-b having silicon.

Hereinafter, the present invention will be described specifically, but the present invention is not limited thereto.

<Bio-Electrode Composition>

The inventive bio-electrode composition contains (A) an ionic material and (B) a resin other than the component (A). Hereinafter, each component will be described more specifically.

[(A) Ionic Material (Salt)]

In the polymeric salt to be added to the inventive bio-electrode composition as (A) the ionic material, the repeating unit-a having a structure of any of a silver salts of fluorosulfonic acid, fluorosulfonimide, and fluorosulfonamide preferably has one or more structures shown by the following general formulae (1)-1 to (1)-4,

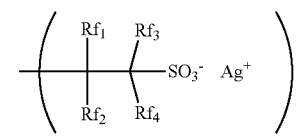

(1)-1

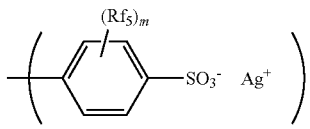

(1)-2

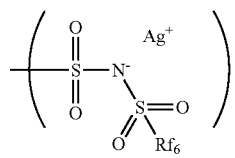

(1)-3

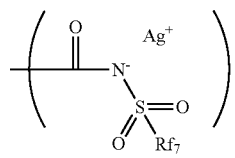

(1)-4 wherein $Rf_2$ and $Rf_2$ each represent a hydrogen atom, a methyl group, a fluorine atom, a trifluoromethyl group, or an oxygen atom, provided that when $Rf_2$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that one or more fluorine atoms are contained in $Rf_2$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; and "m" is an integer of 1 to 4.

(Repeating Unit-a)

The component (A) of the inventive bio-electrode composition preferably contains one or more repeating units selected from repeating units a1 to a7 shown by the following general formulae (2),

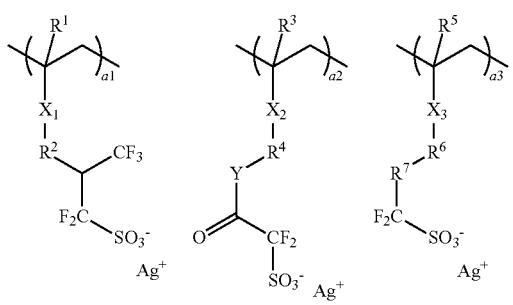

(2)

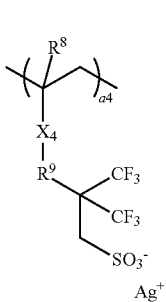 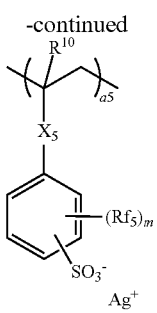 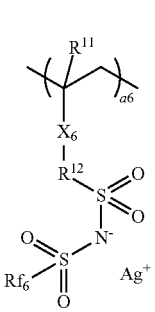

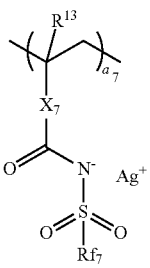

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, and a linear, branched, or cyclic hydrocarbon group having 1 to 13 carbon atoms, optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $X_1$, $X_2$, $X_3$, $X_4$, and $X_6$ each independently represent any of a single bond, a phenylene group, a naphthylene group, an ether group, an ester group, and an amide group; $X_5$ represents any of a single bond, an ether group, and an ester group; $X_7$ represents a single bond, an arylene group having 6 to 12 carbon atoms, or —C(=O)—O—$X_{10}$—; and $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; Y represents an oxygen atom or an —$NR^{19}$— group, optionally bonded to $R^4$ to form a ring; $R^{19}$ represents a hydrogen atom, or a linear or branched alkyl group having 1 to 4 carbon atoms; $Rf_5$, $Rf_6$, and $Rf_7$ each represent a fluorine atom or a linear or branched alkyl group having 1 to 4 carbon atoms, and at least one fluorine atom is contained in $Rf_5$, $Rf_6$, and $Rf_7$; "m" is an integer of 1 to 4; a1, a2, a3, a4, a5, a6, and a7 are numbers satisfying 0≤a1<1.0, 0≤a2<1.0, 0≤a3<1.0, 0≤a4<1.0, 0≤a5<1.0, 0≤a6<1.0, 0≤a7<1.0, and 0<a1+a2+a3+a4+a5+a6+a7<1.0.

Among the repeating units a1 to a7 shown by the general formulae (2), the repeating units a1 to a5 can be obtained from the fluorosulfonic acid salt monomers exemplified below.

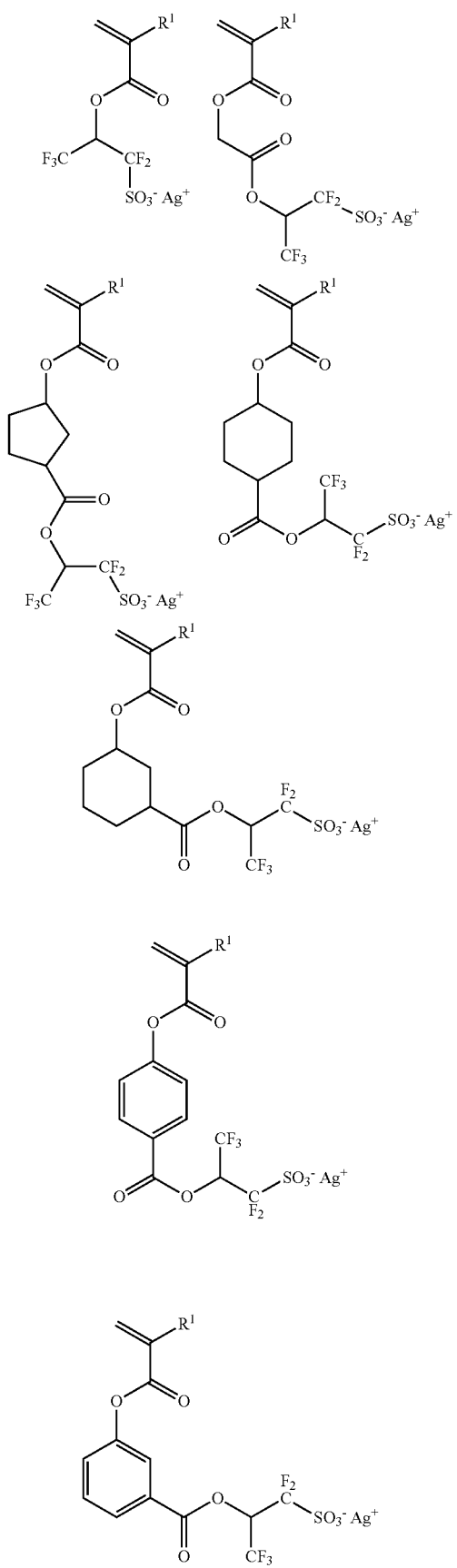
-continued
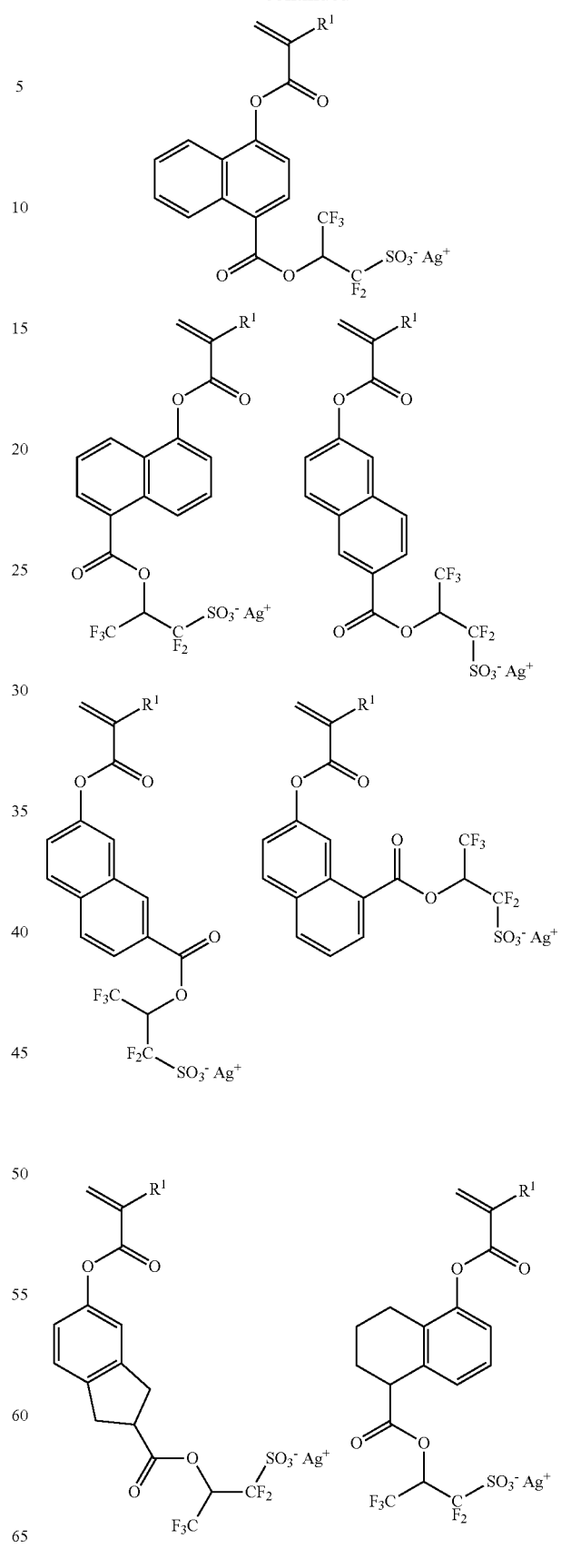

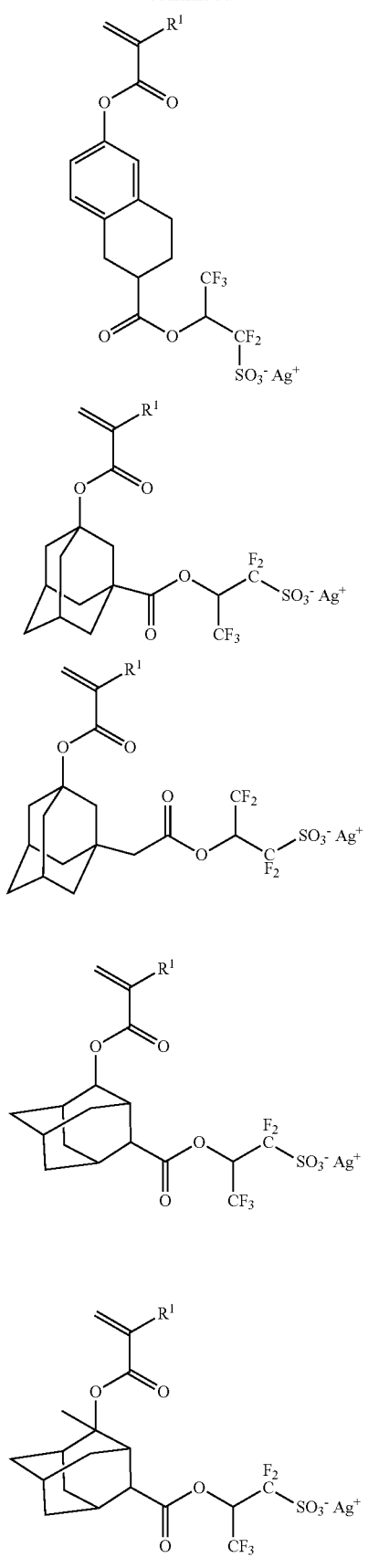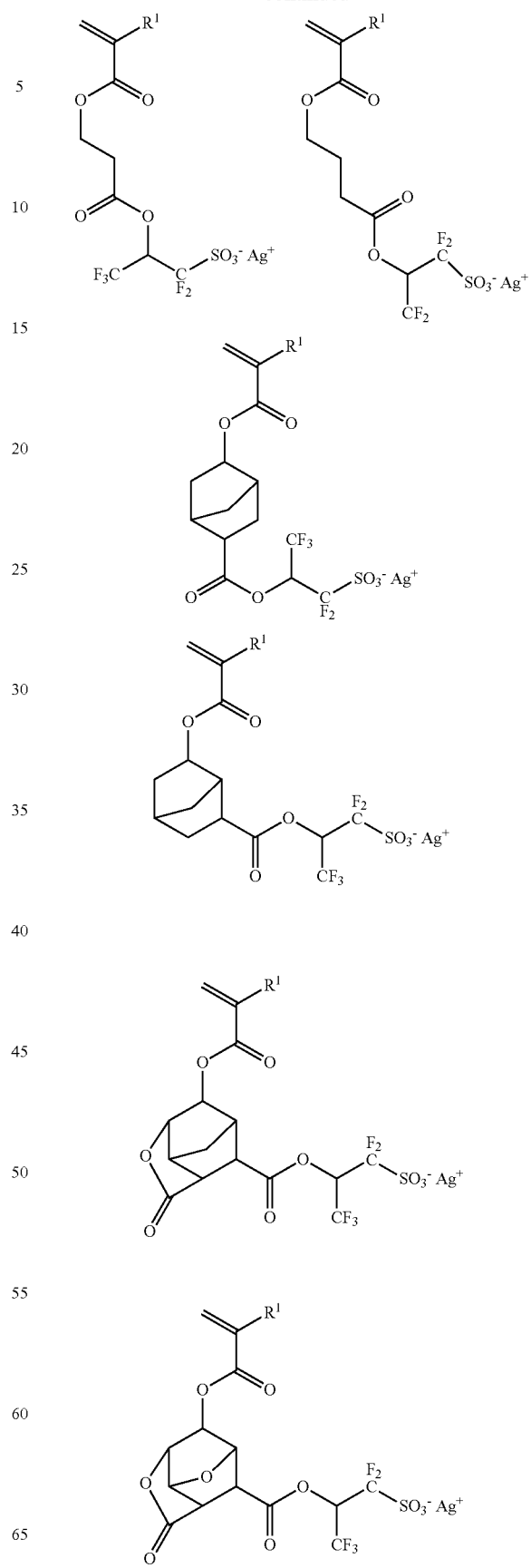

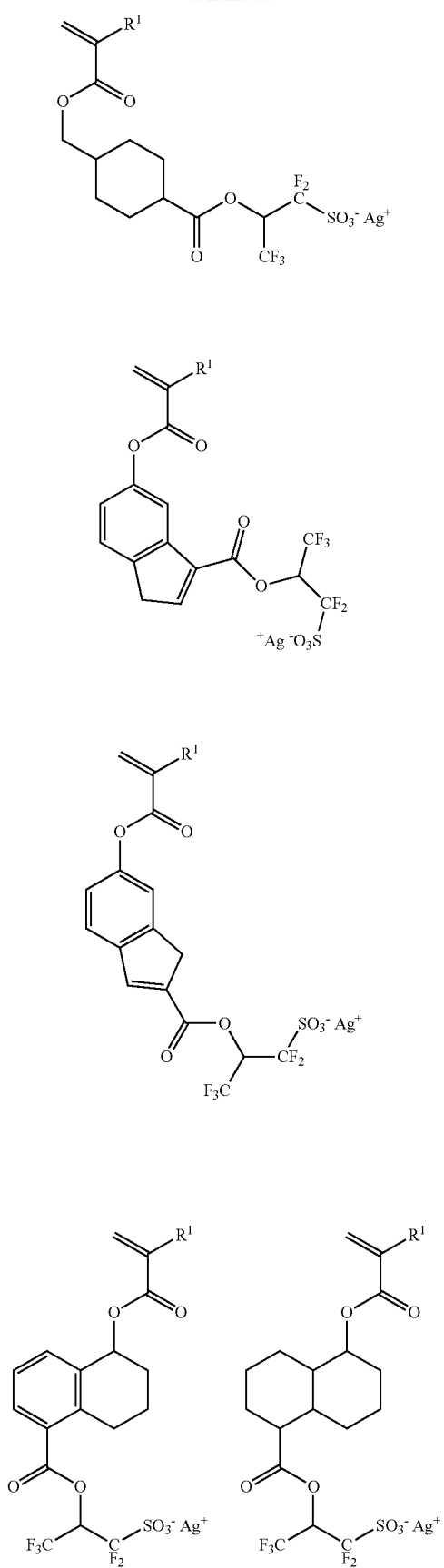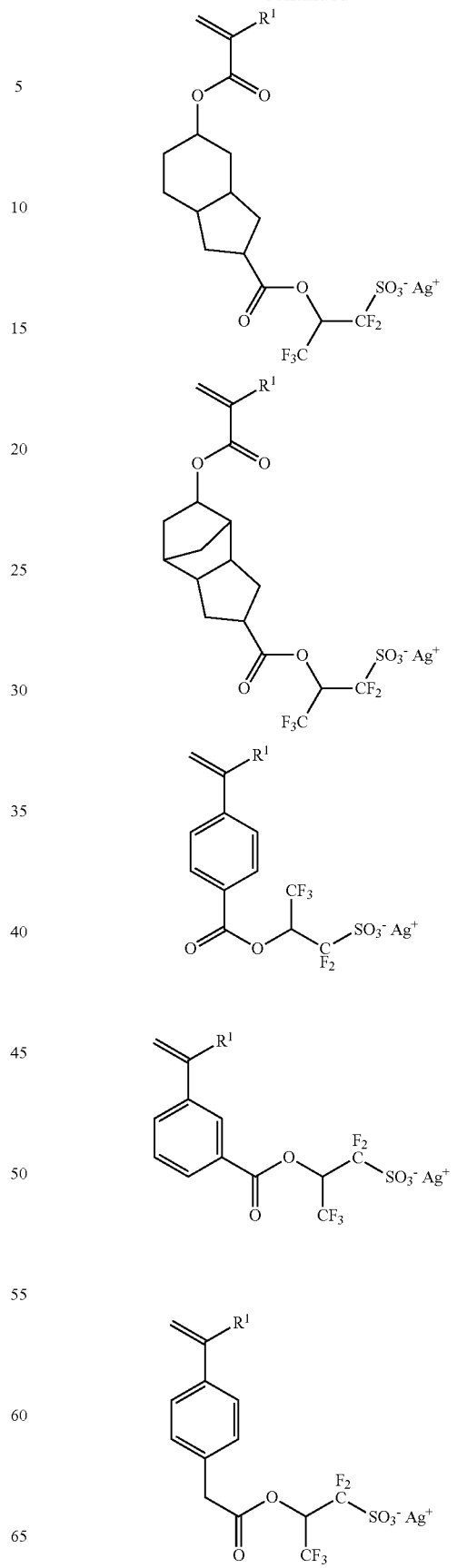

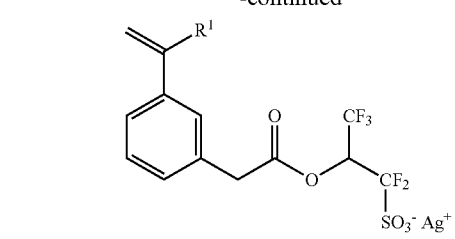
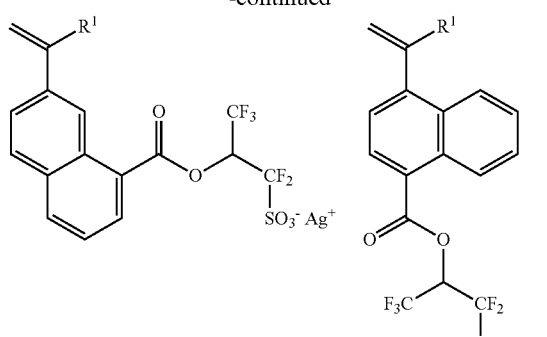
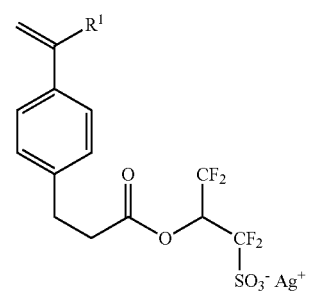
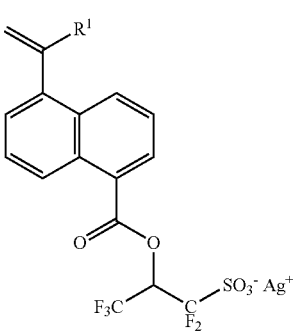
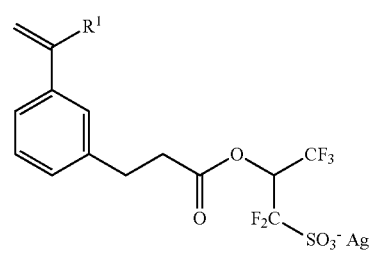
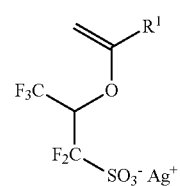
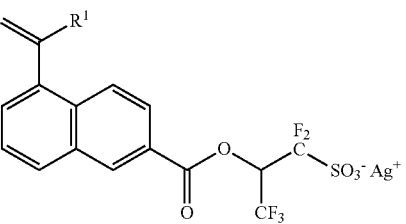
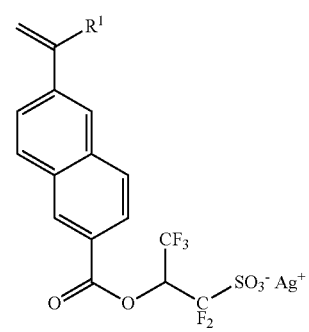
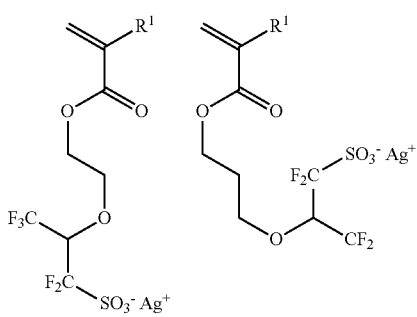
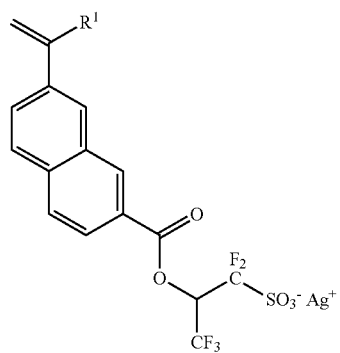
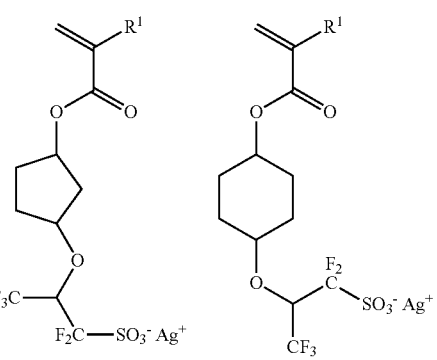

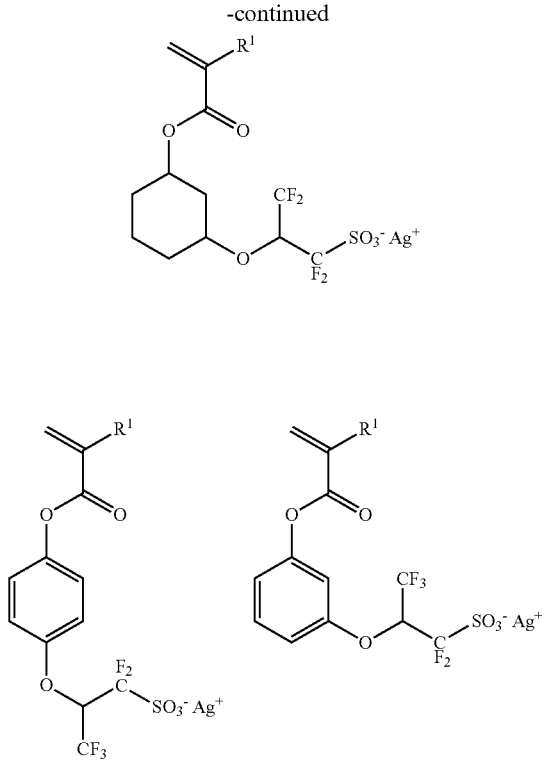
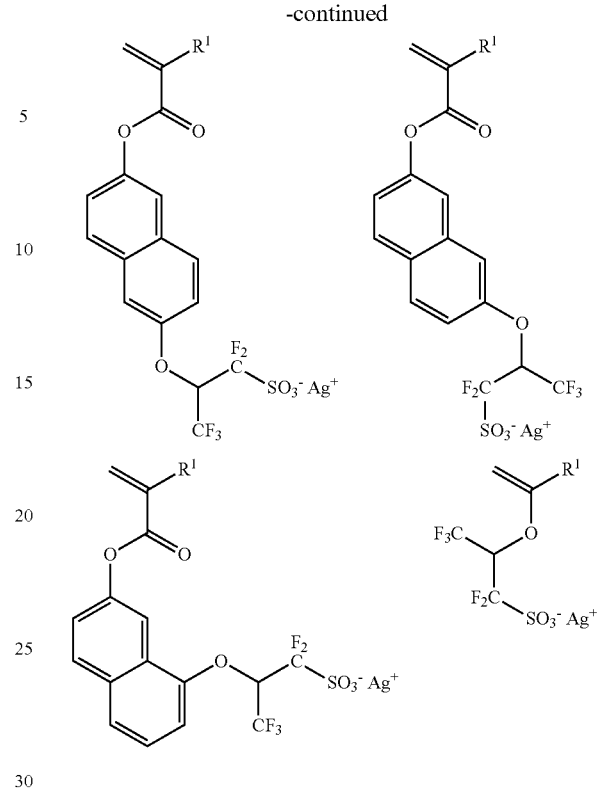
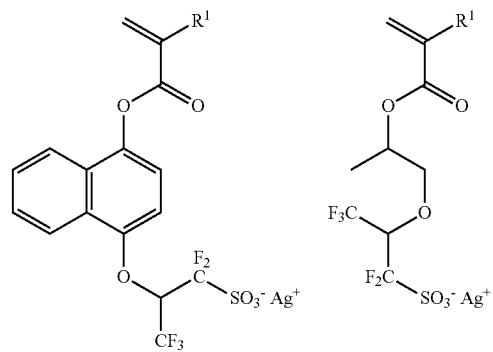
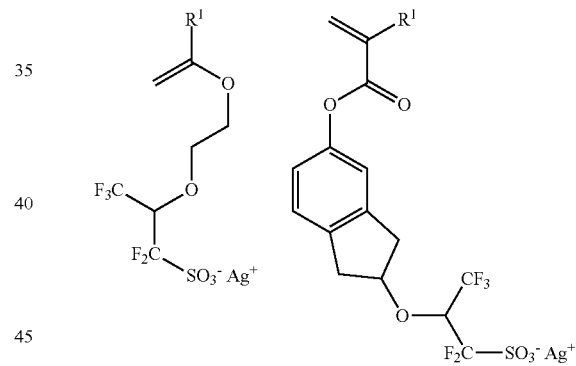
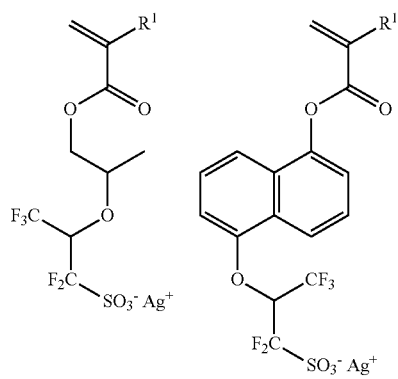
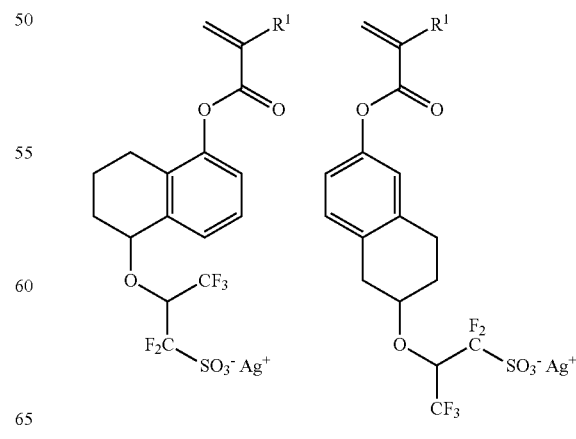

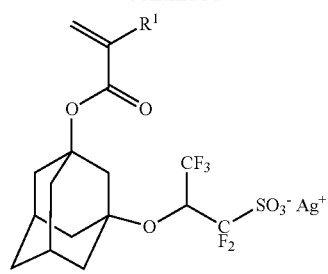
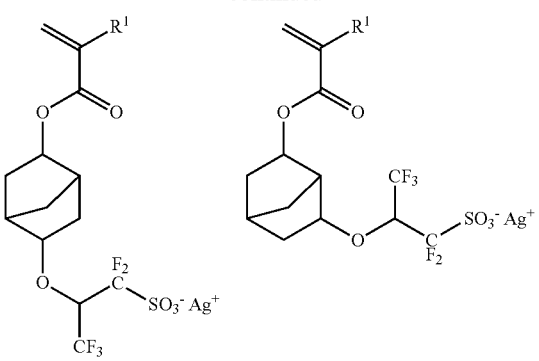
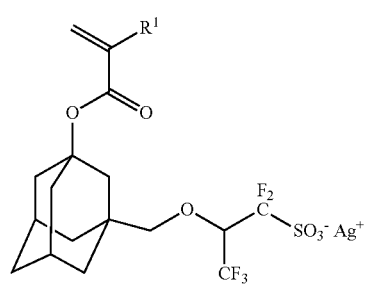
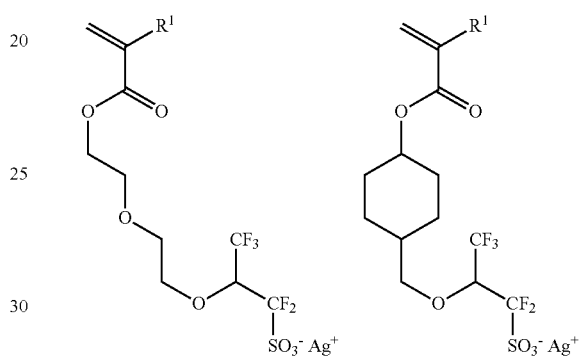
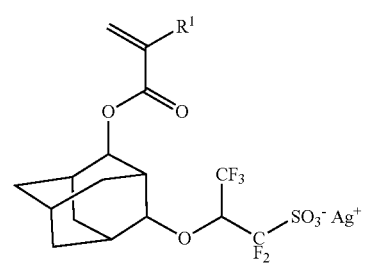
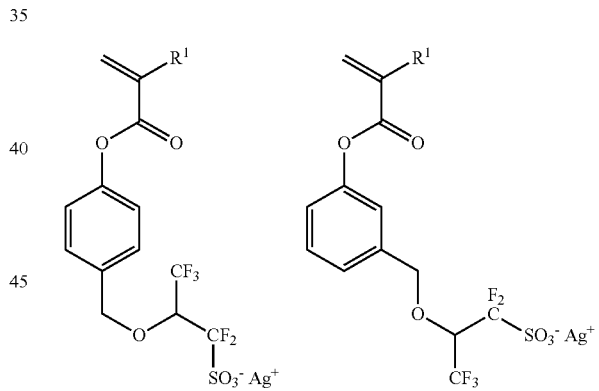
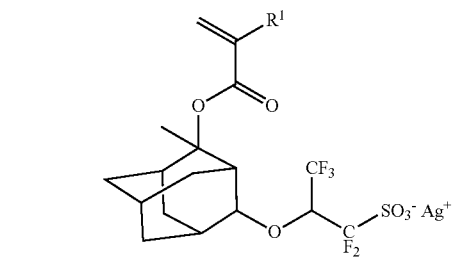
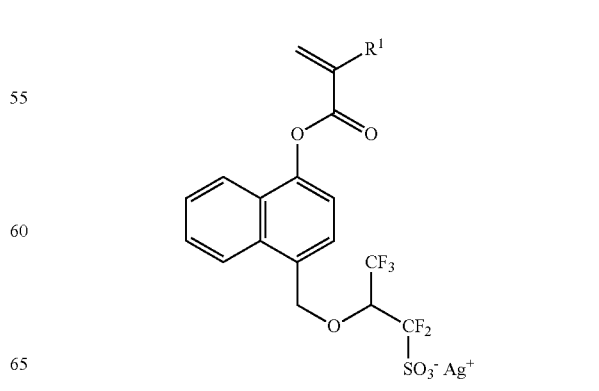
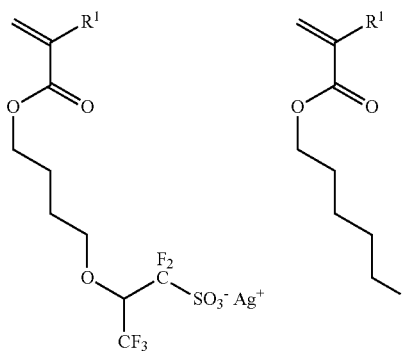

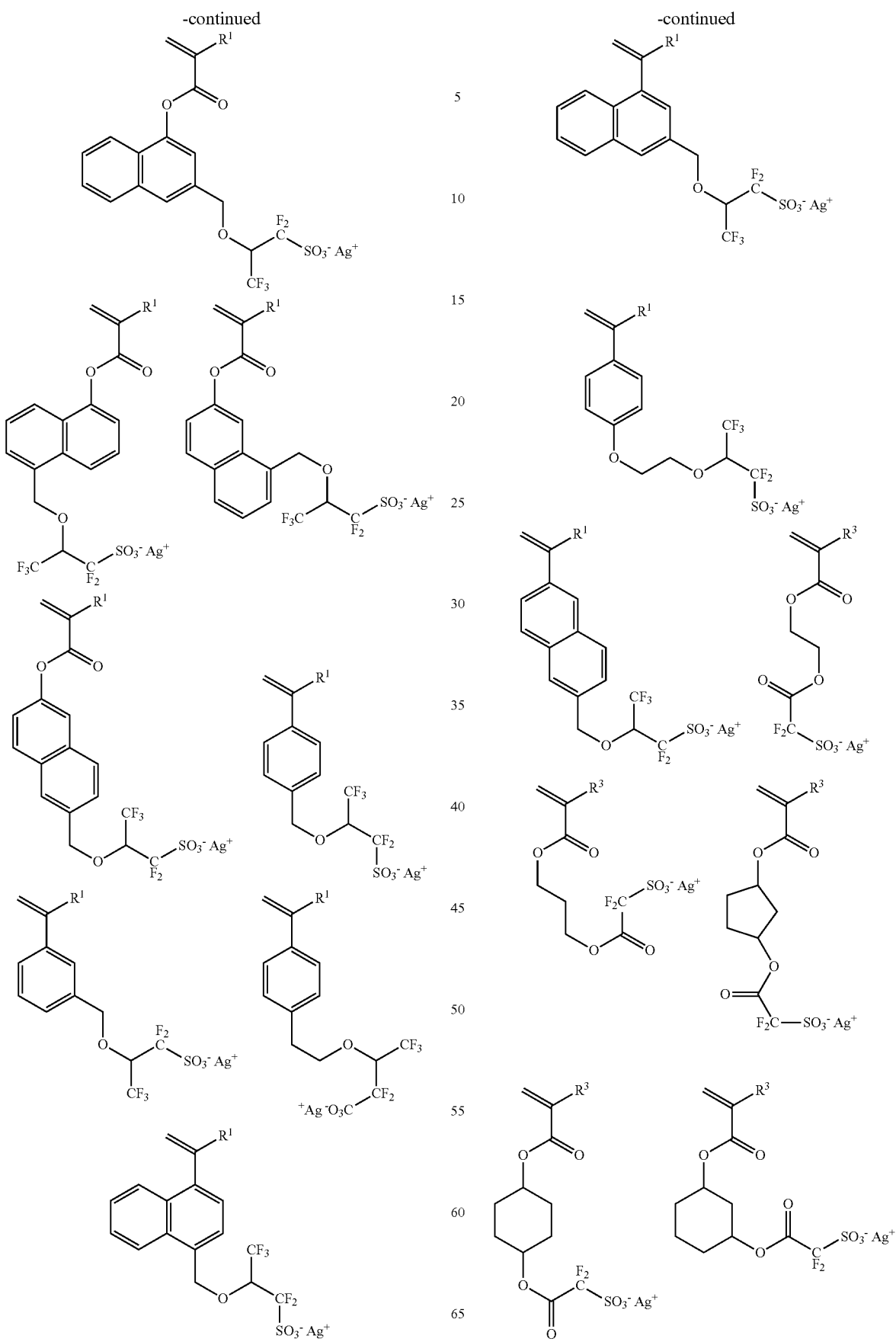

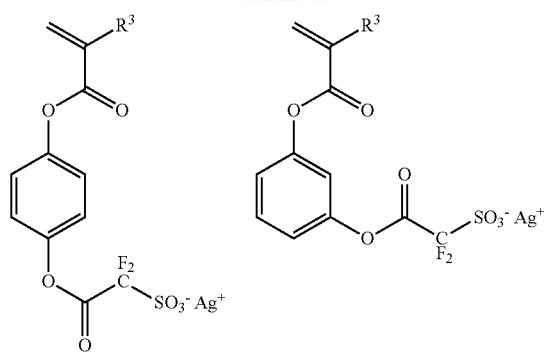
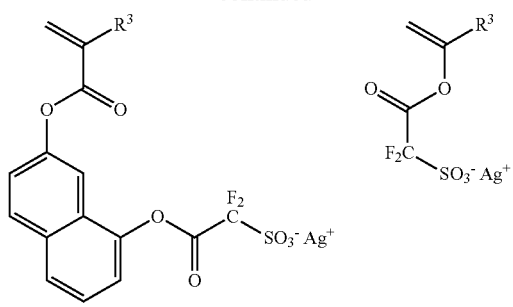
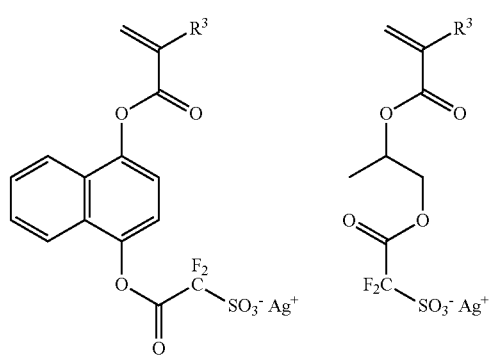
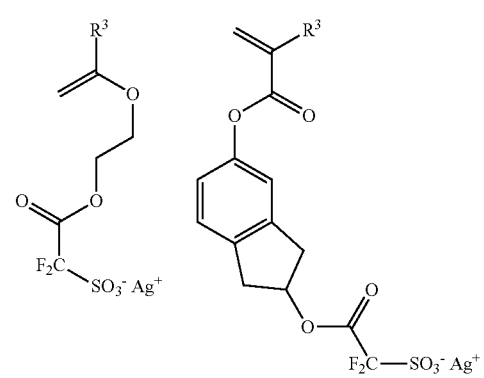
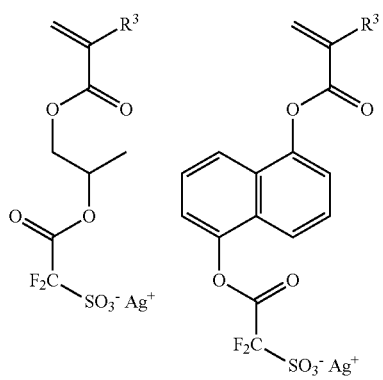
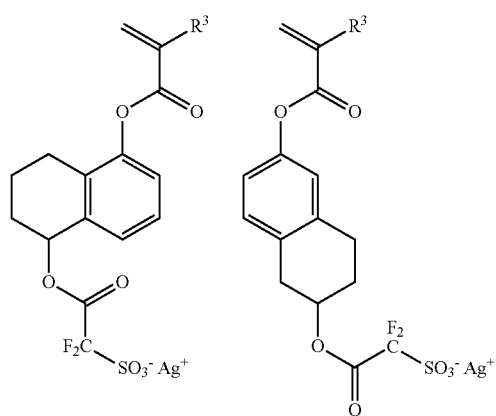
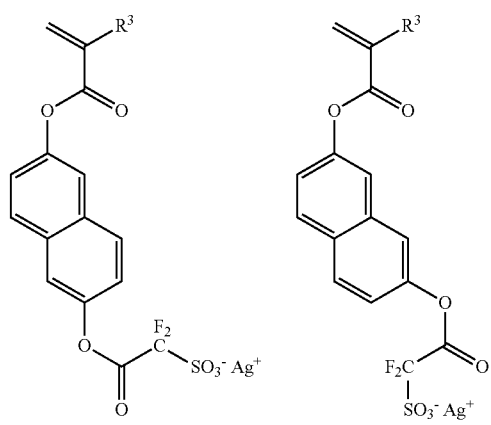
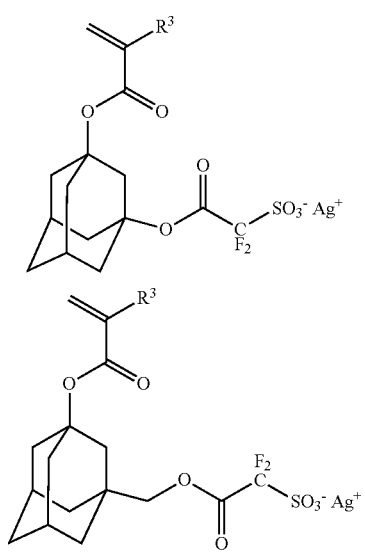

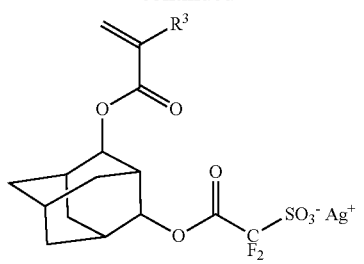
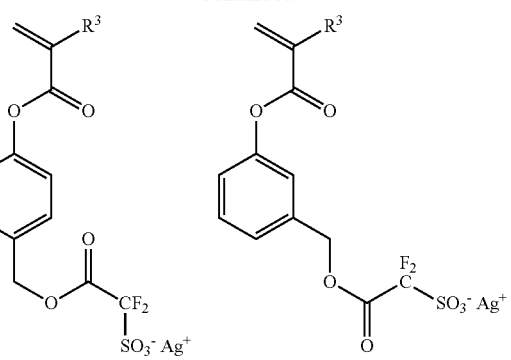
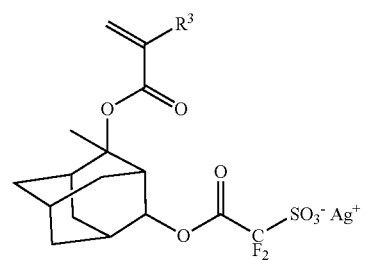
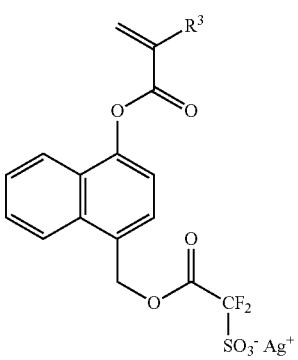
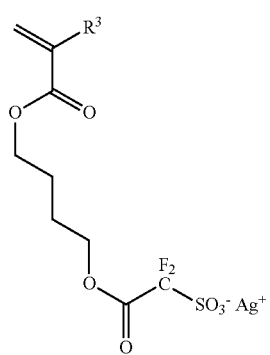
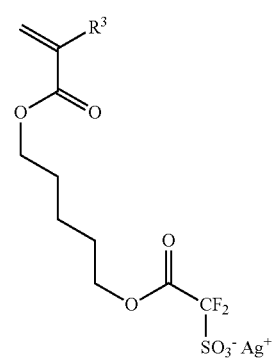
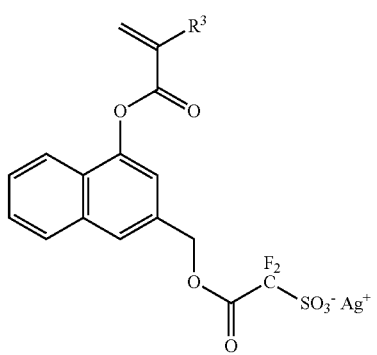
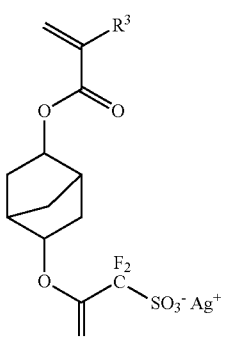
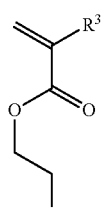
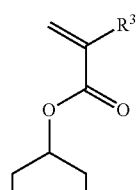
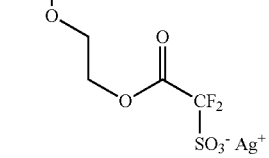
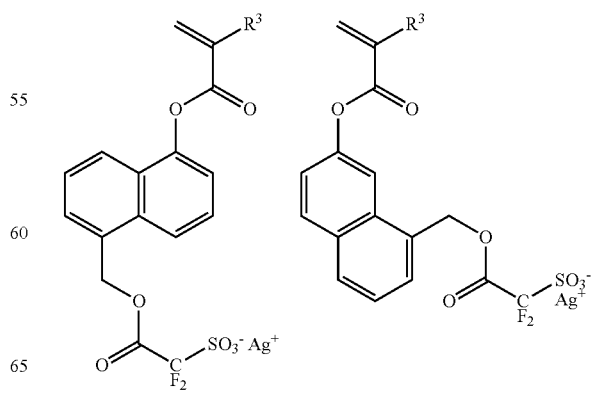

29
-continued
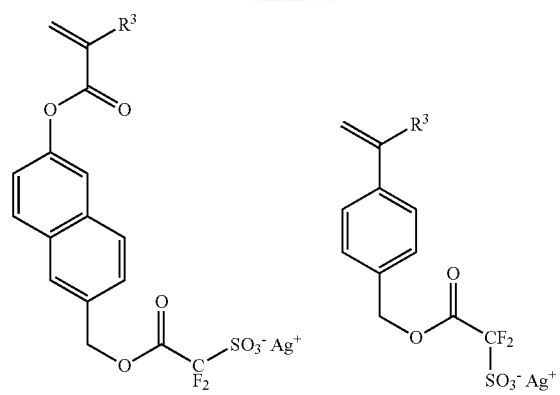
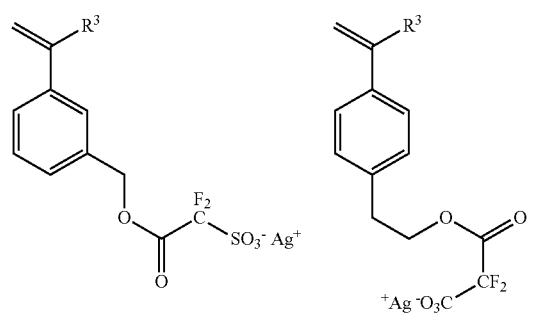
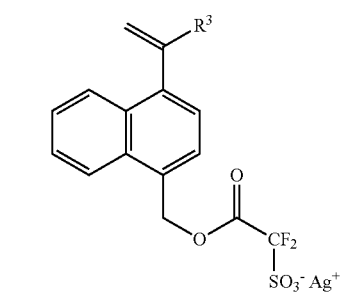
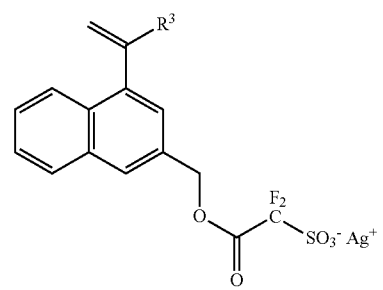
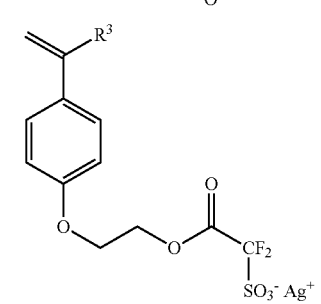
30
-continued
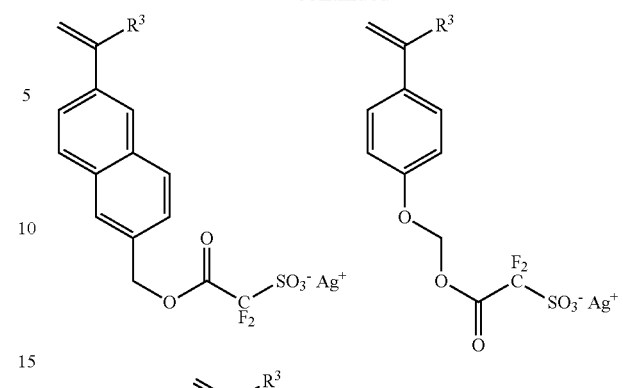
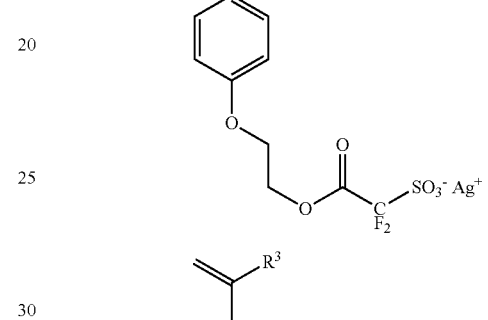
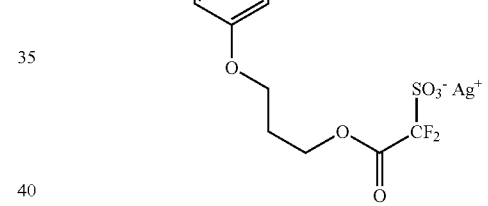
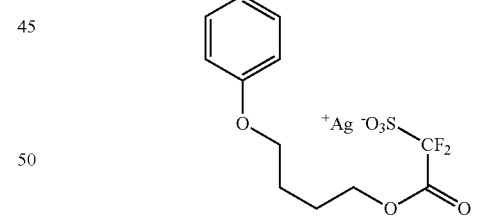
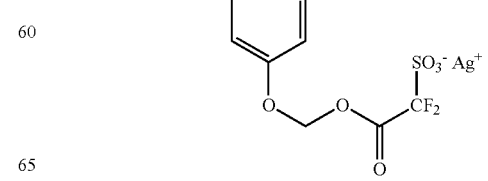

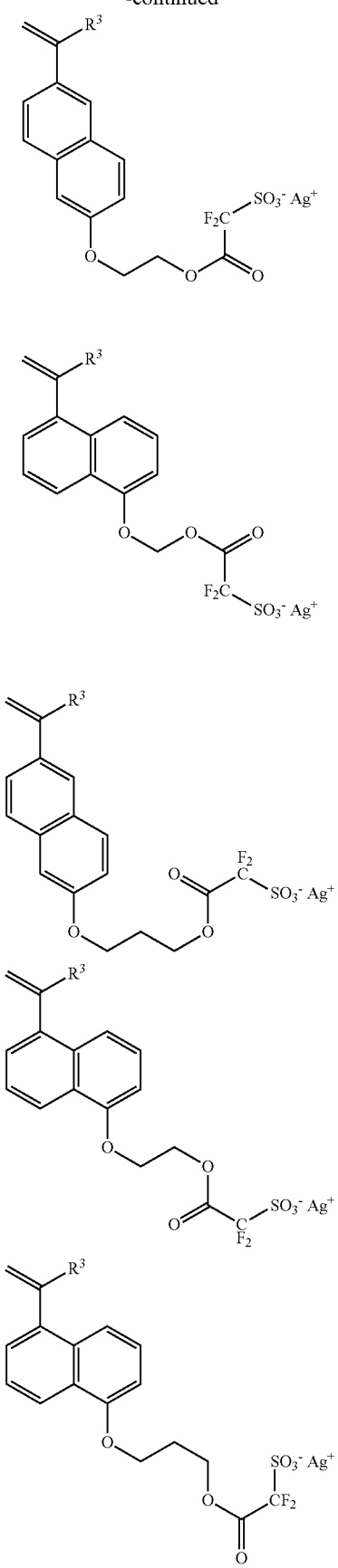
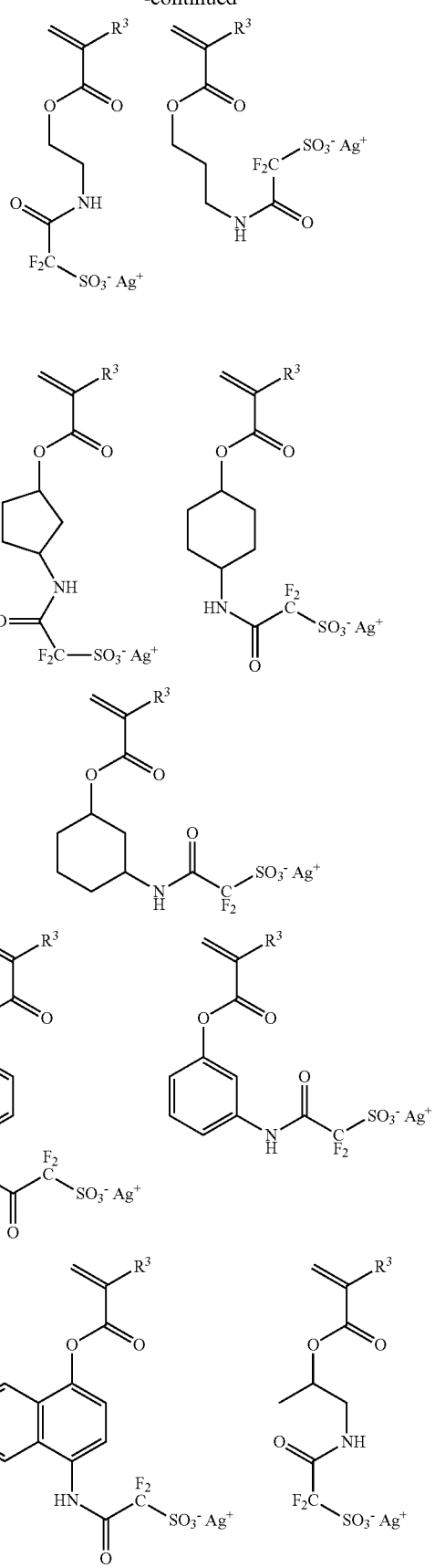

33
-continued
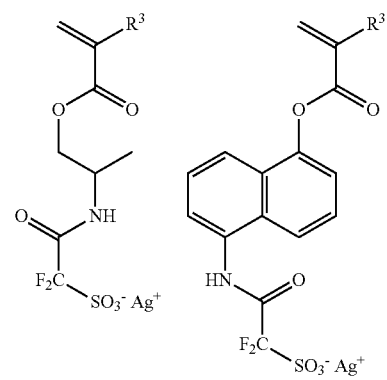
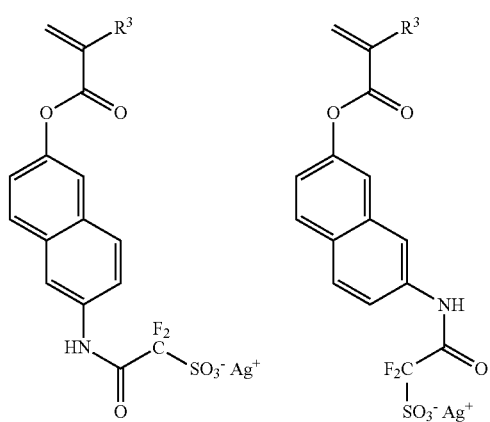
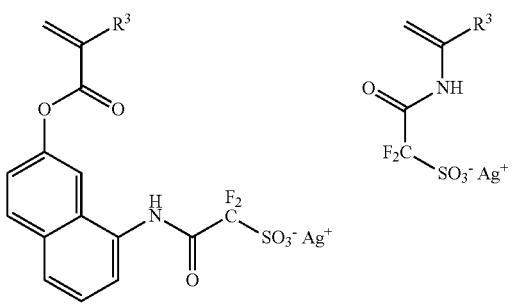
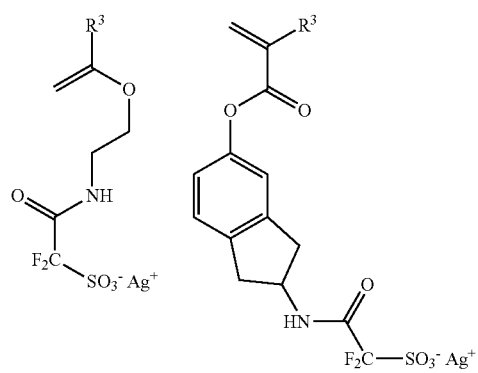
34
-continued
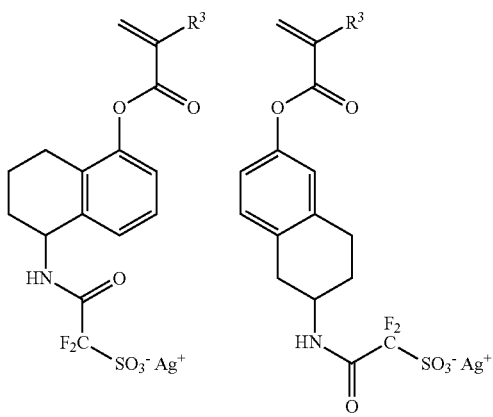
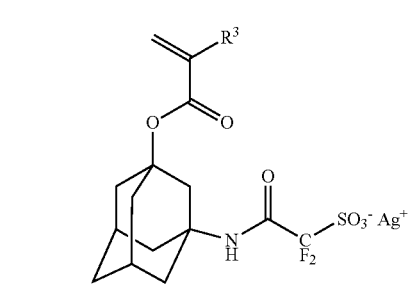
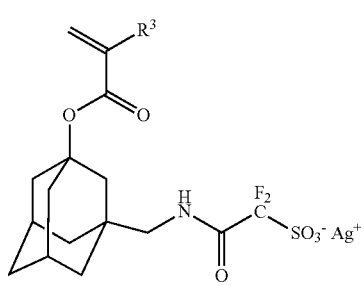
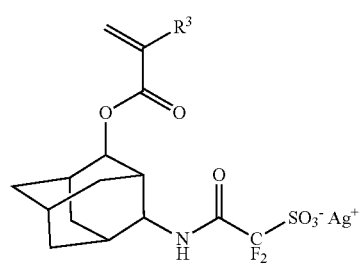
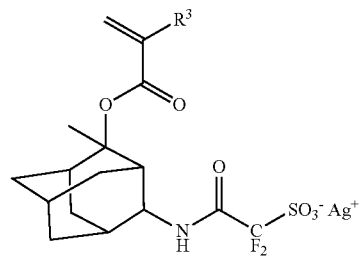

-continued
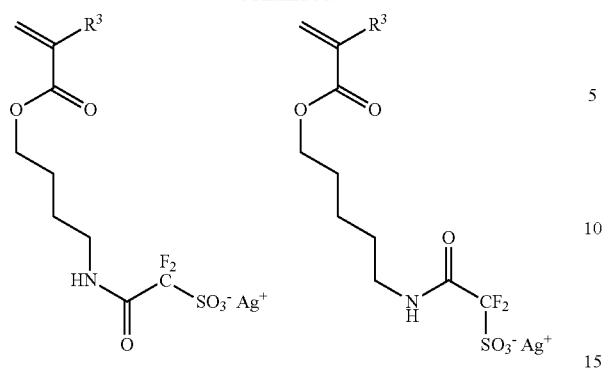 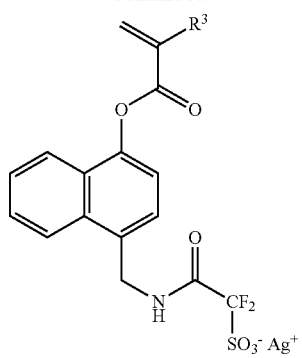
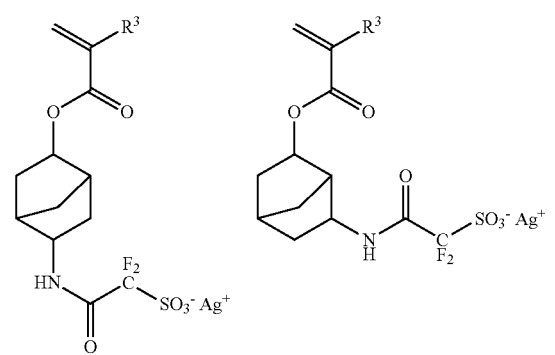 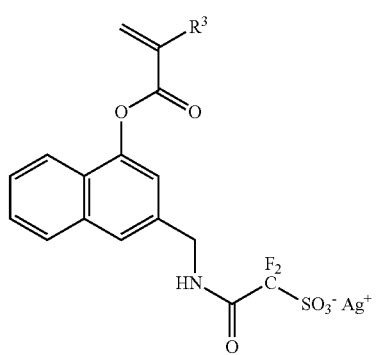
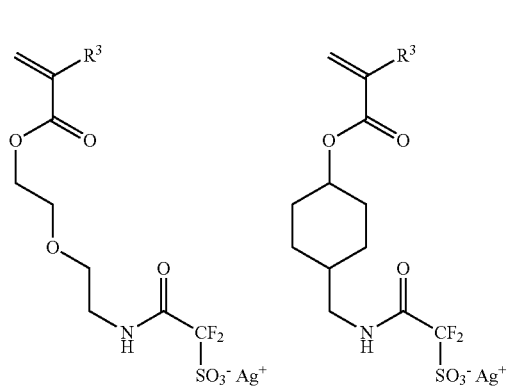 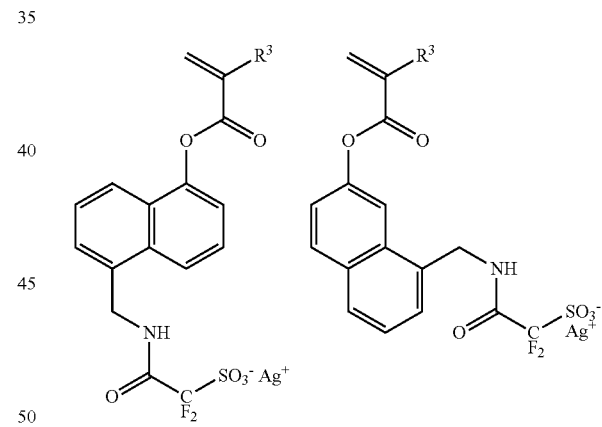
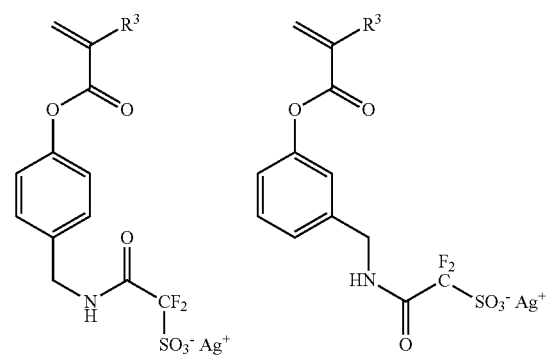 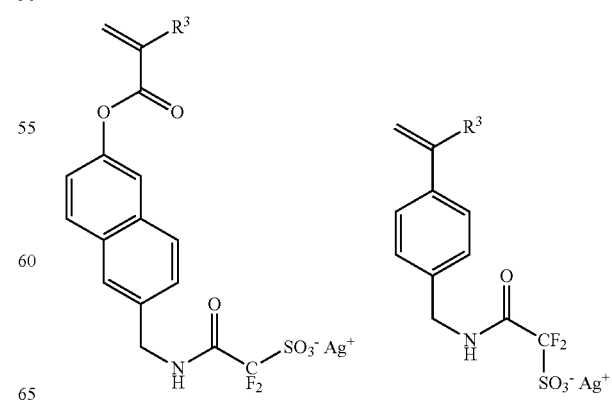

37
-continued
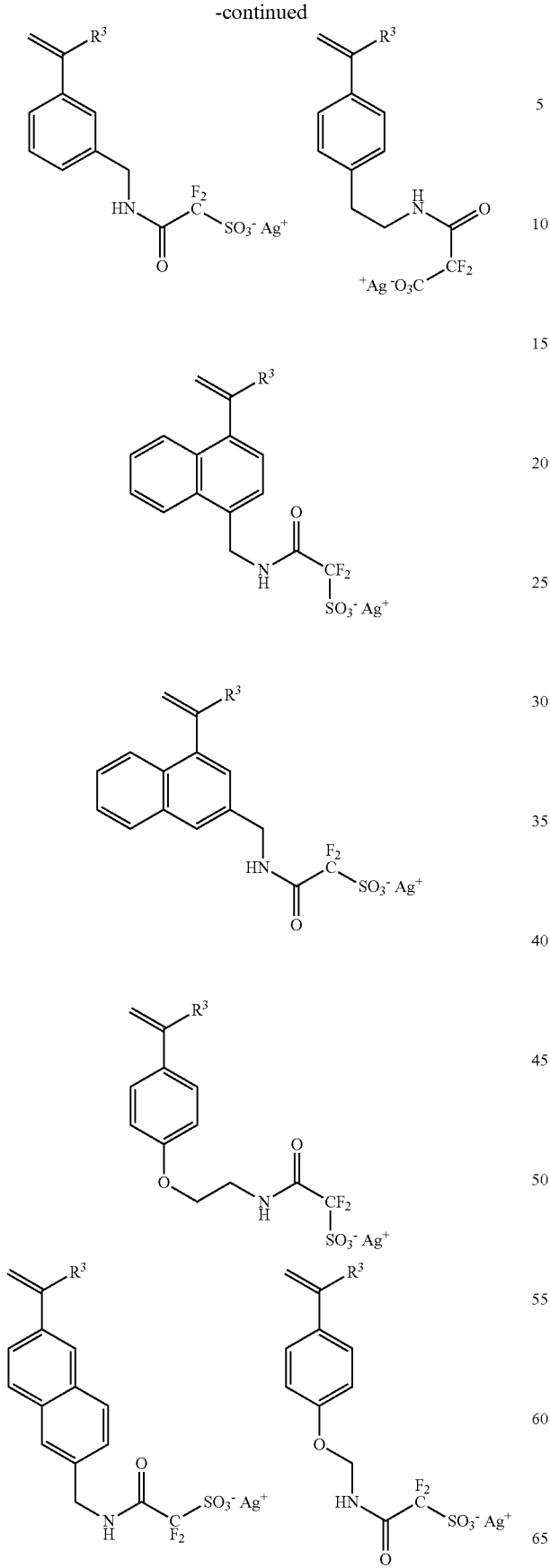
38
-continued
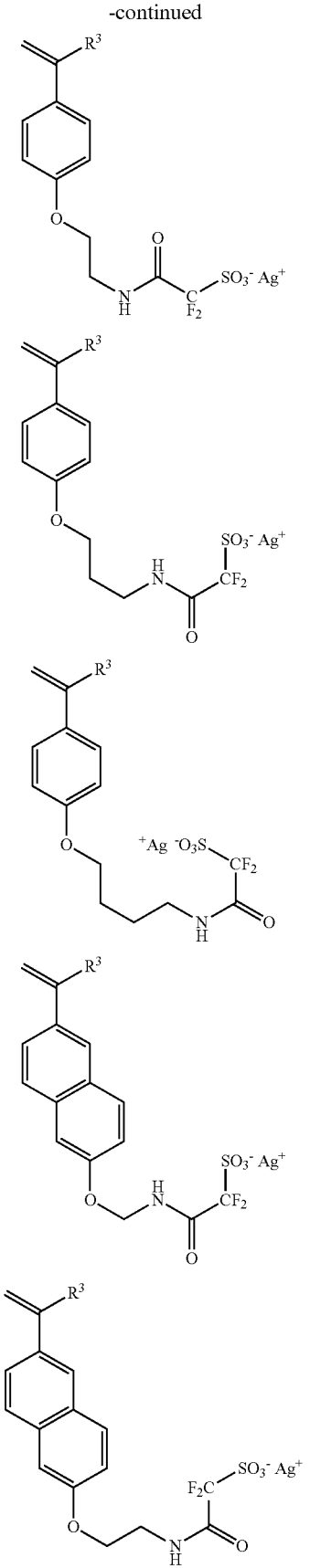

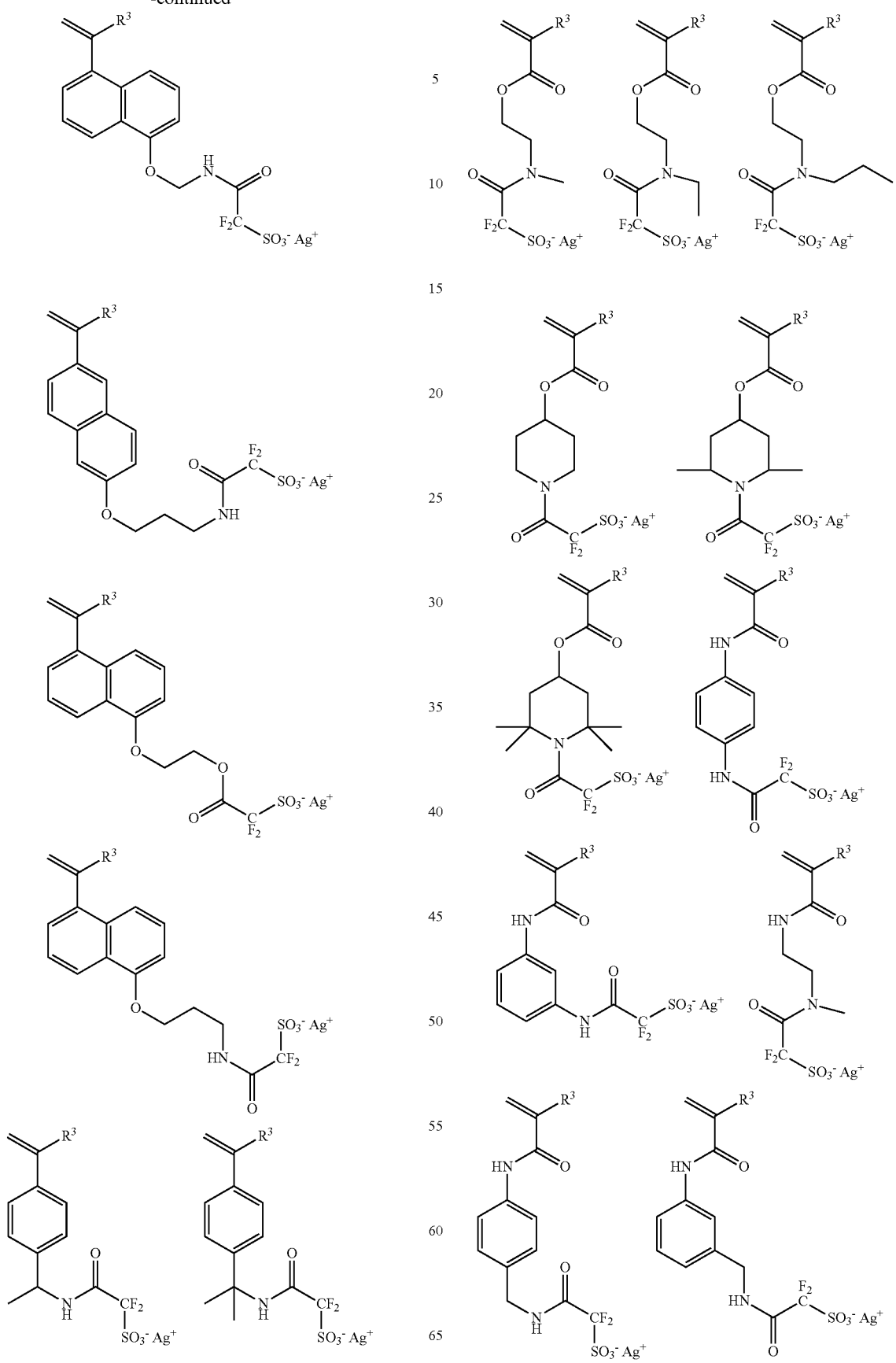

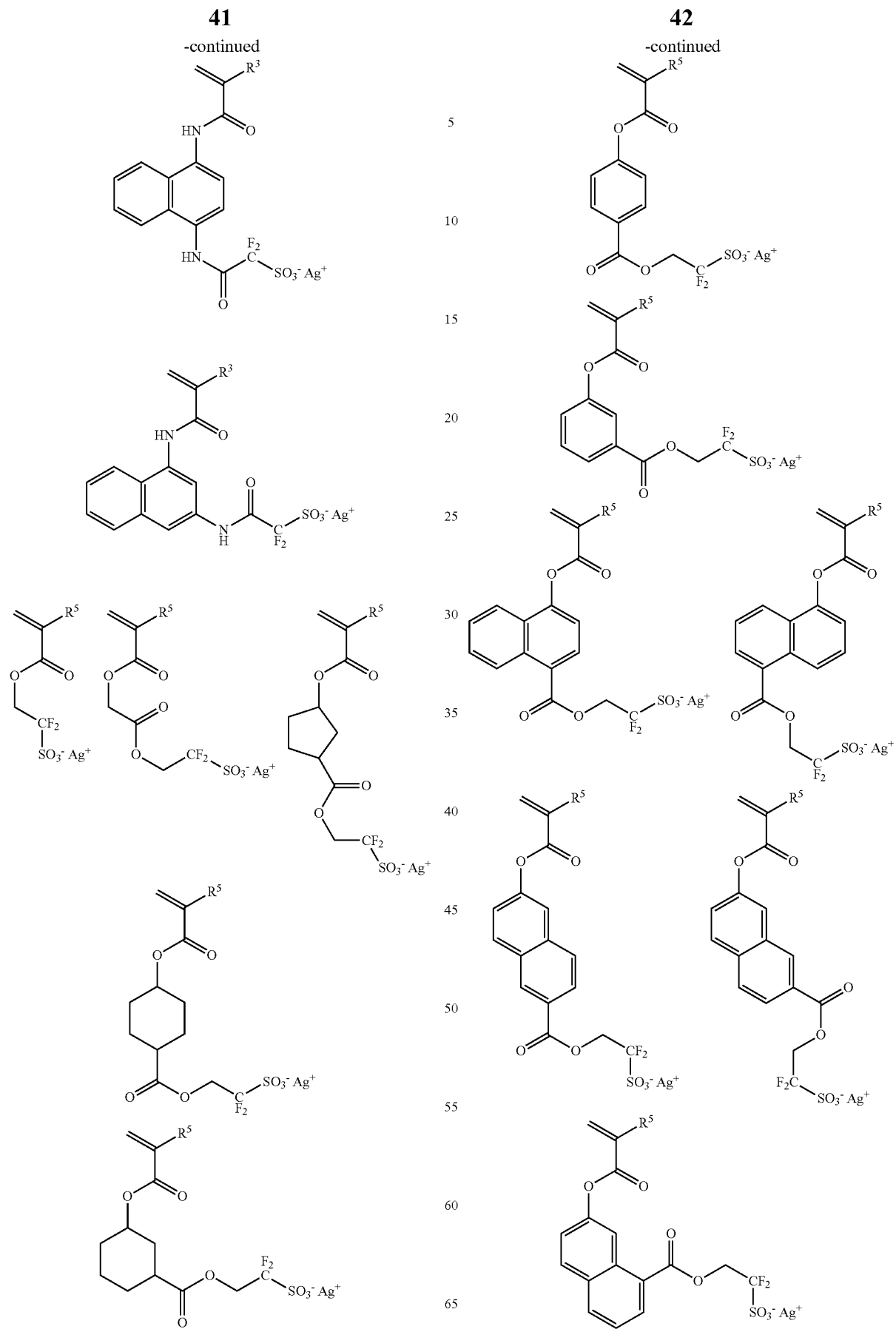

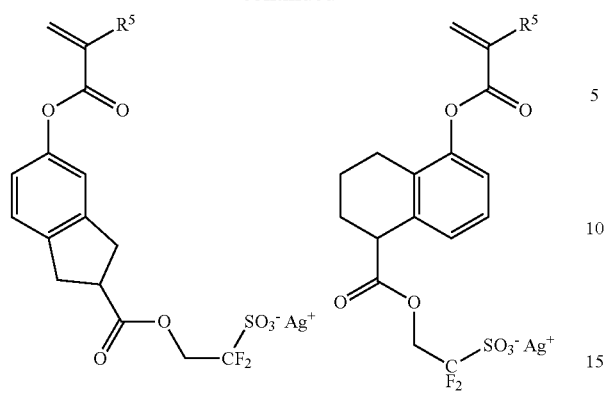
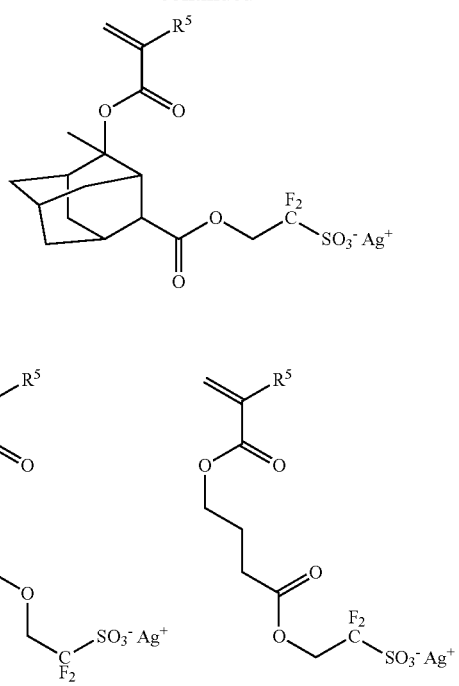
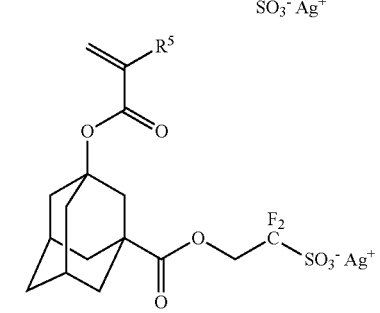
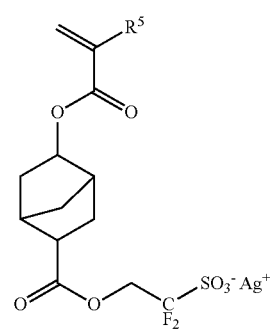
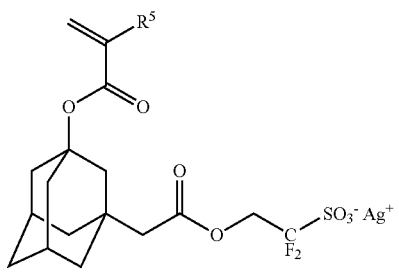
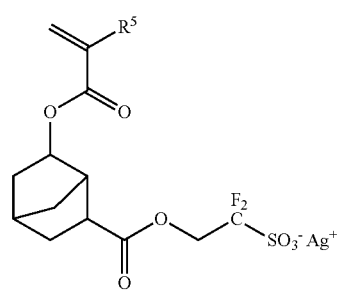
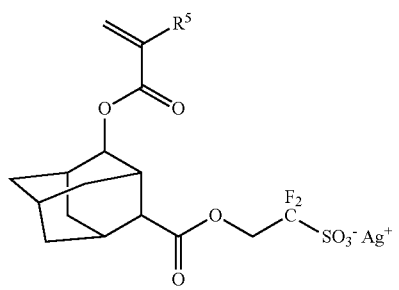
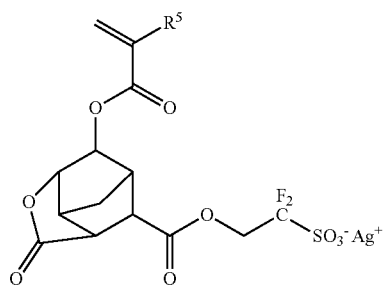

45
-continued
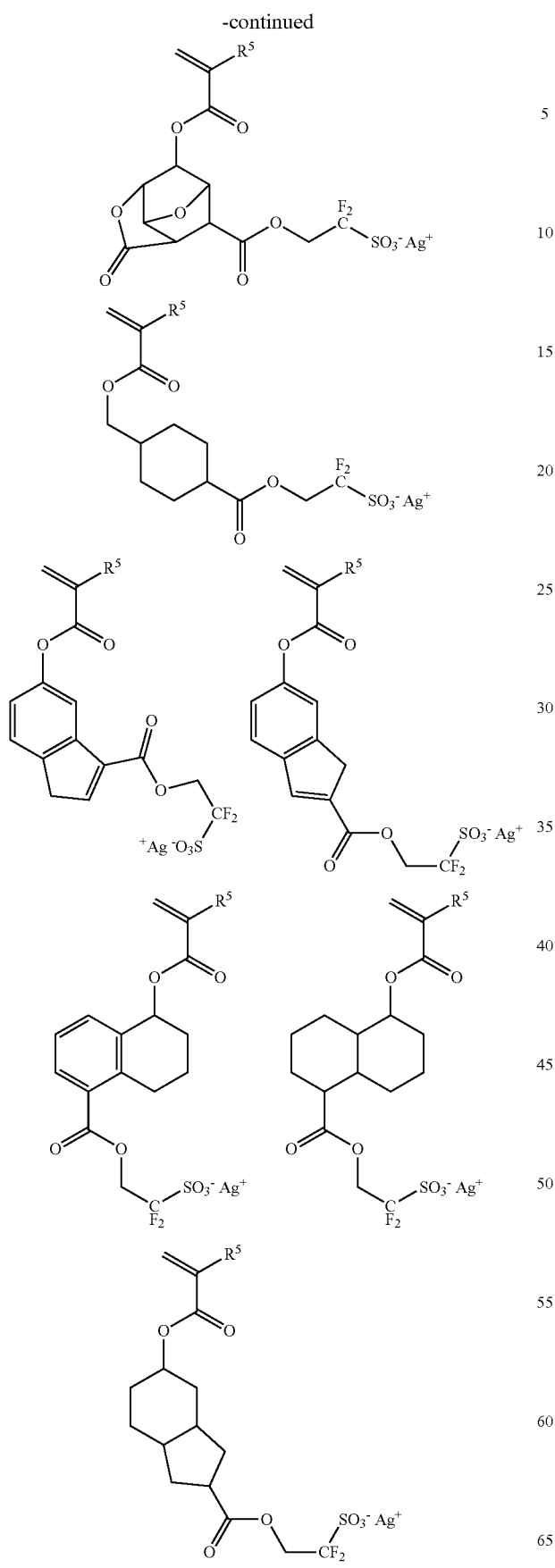
46
-continued
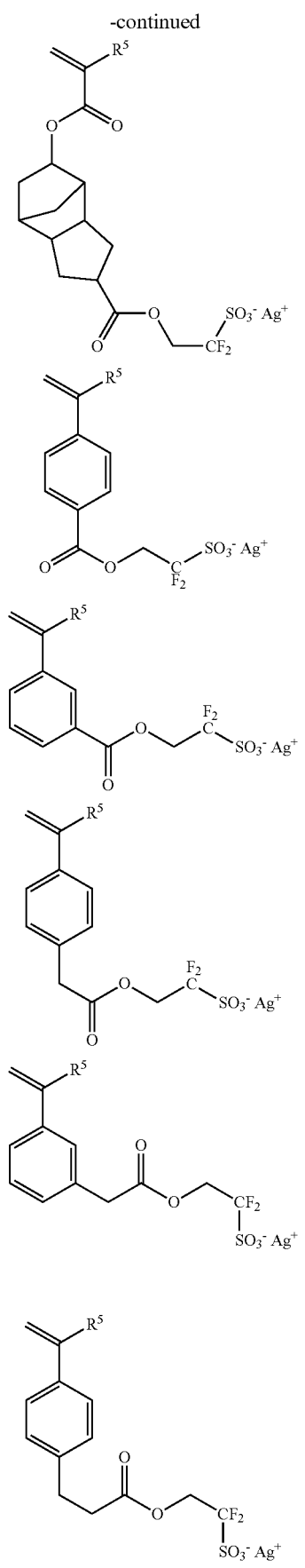

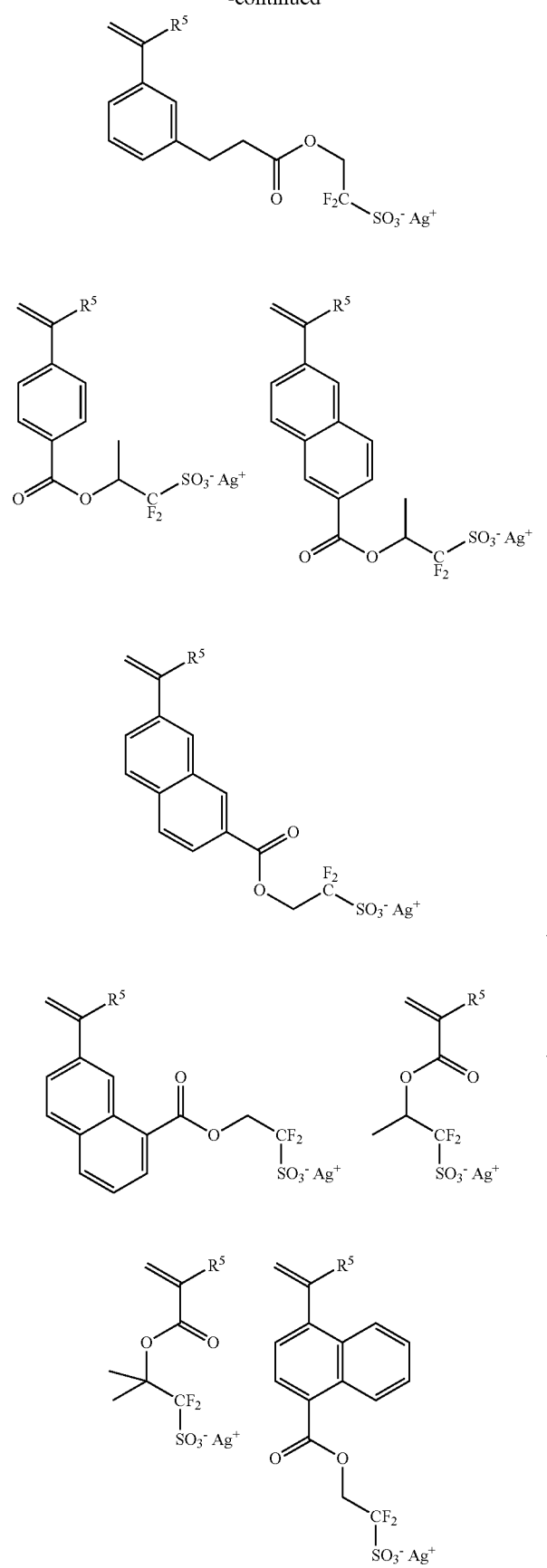

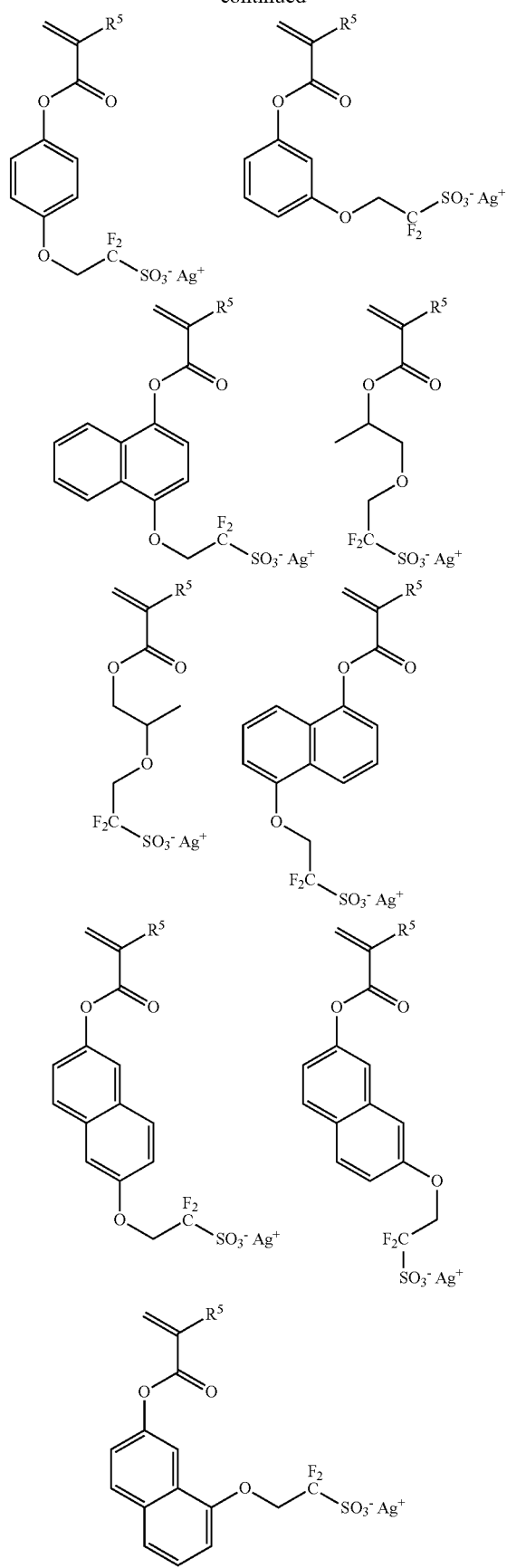
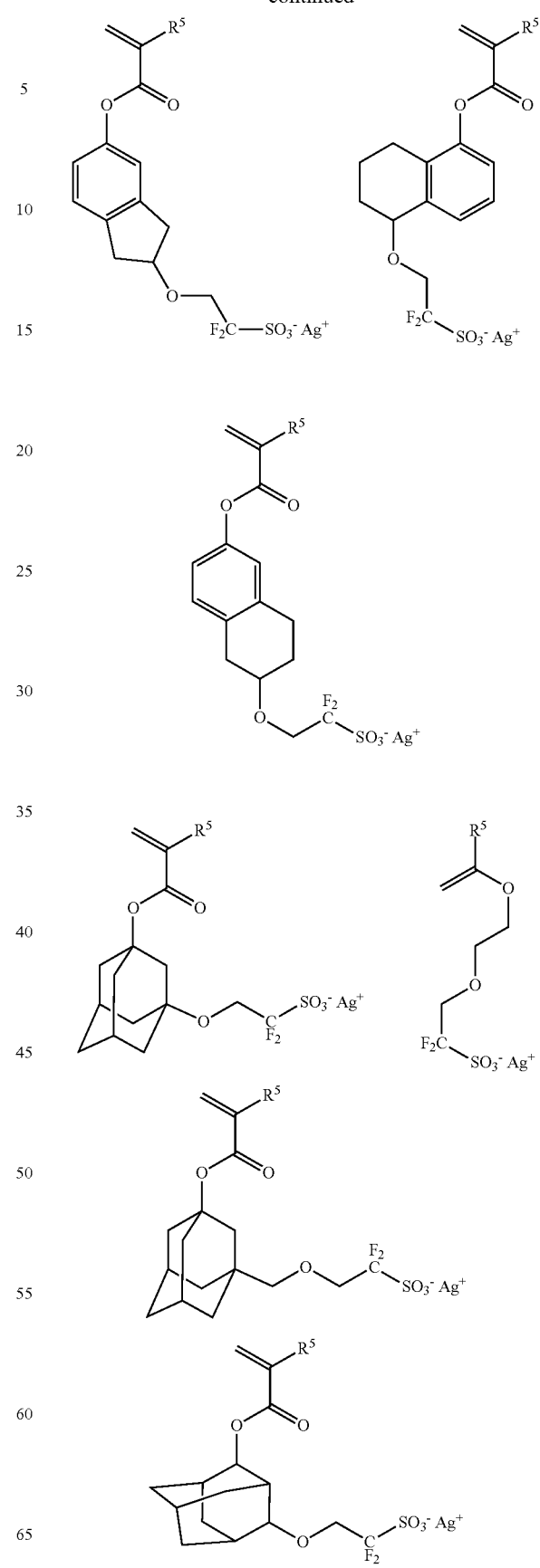

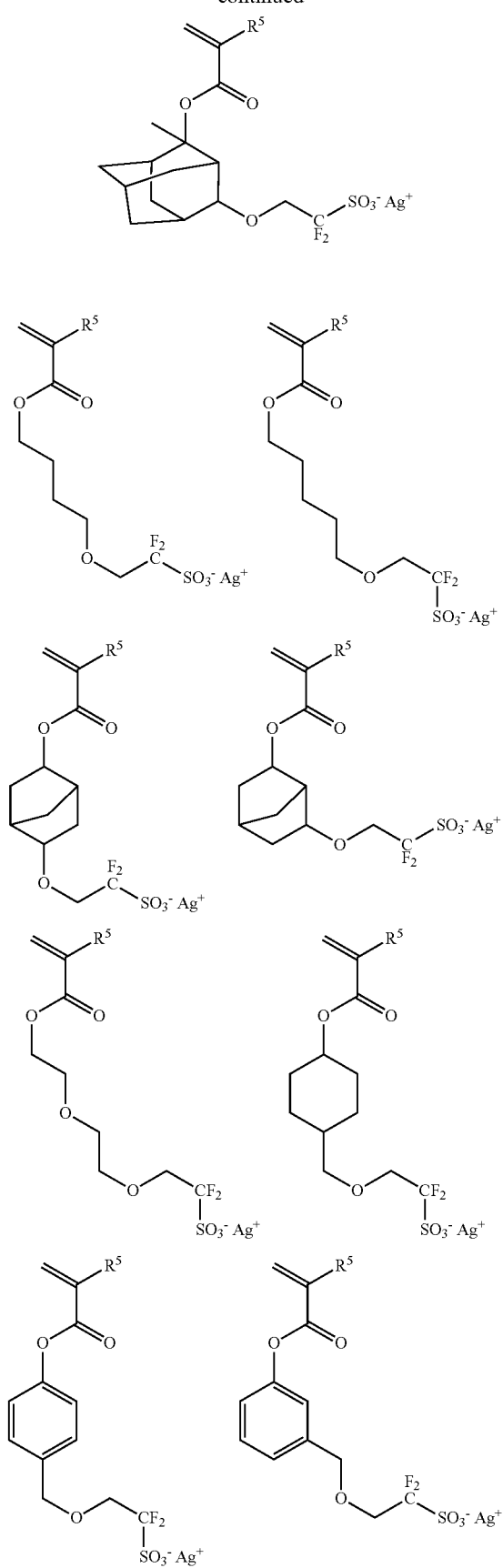
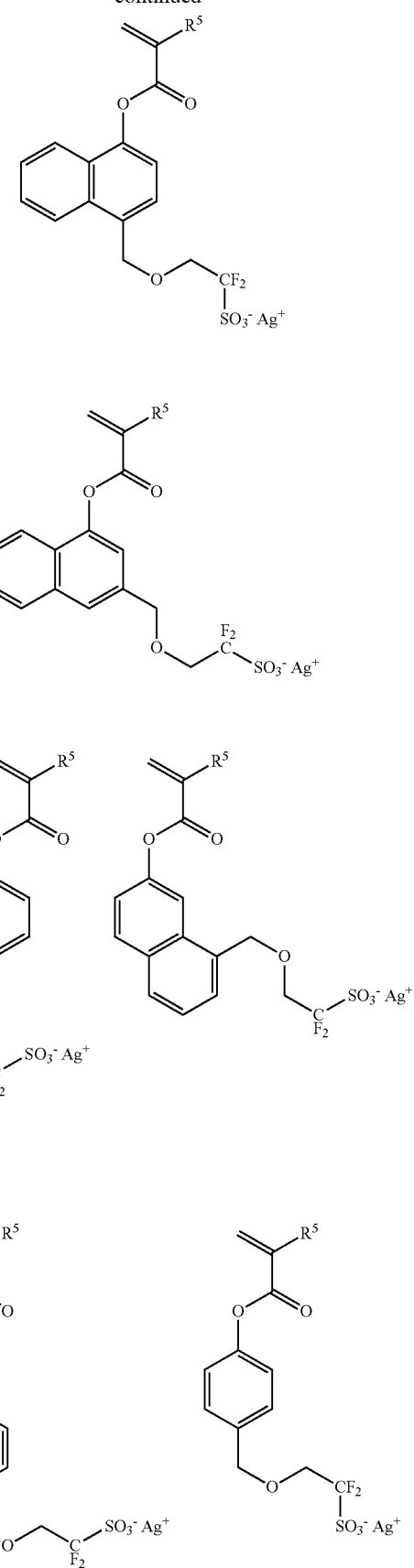

53
-continued
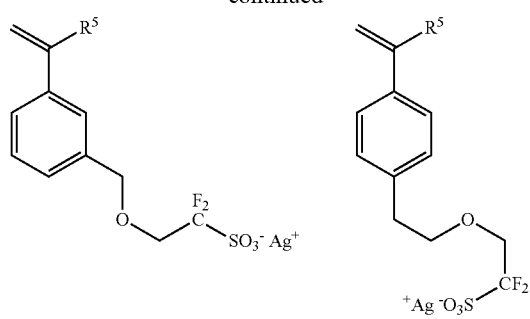
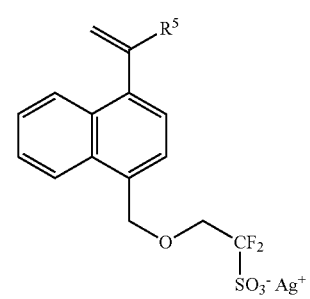
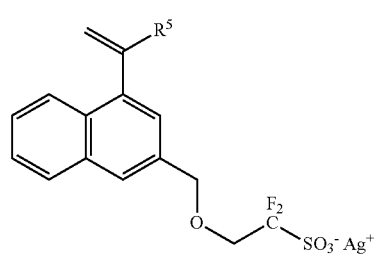
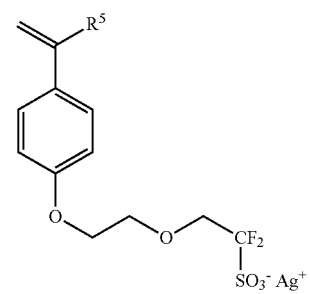
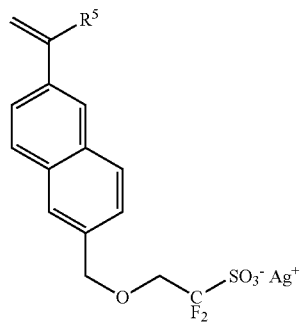
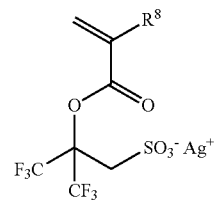
54
-continued
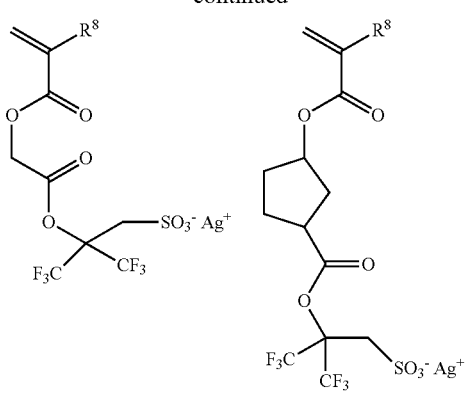
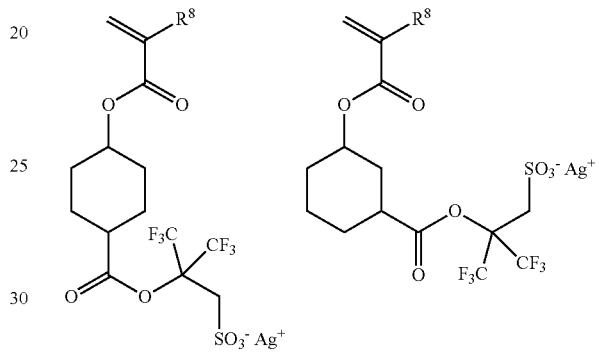
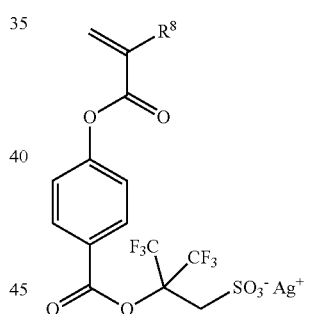
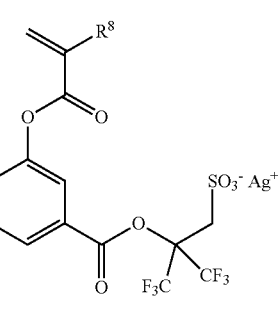
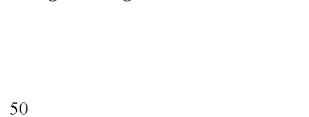
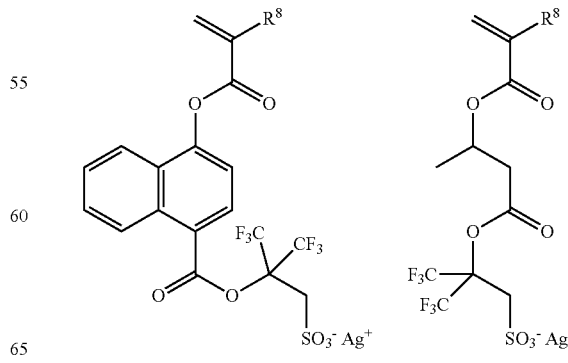

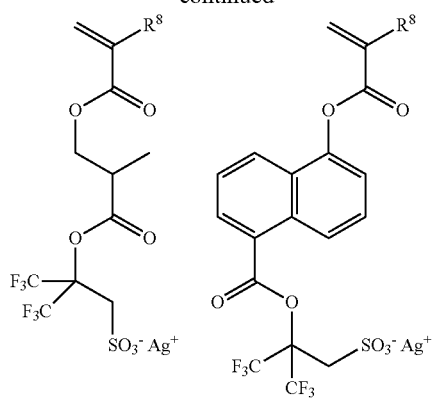
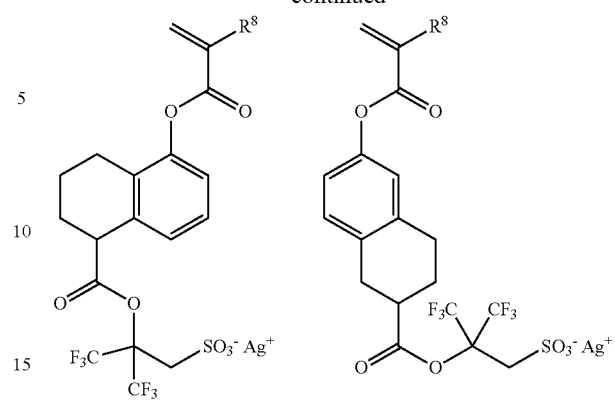
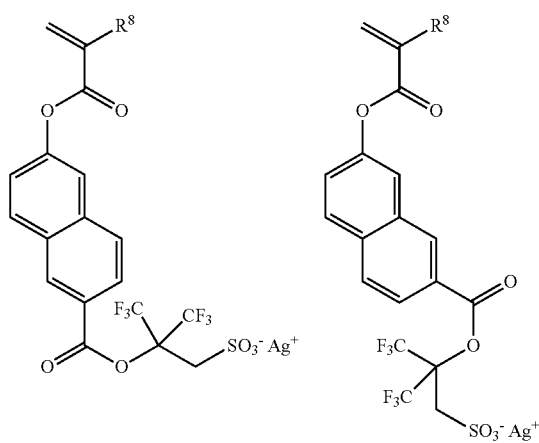
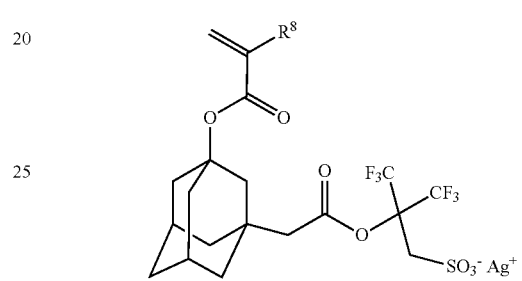
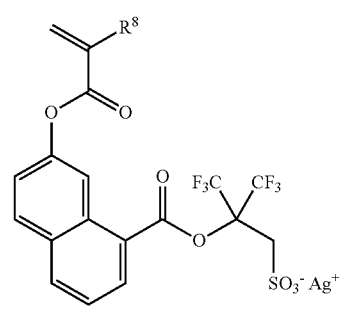
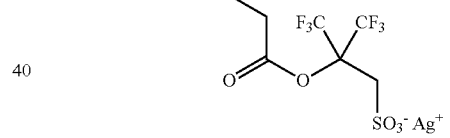
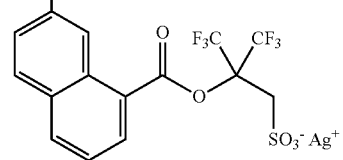
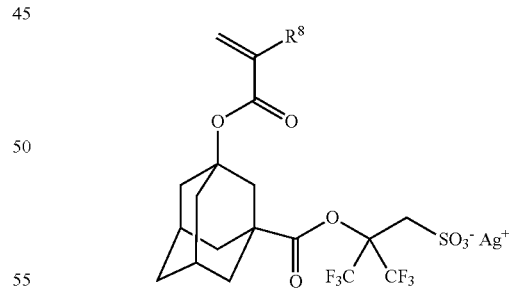
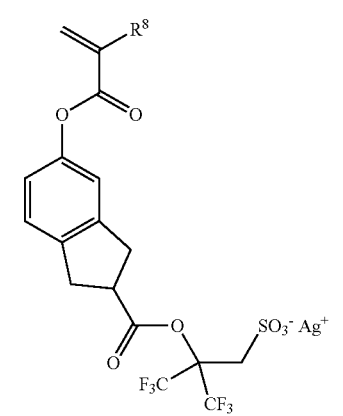
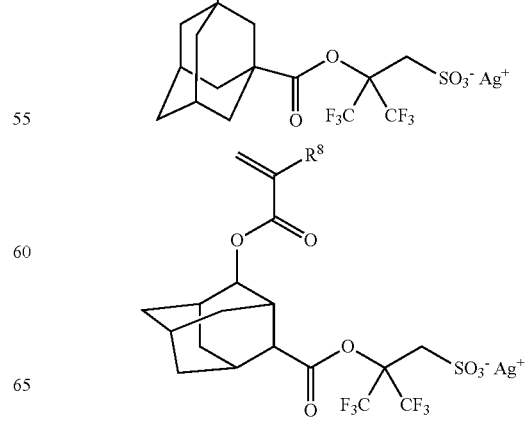

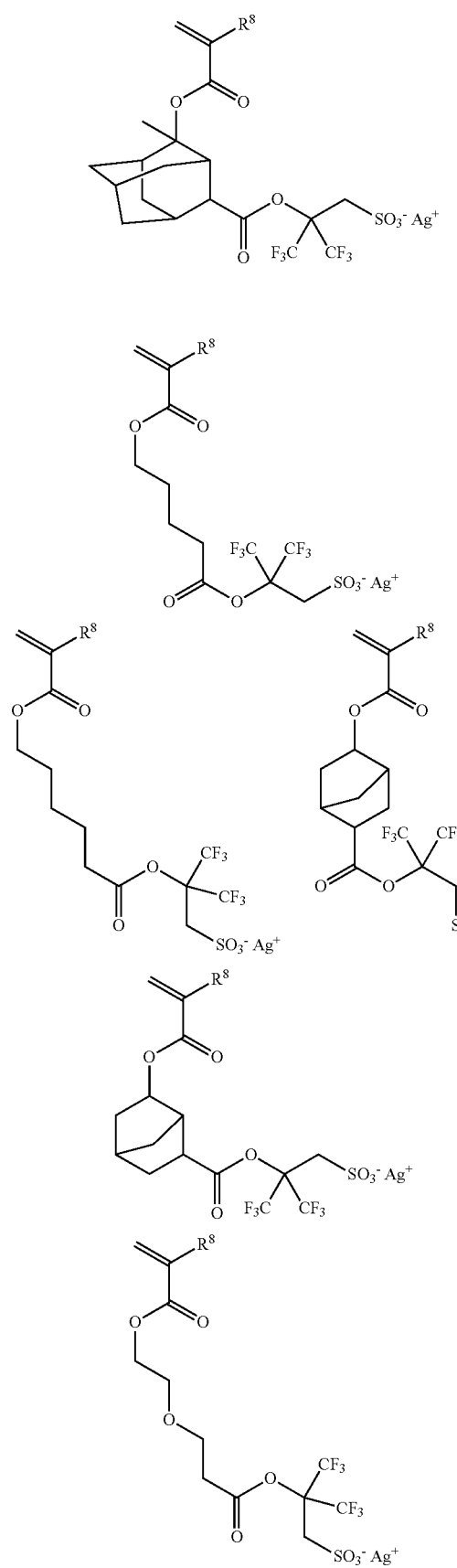
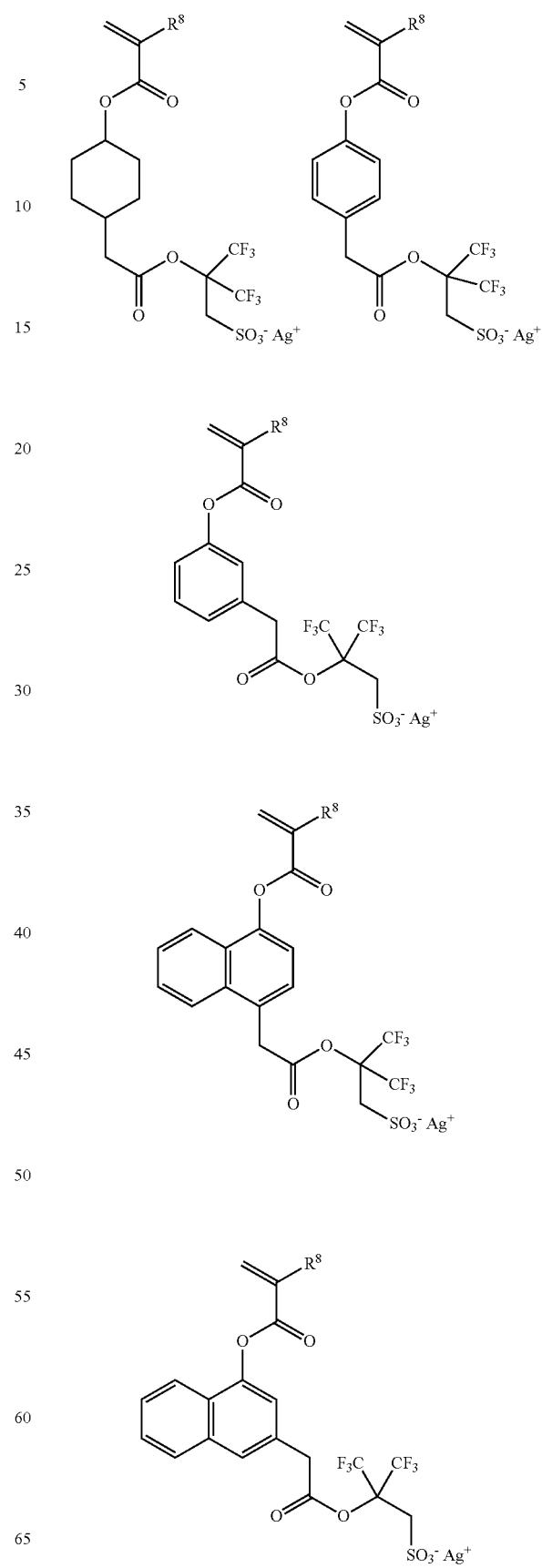

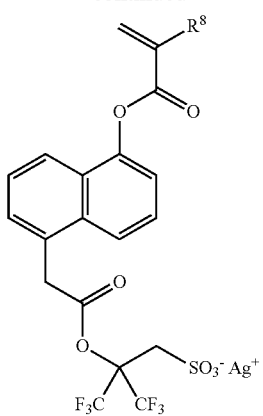
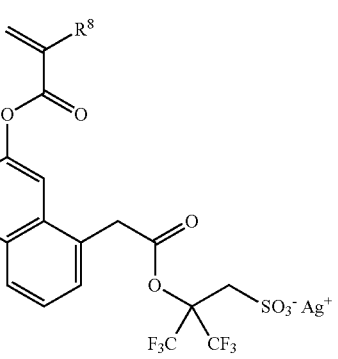
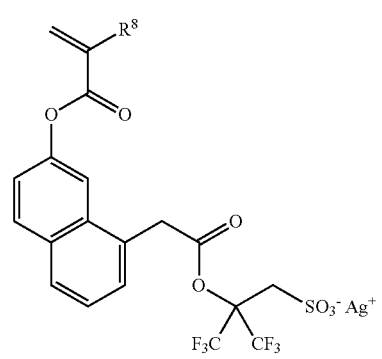
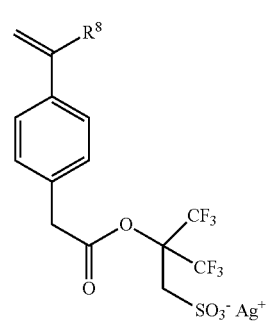
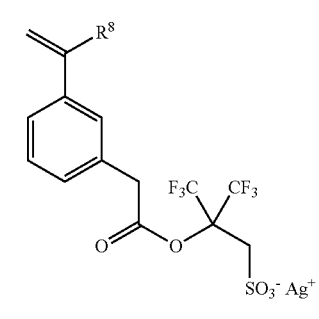
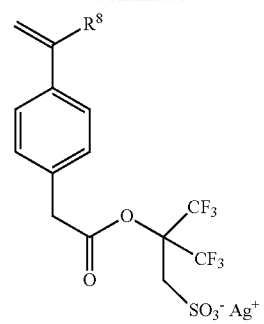
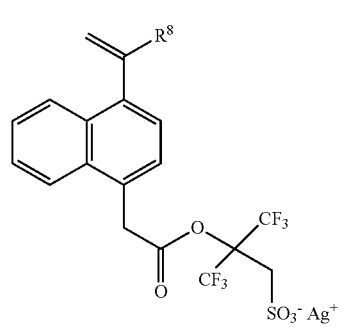
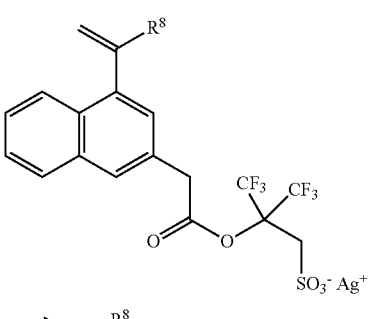
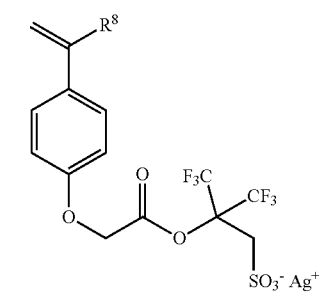
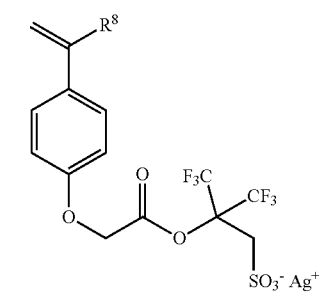

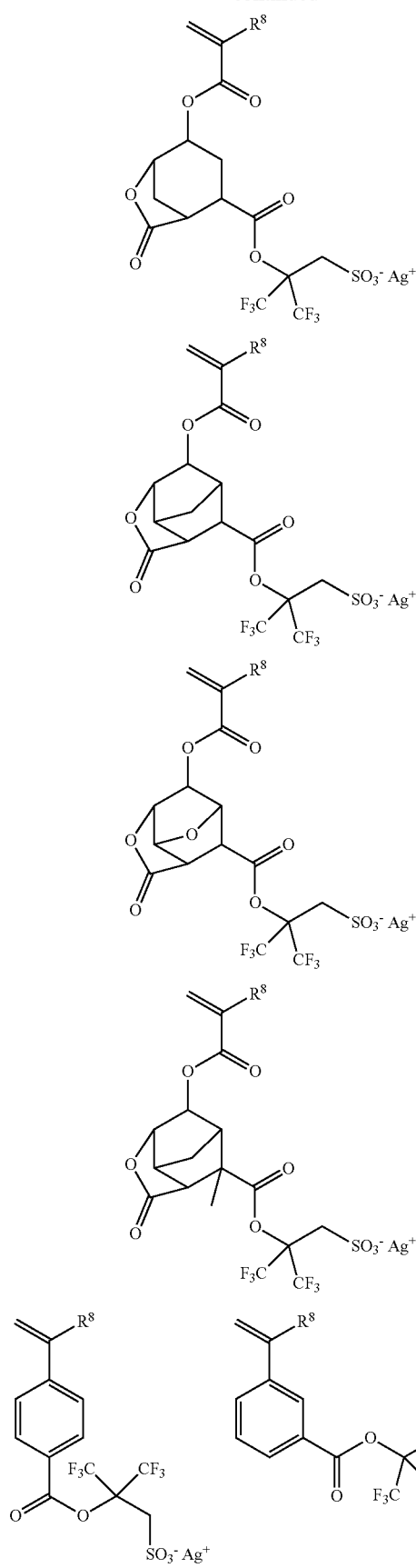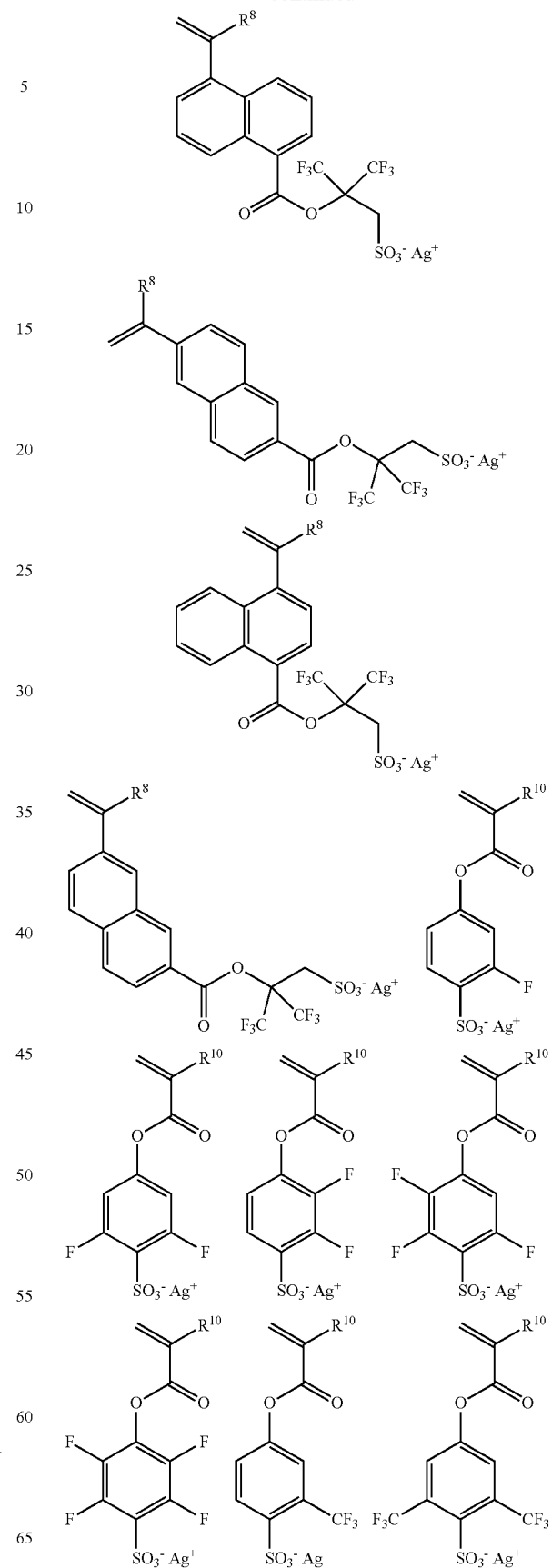

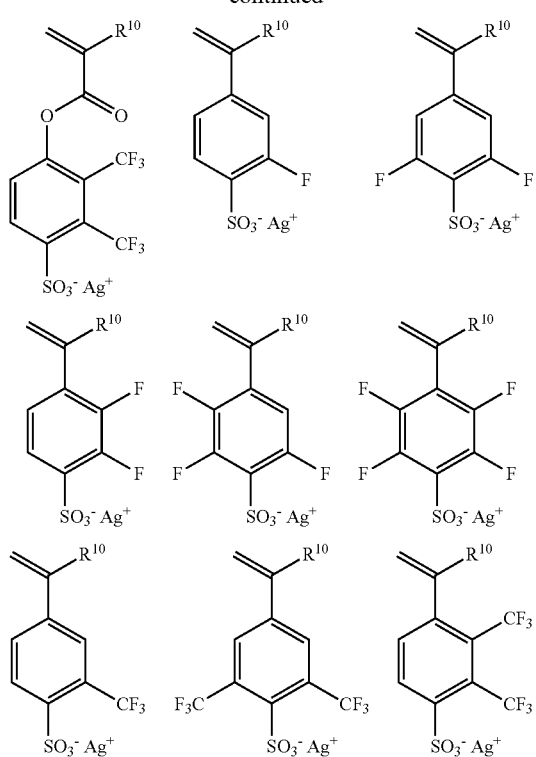
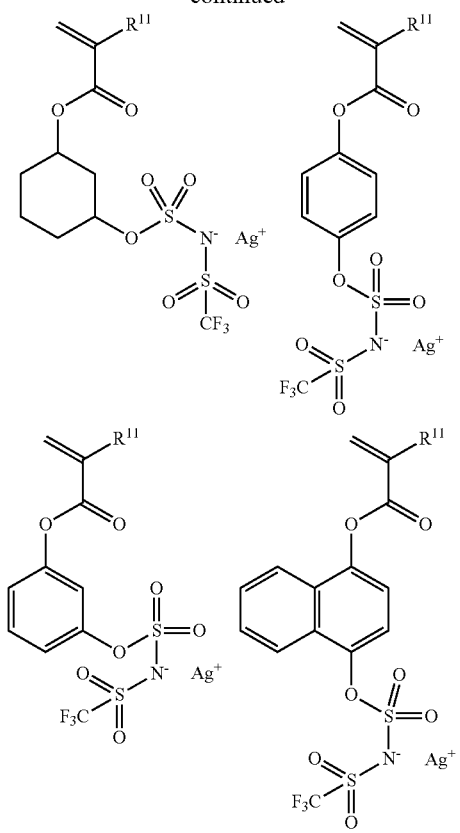
Illustrative examples of sulfonimide salt monomer to give the repeating unit a6 of the above general formula include the following.
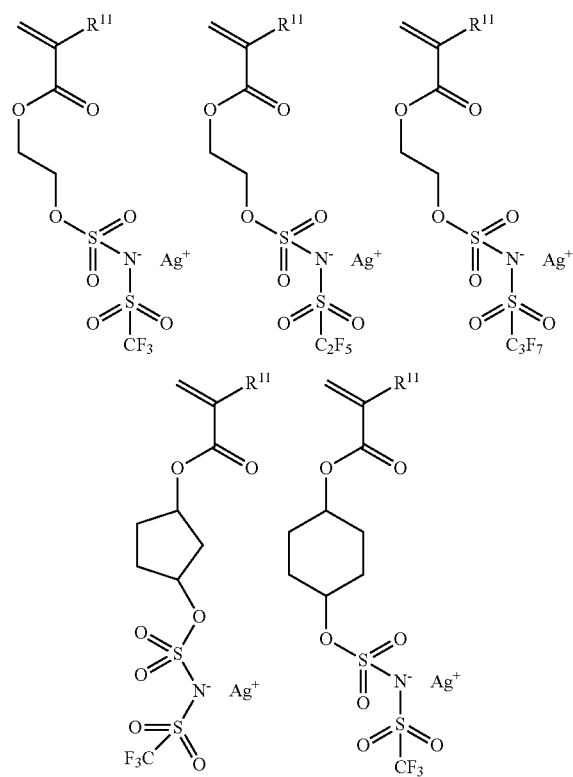
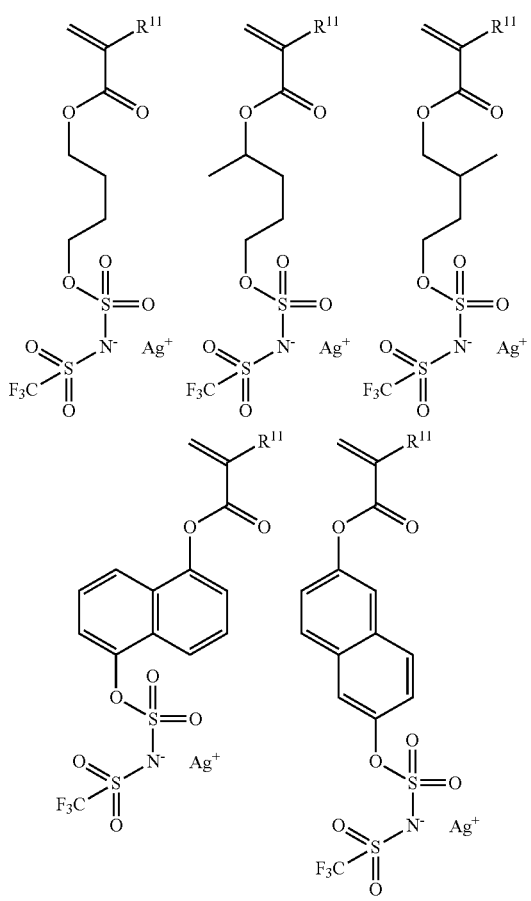

65
-continued
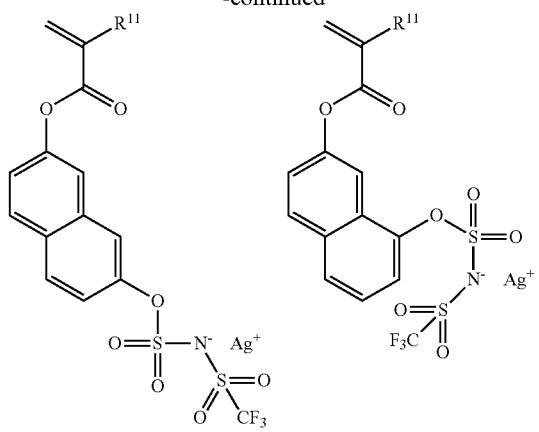
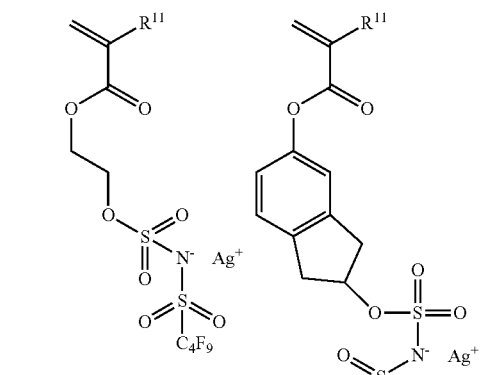
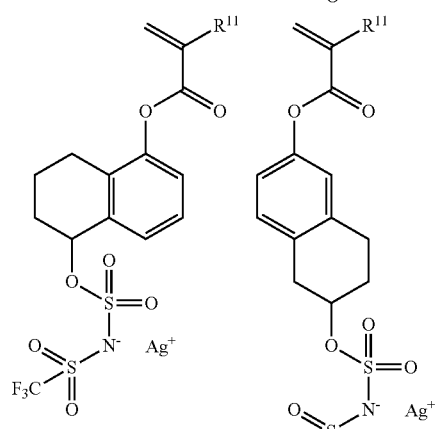
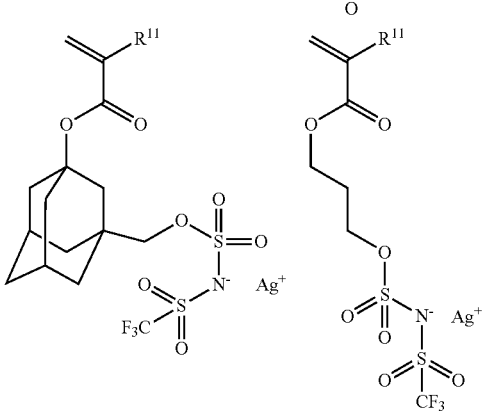
66
-continued
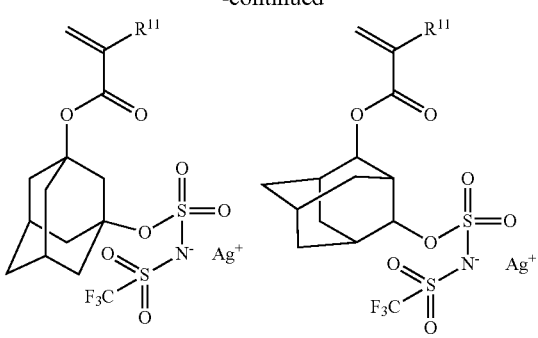
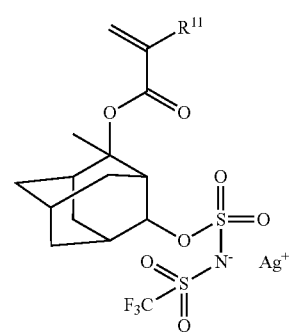
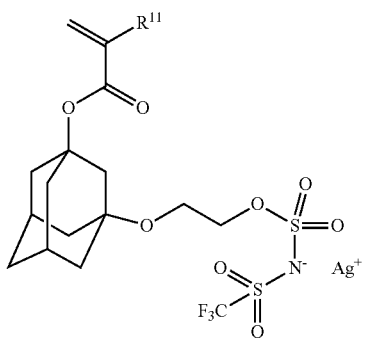
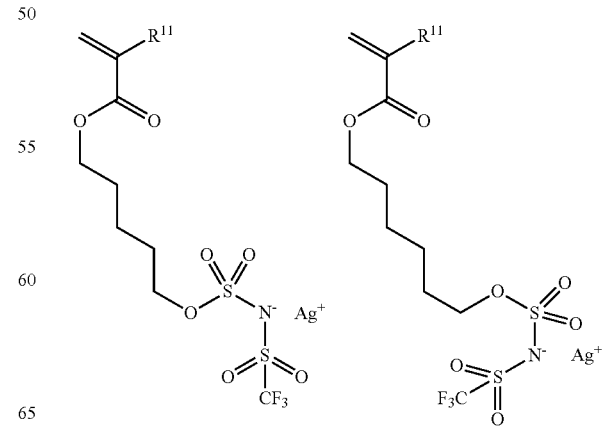

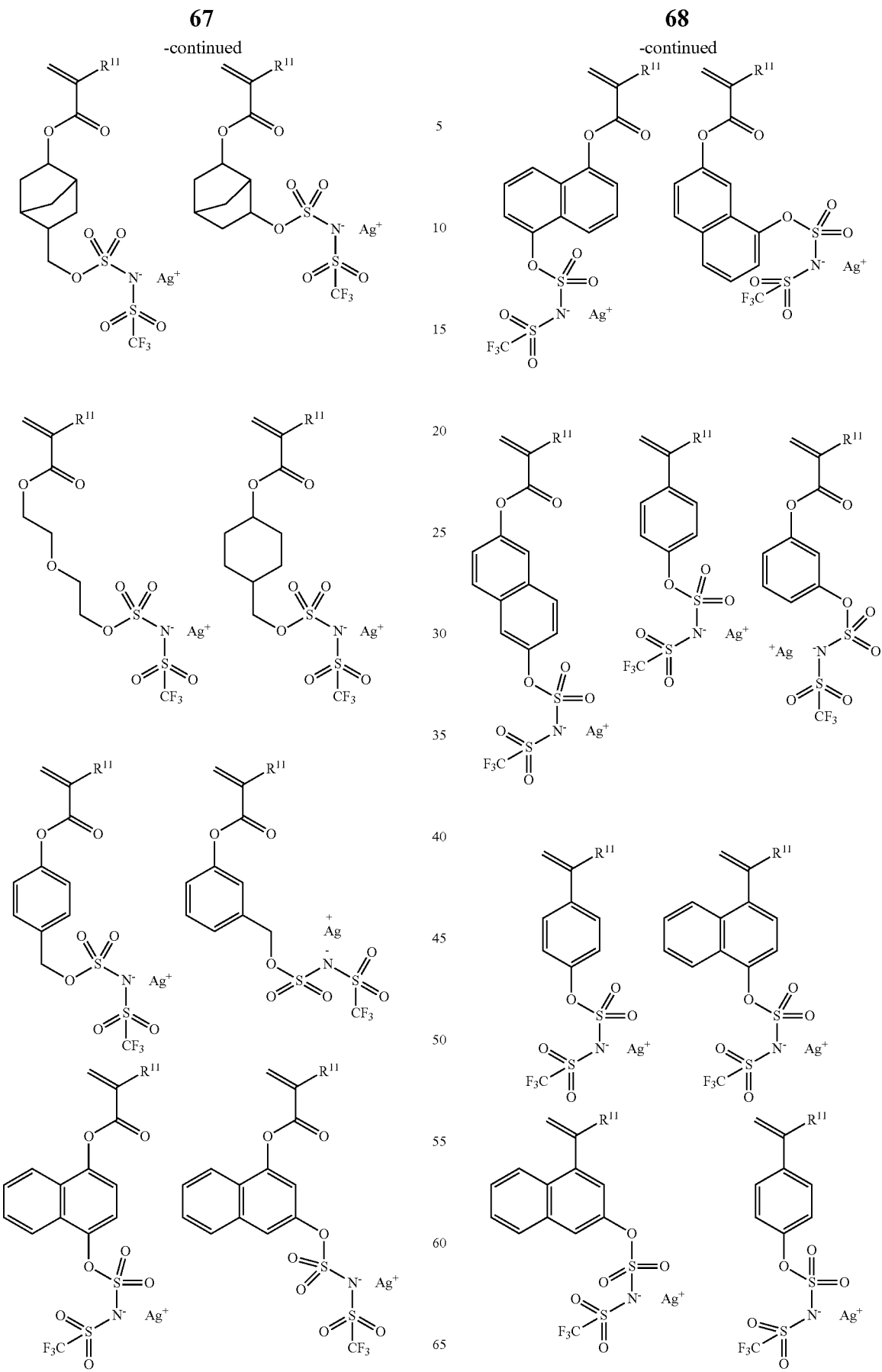

-continued
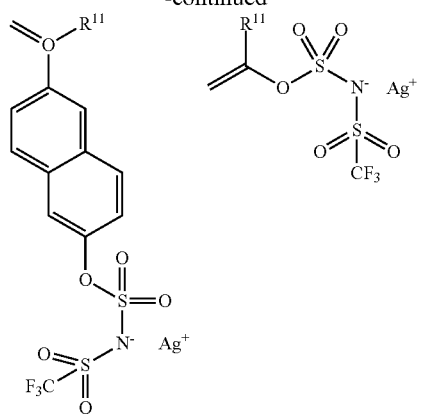
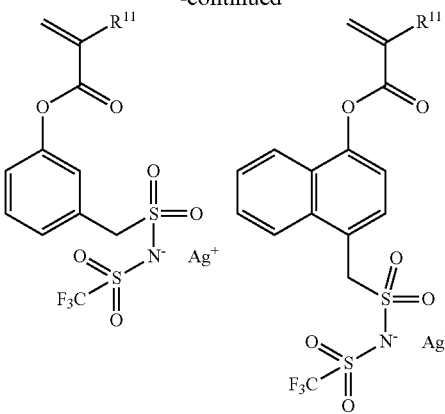
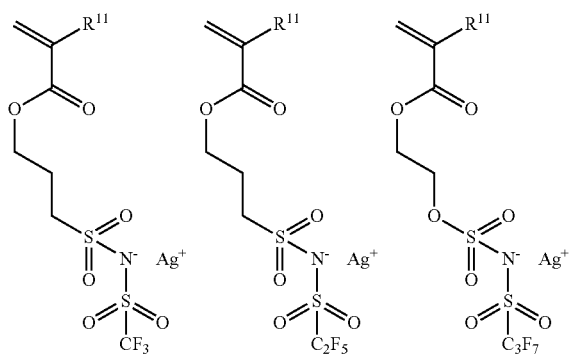
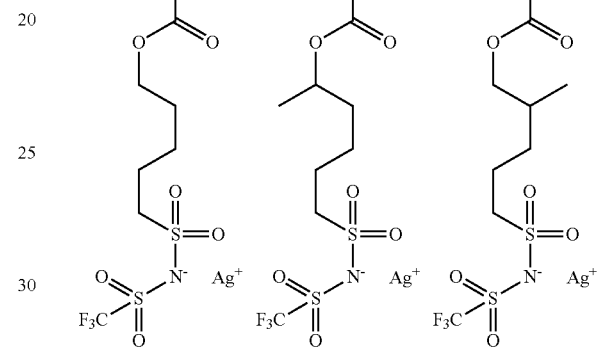
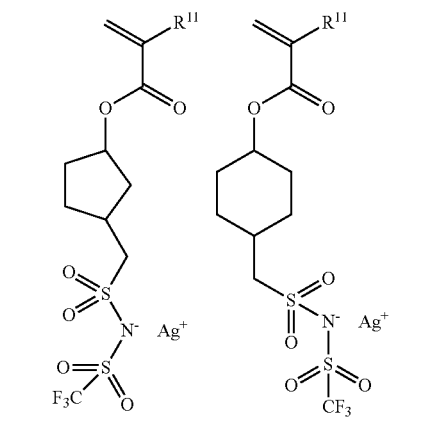
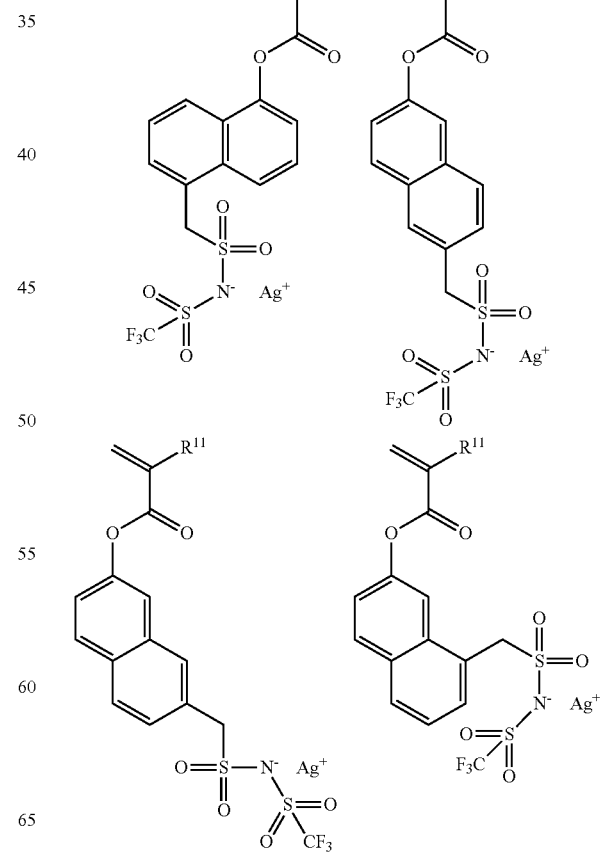
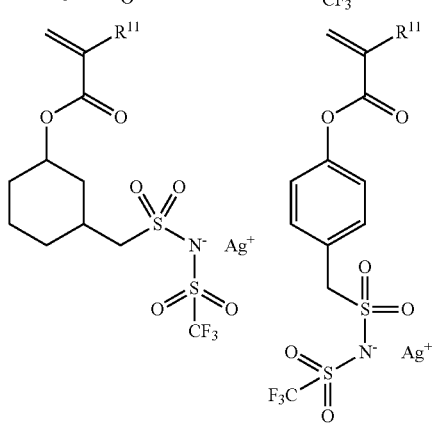

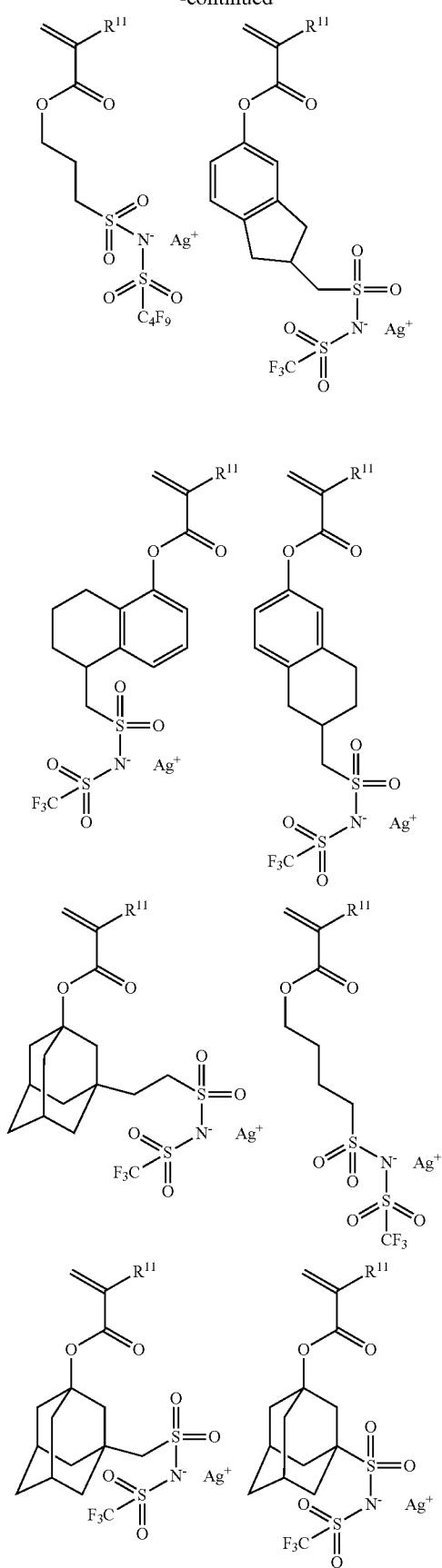
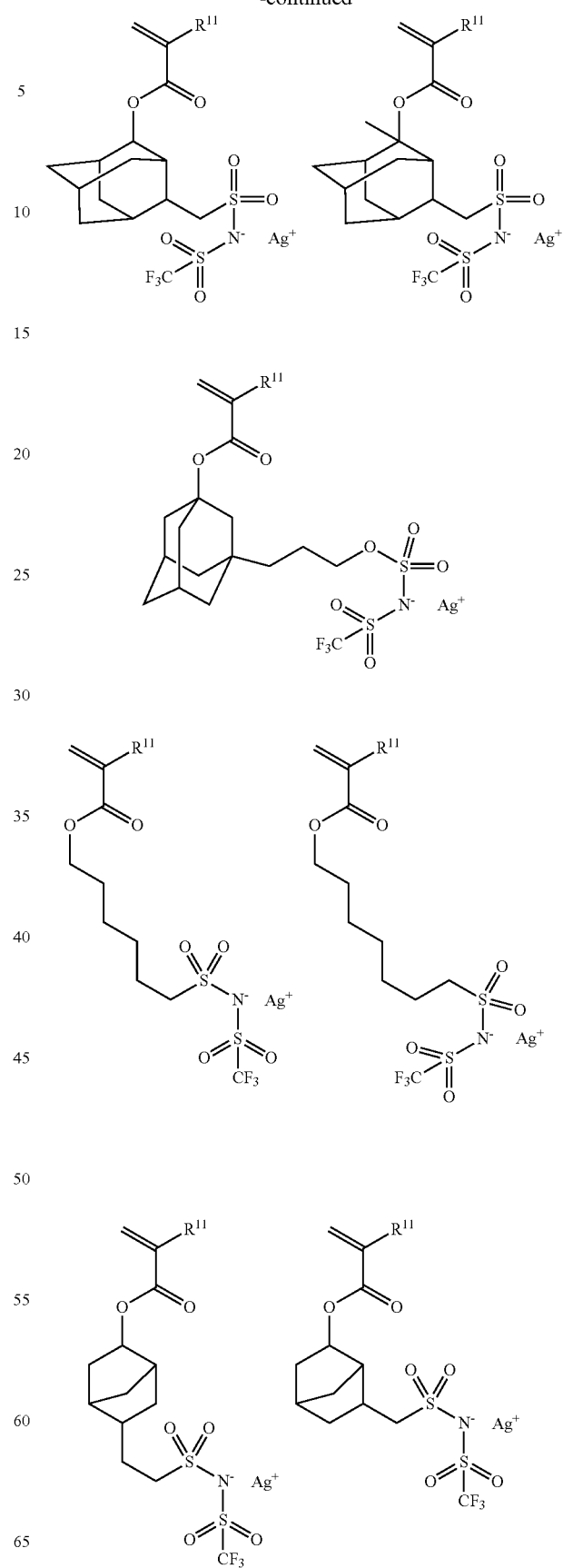

73
-continued
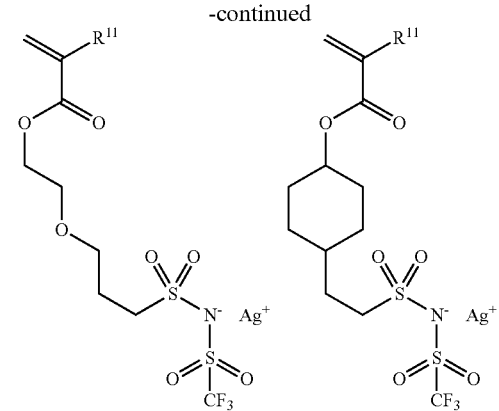
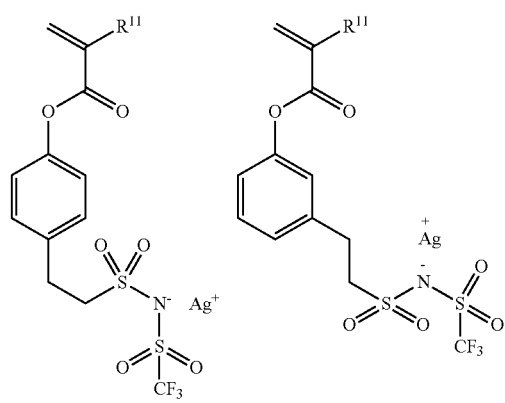
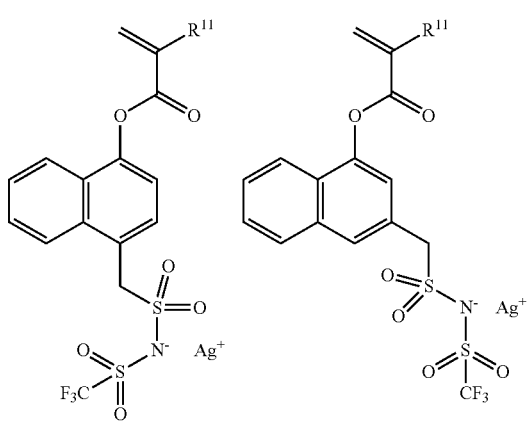
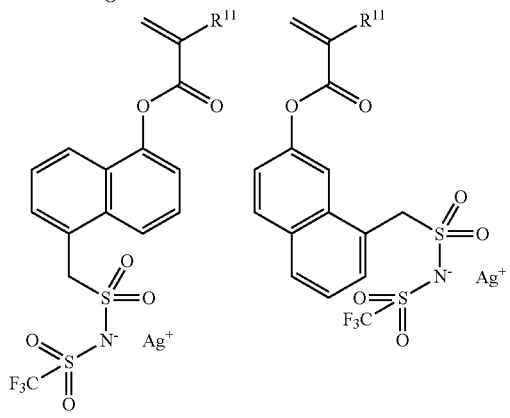
74
-continued
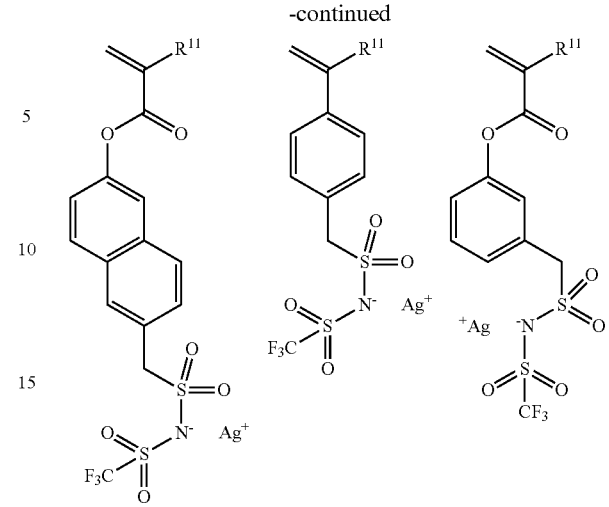
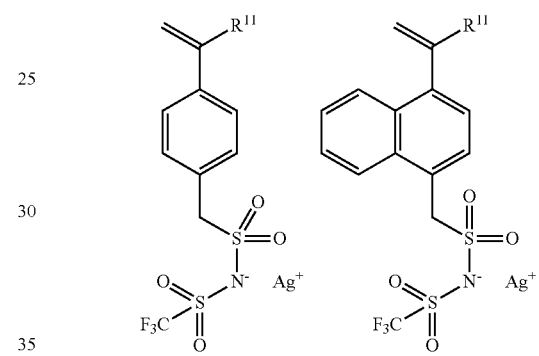
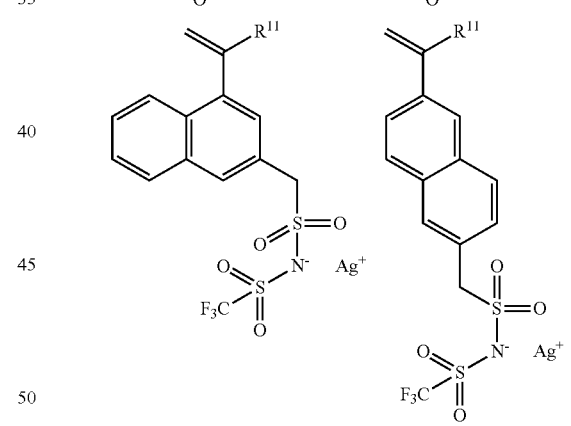
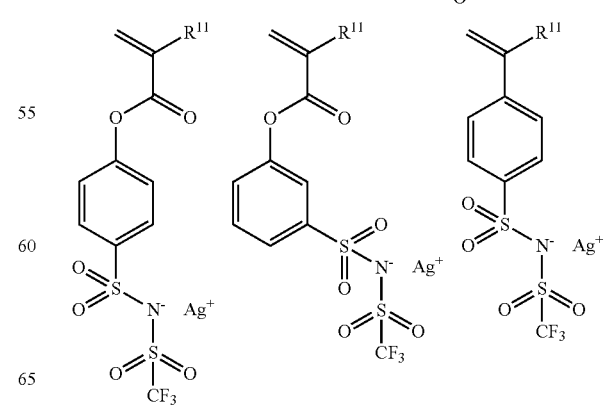

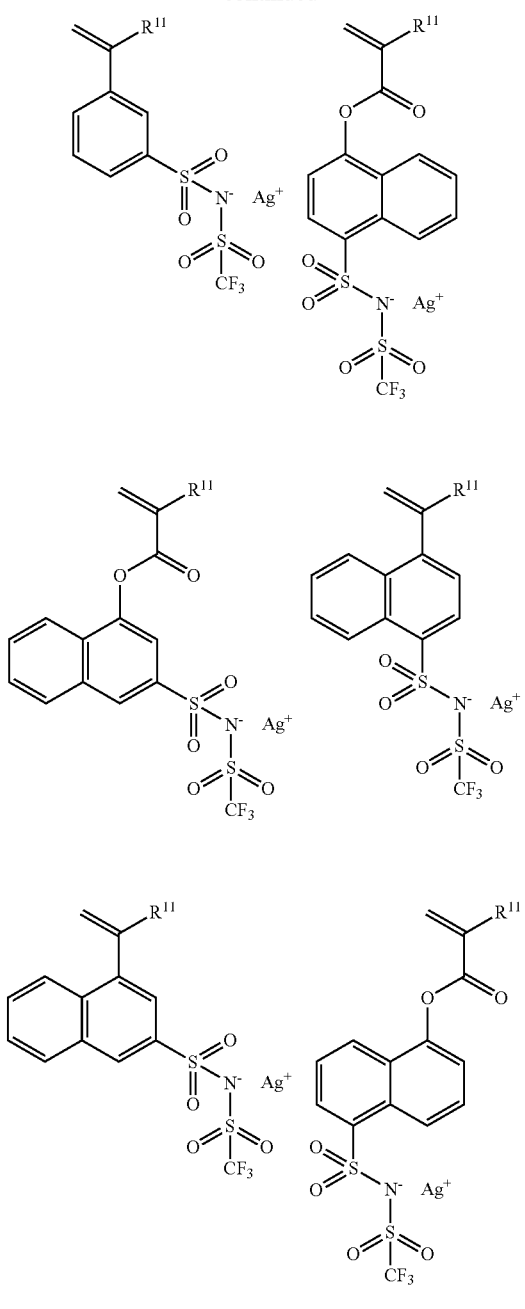
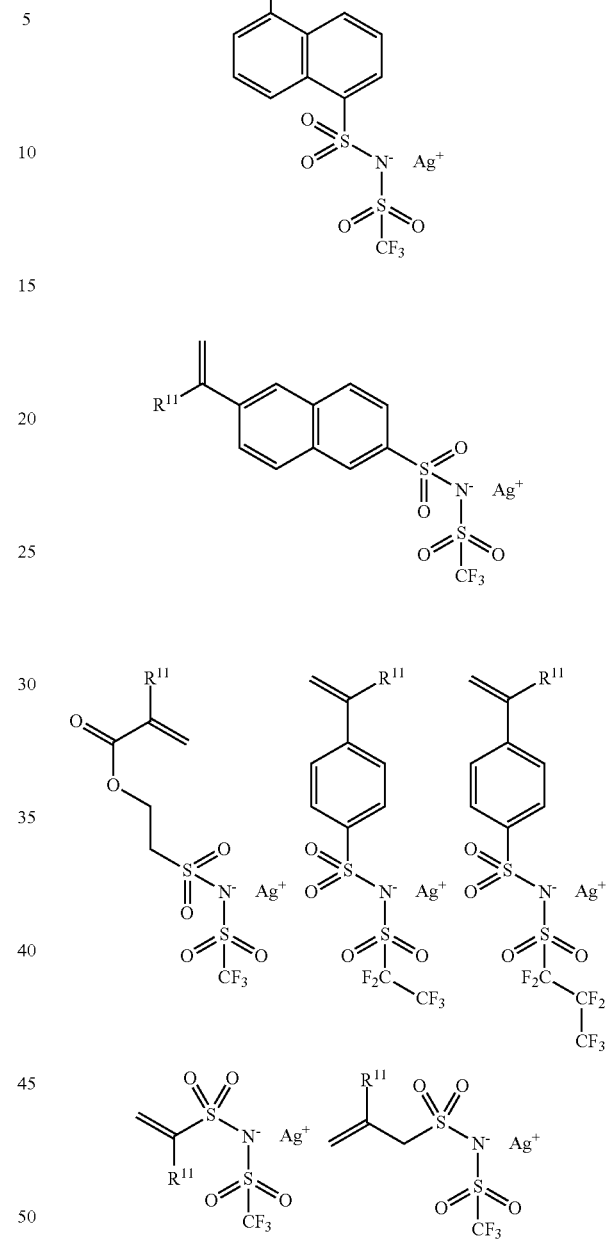
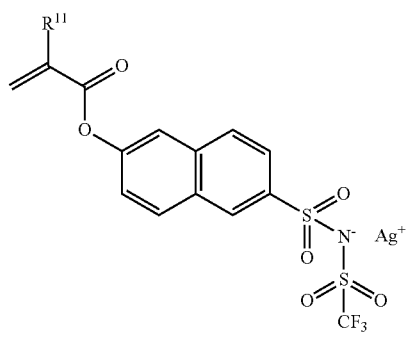
Illustrative examples of sulfonamide salt monomer to give the repeating unit a7 of the above general formula include the following.
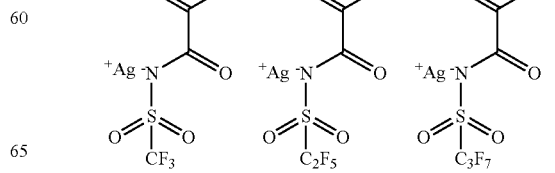

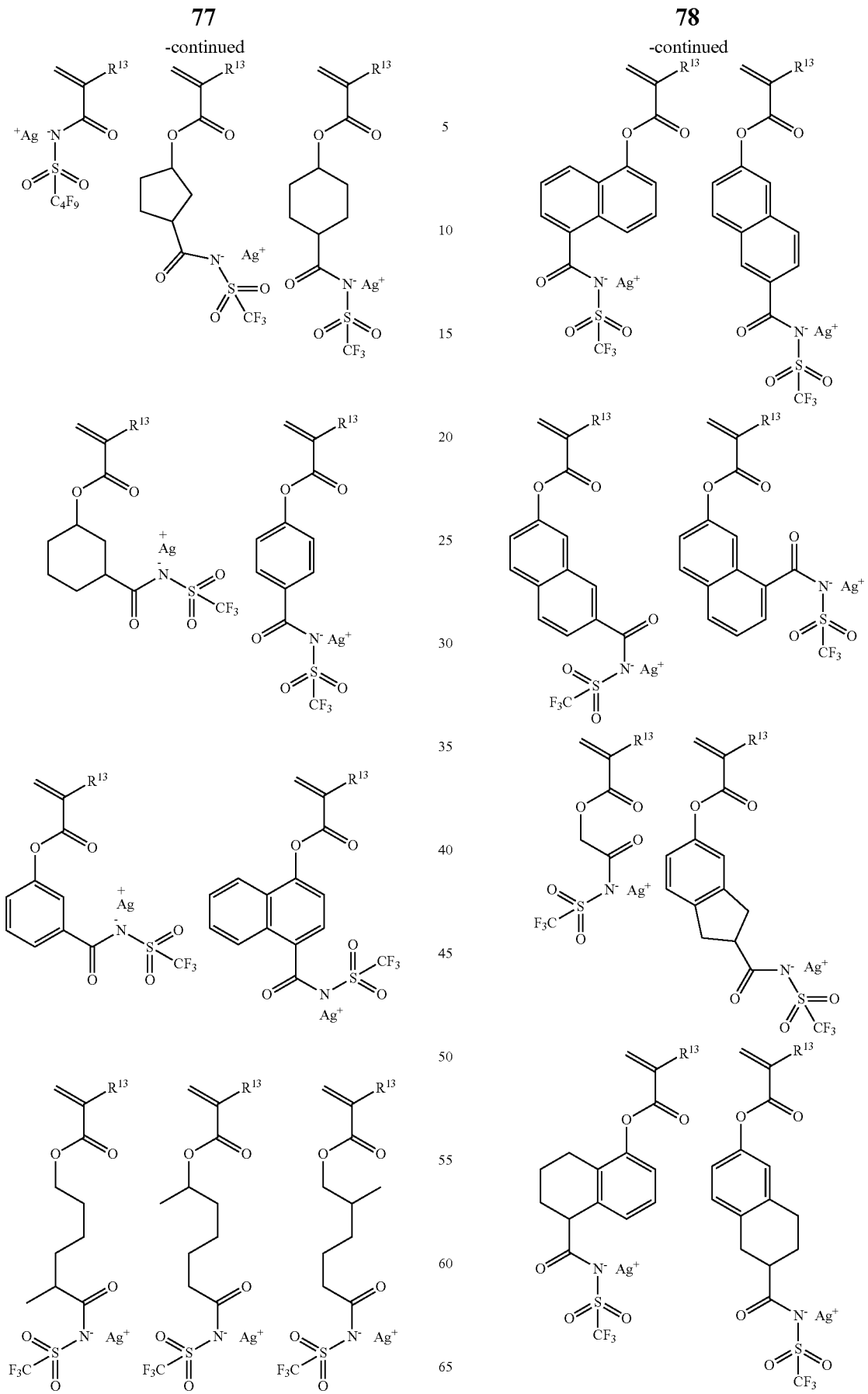

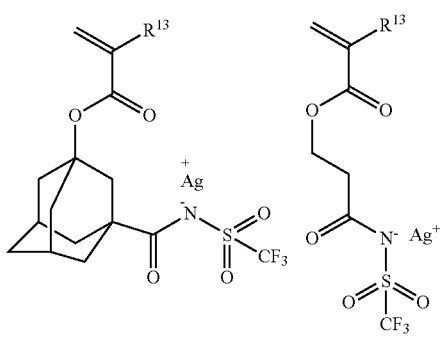
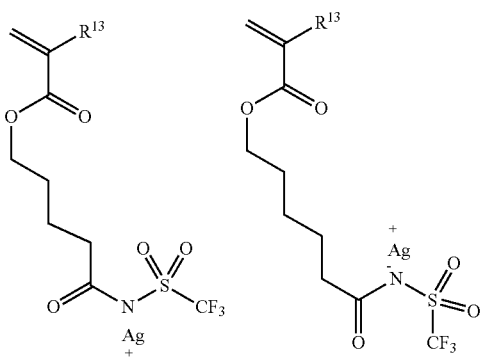
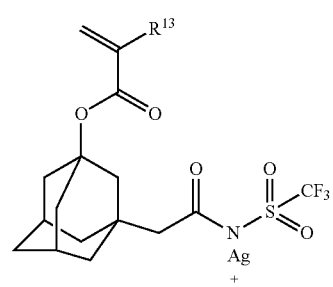
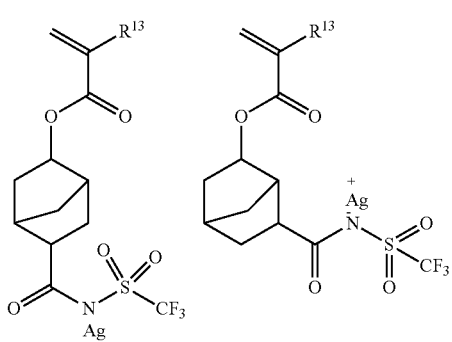
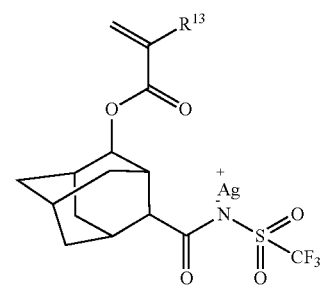
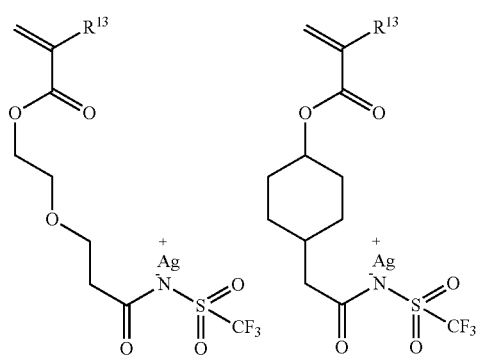
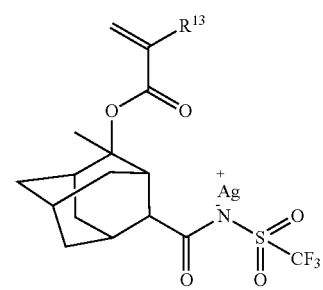
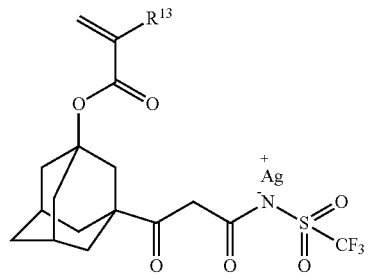
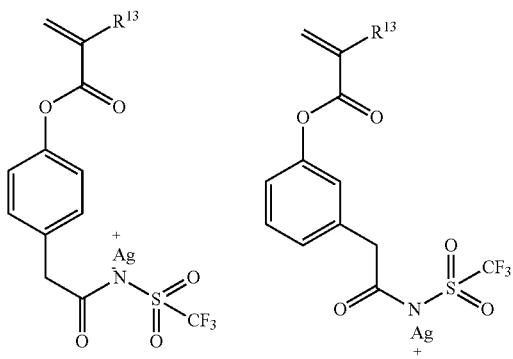

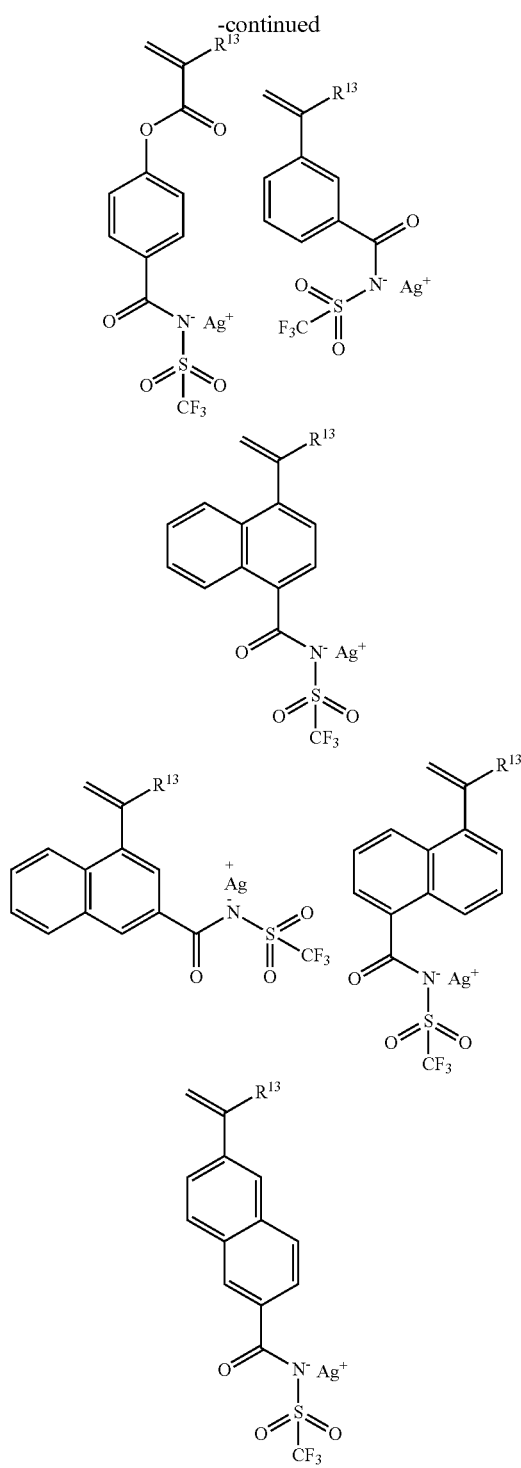

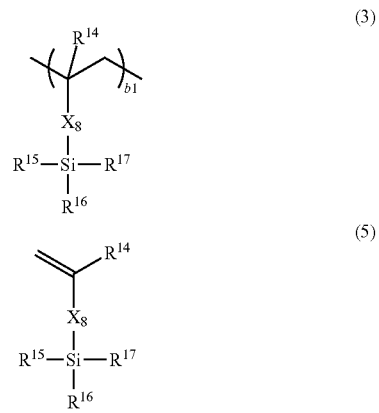

(Repeating Unit-b)

The component (A) of the inventive bio-electrode composition contains a repeating unit-b having silicon in addition to the repeating unit-a.

As the repeating unit-b, it is preferable to contain a repeating unit-b1 shown by the following general formula (3). The monomer to give the repeating unit-b1 in the general formula (3) is shown by the following general formula (5), $$\text{(3)}$$

$$\text{(5)}$$

wherein $R^{14}$ represents a hydrogen atom or a methyl group; $X_8$ represents an arylene group having 6 to 12 carbon atoms, a $—C(=O)—O—R^{18}—$ group, or a $—C(=O)—NH—R^{18}—$ group; $R^{18}$ represents any of a single bond, a linear, branched, or cyclic alkylene group having 2 to 12 carbon atoms, and a phenylene group, optionally having one or more groups selected from an ether group, a carbonyl group, an ester group, and an amide group; $R^{15}$, $R^{16}$, and $R^{17}$ each represent a linear, branched, or cyclic alkyl group having 1 to 21 carbon atoms or an aryl group having 6 to 10 carbon atoms, optionally having one or more species selected from a siloxane bond, a silicon atom, and a halogen atom; $R^{15}$ and $R^{16}$, or $R^{15}$, $R^{16}$, and $R^{17}$ are optionally bonded to each other to form a ring or a three dimensional structure; and b1 is a number satisfying 0<b1<1.0.

Illustrative examples of the monomer shown by the general formula (5) include the following.

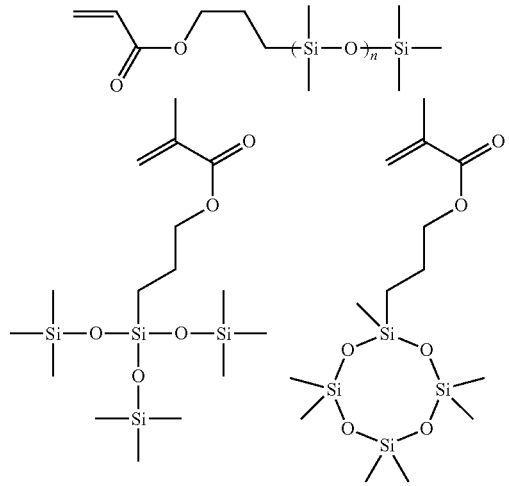

In the formulae, $R^1$, $R^3$, $R^5$, $R^8$, $R^{10}$, $R^{11}$, and $R^{13}$ each have the meaning described above.

As a method for synthesizing a silver salt monomer for obtaining the repeating units a1 to a7 shown by the general formulae (2), they can be obtained by a method of mixing silver chloride with an ammonium salt composed of the fluorosulfonic anion, fluoroimidic anion, or fluoroamidic anion described above and an ammonium cation in an organic solvent. In this case, ammonium chloride, formed as a bi-product, is preferably removed by washing with water.

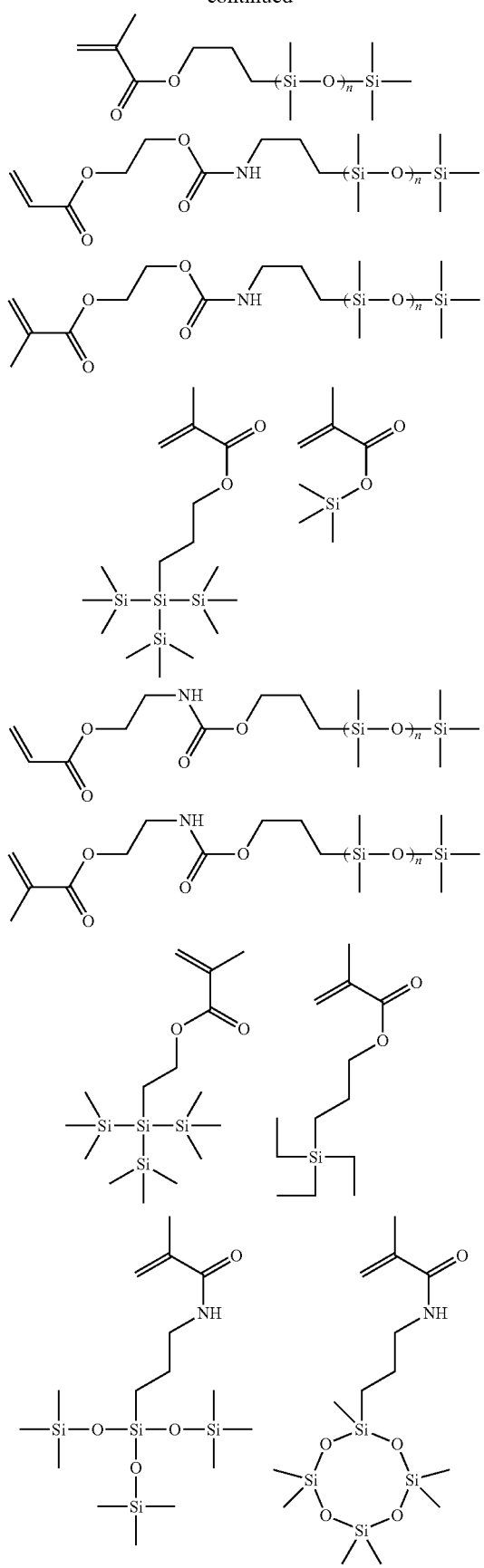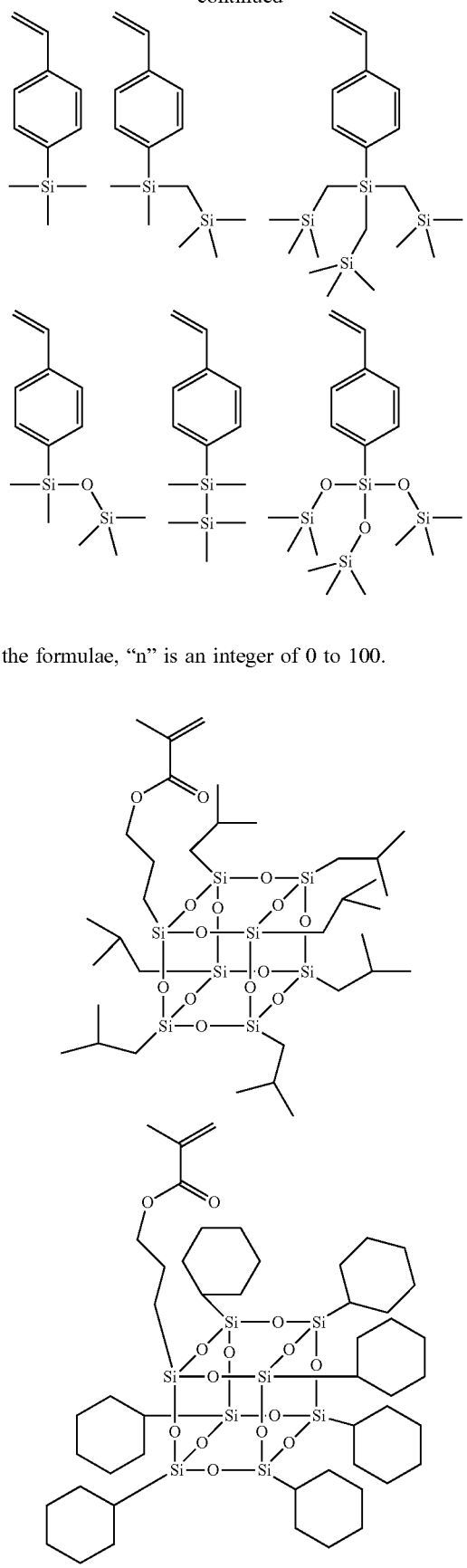
In the formulae, "n" is an integer of 0 to 100.

-continued

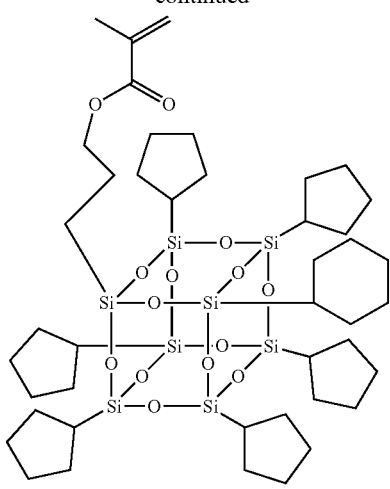

(Repeating Unit-c)

In the component (A) of the inventive bio-electrode composition, it is possible to copolymerize a repeating unit-c shown by the following general formula (4), optionally having an alkyl group, in addition to the repeating units-a and b,

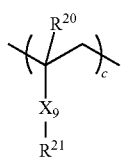

(4)

wherein $R^{20}$ represents a hydrogen atom or a methyl group; $X_9$ represents any of a single bond, a phenylene group, a naphthylene group, an ether group, an ester group, a phenylene group having an ester group, and an amide group; $R^{21}$ represents a linear, branched, or cyclic alkyl group having 1 to 40 carbon atoms, a linear, branched, or cyclic alkenyl group having 2 to 40 carbon atoms, a linear, branched, or cyclic alkynyl group having 2 to 40 carbon atoms, or an aryl group having 6 to 20 carbon atoms, optionally having an ether group, an ester group, or a hydroxy group; and "c" is a number satisfying $0<c<1.0$.

Illustrative examples of a monomer to give the repeating unit-c include the following.

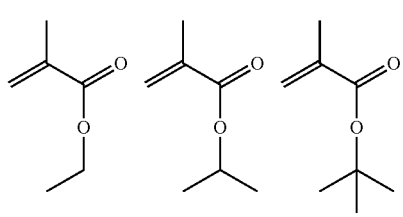

-continued

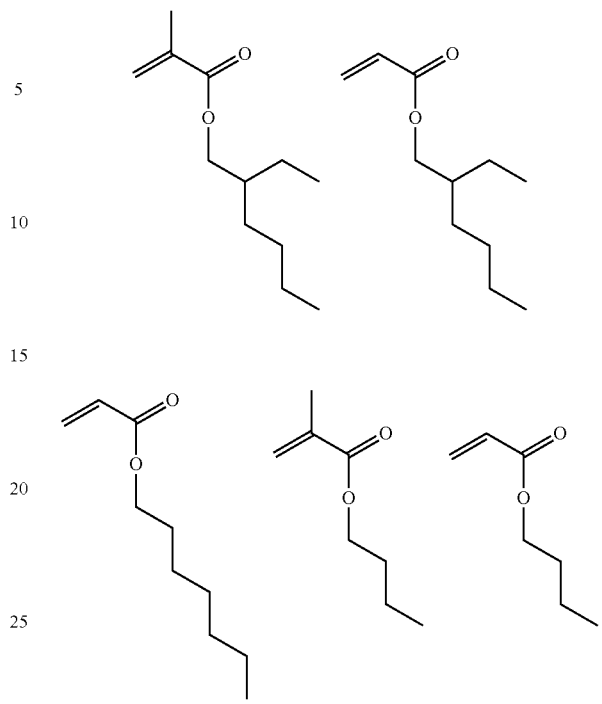

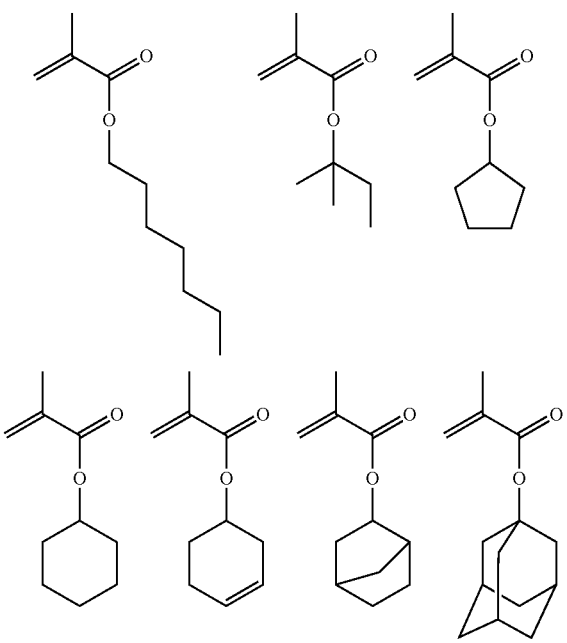

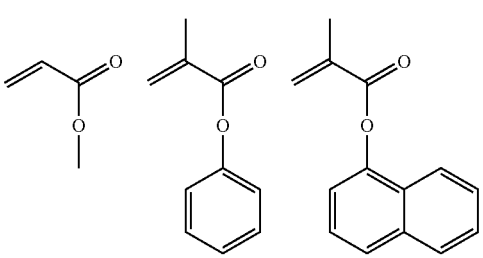

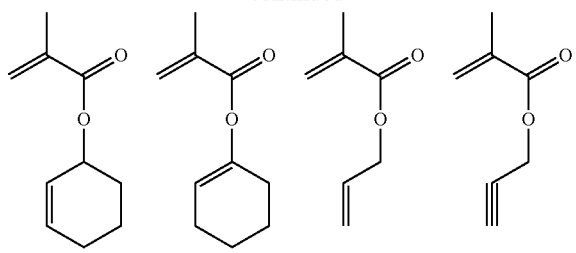
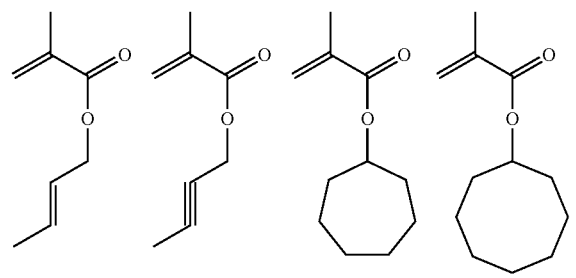
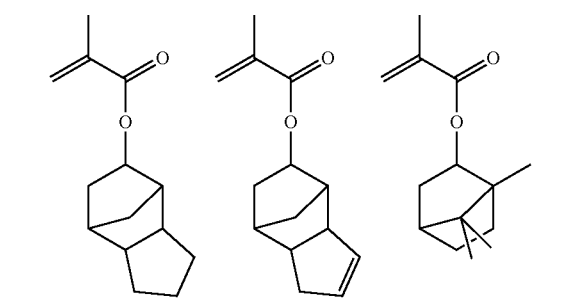
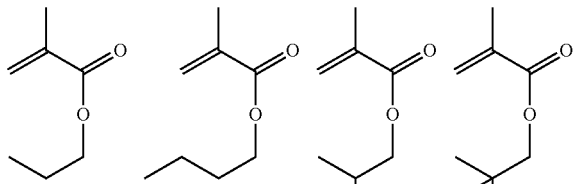
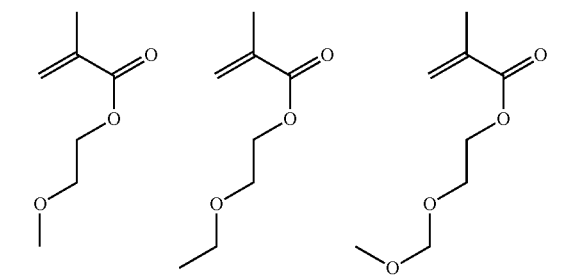
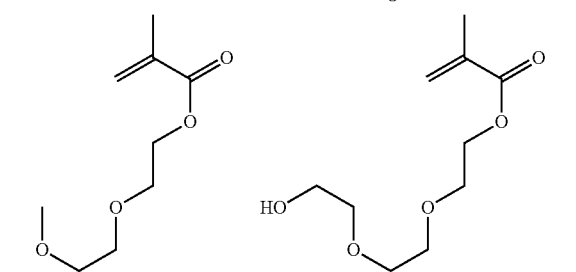
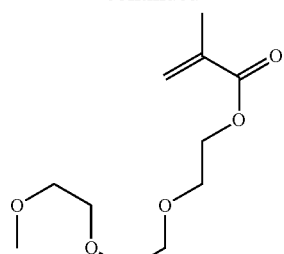
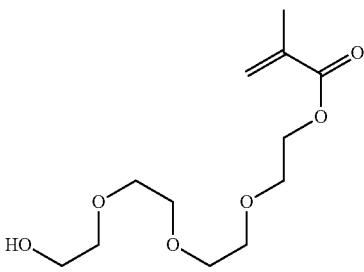
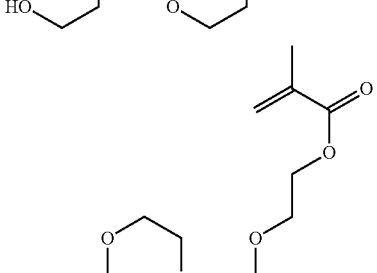
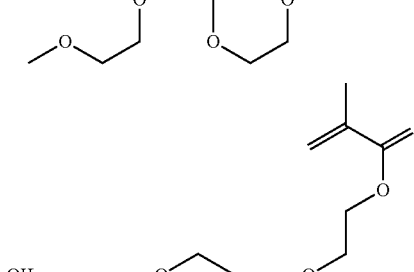
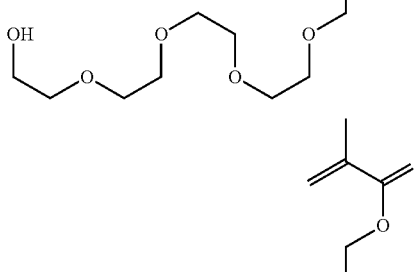
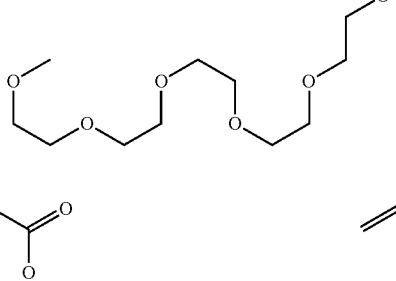
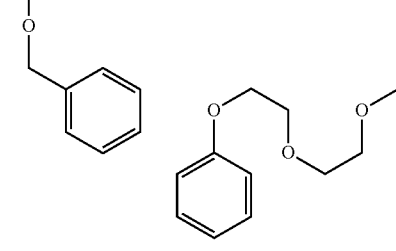

89
-continued
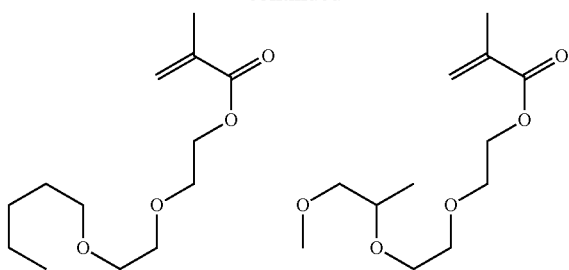
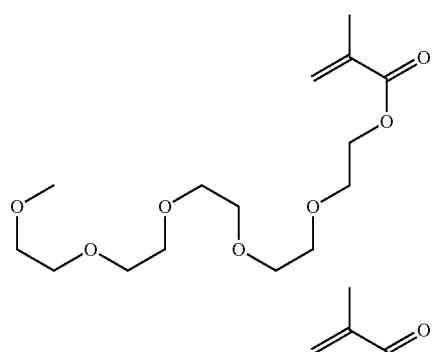
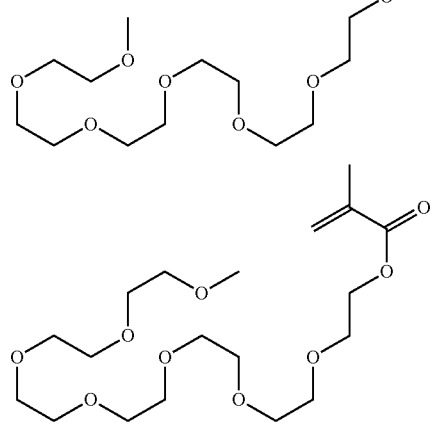
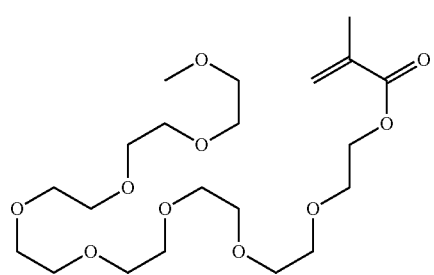
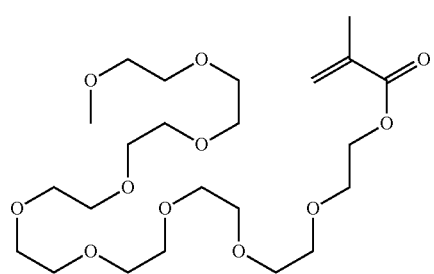
90
-continued
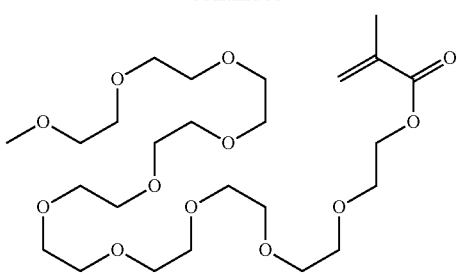

91
-continued
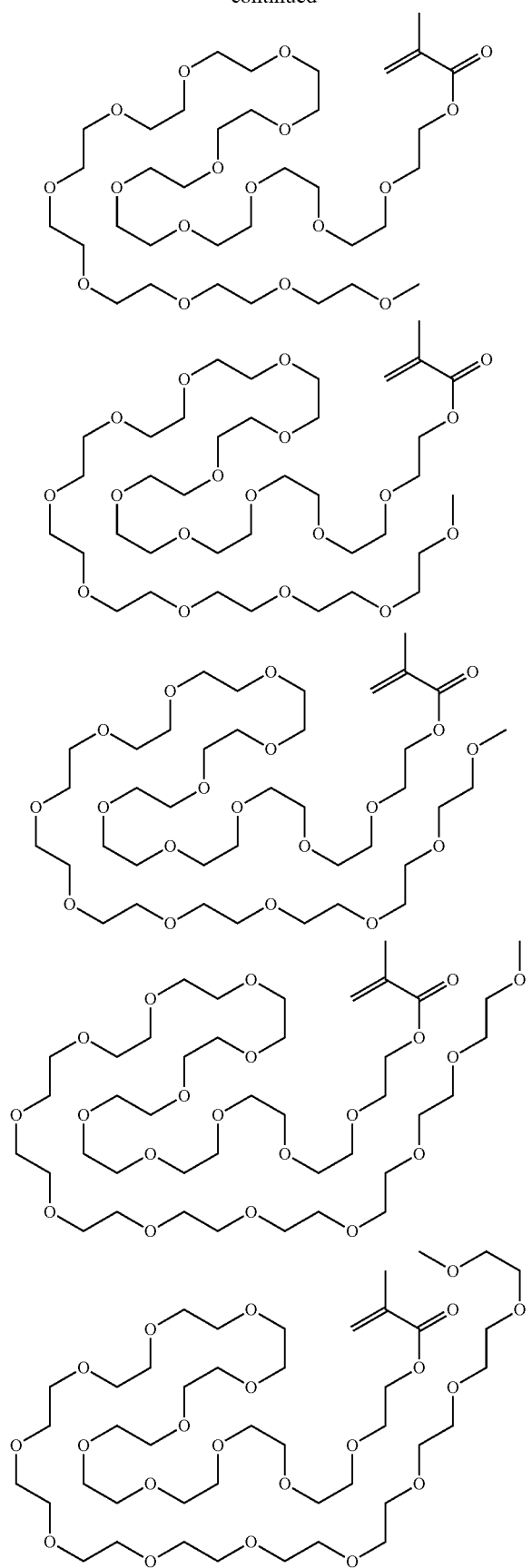
92
-continued
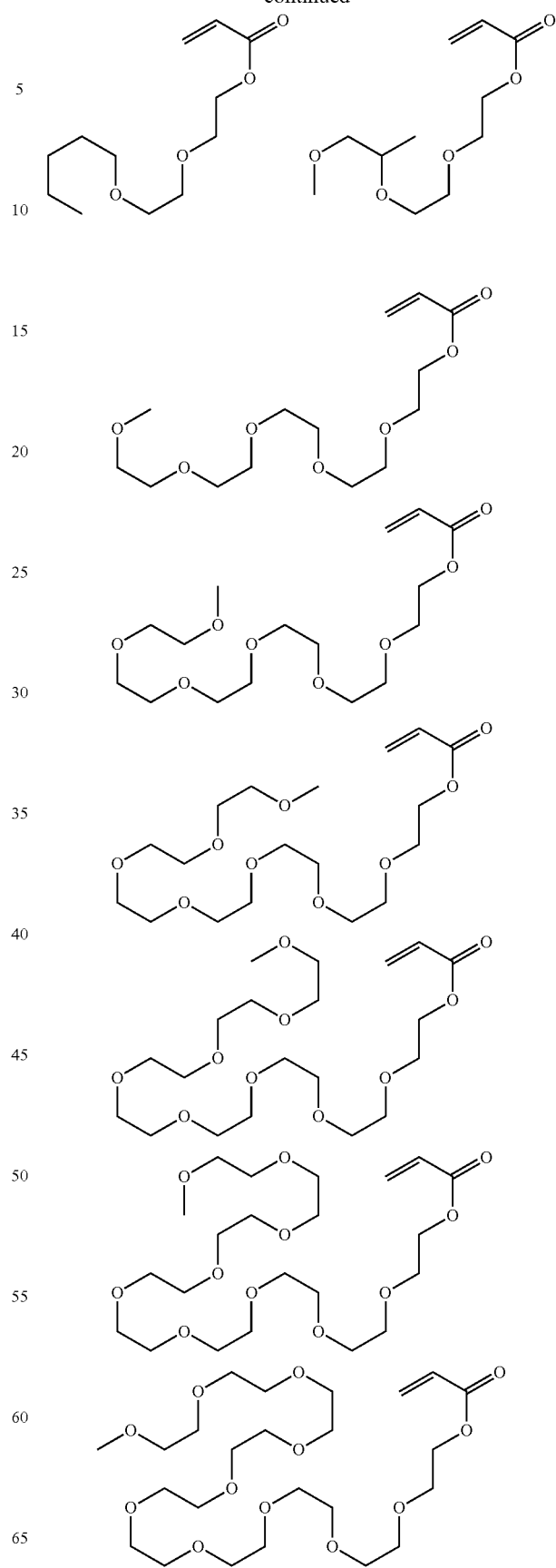

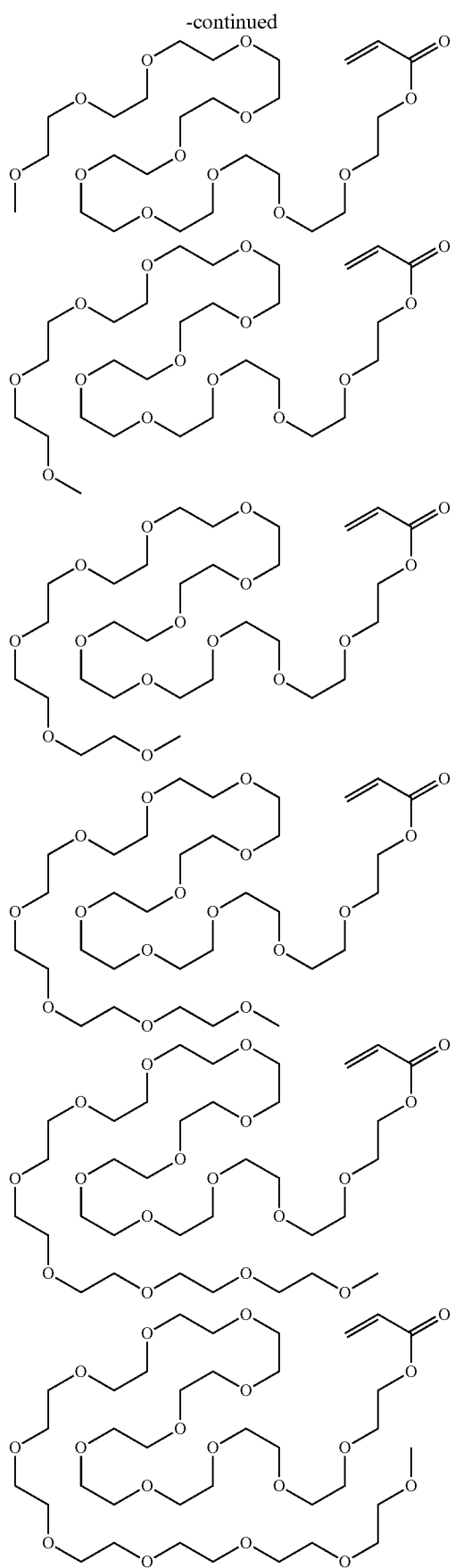
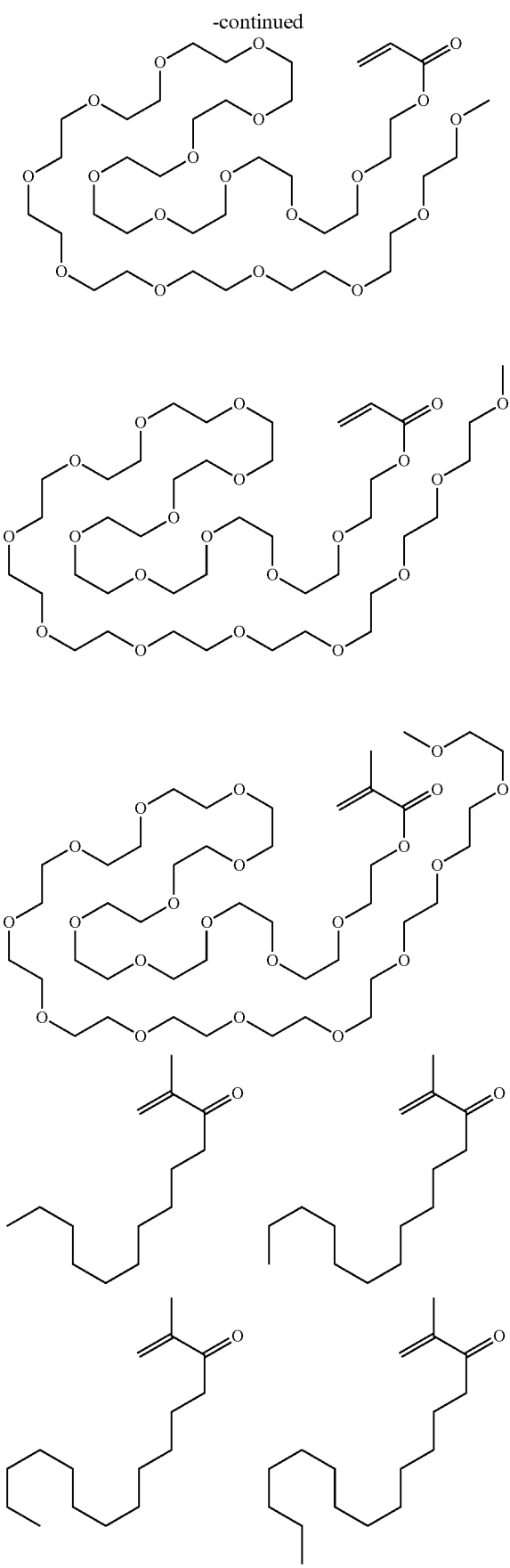

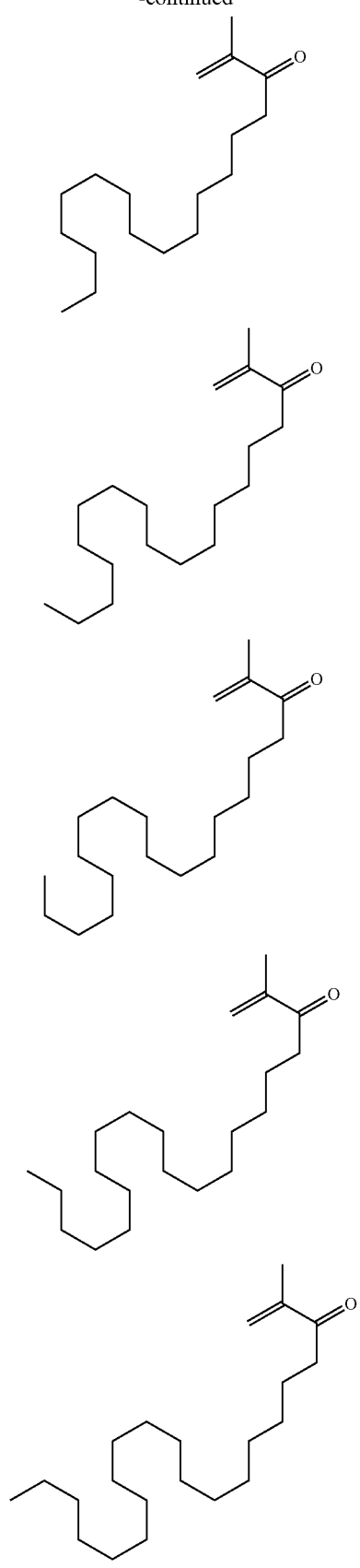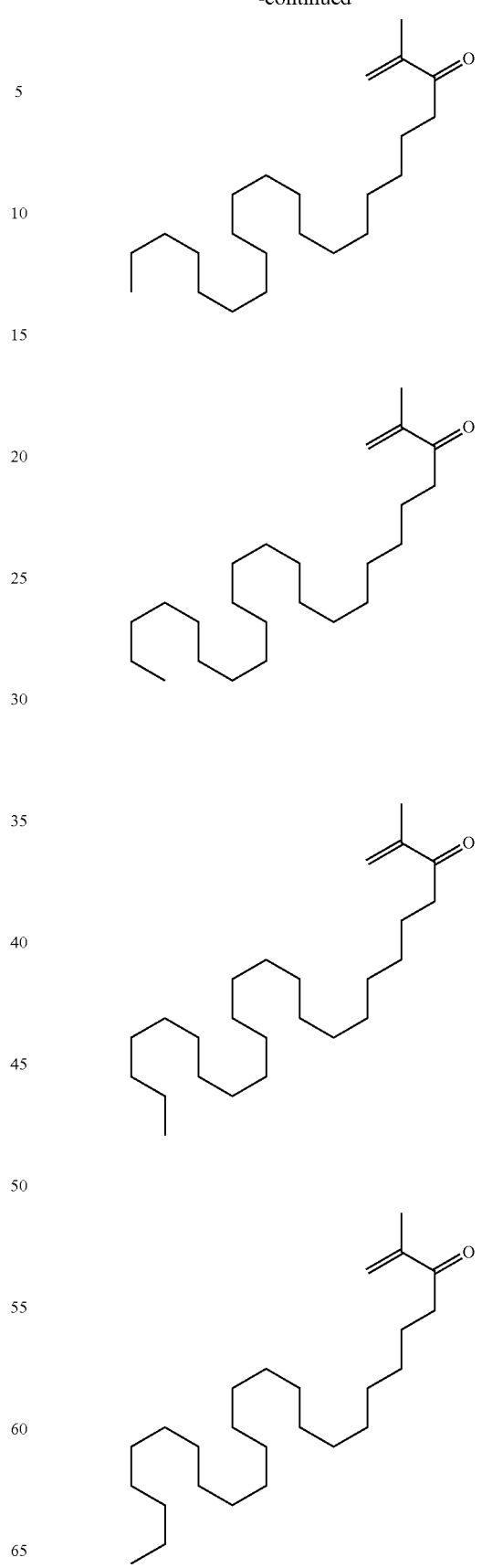

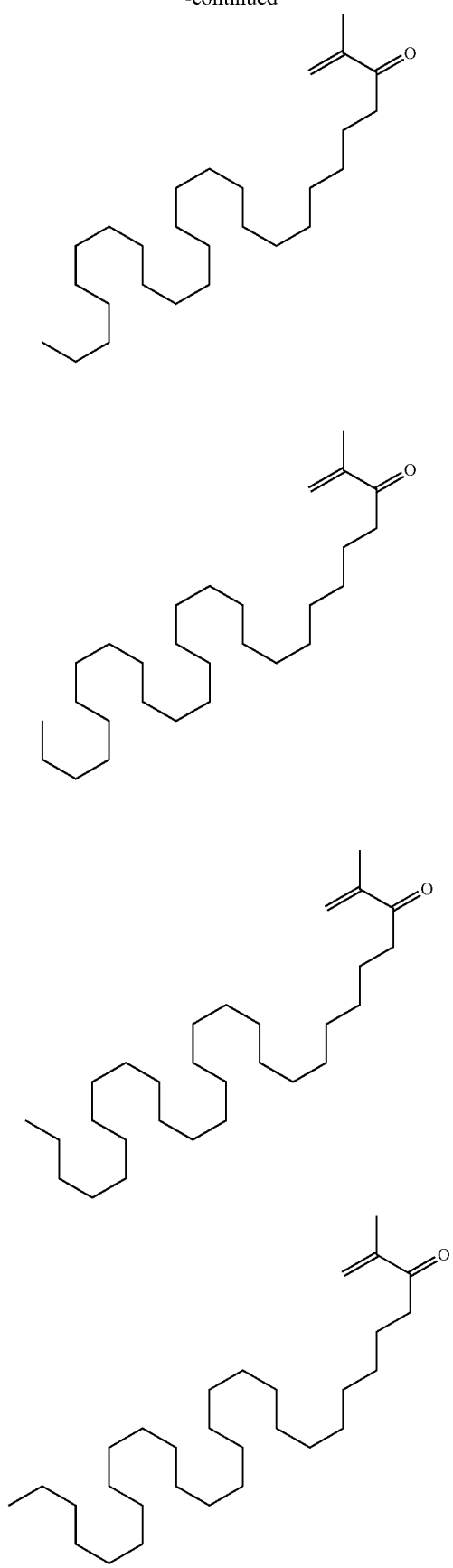
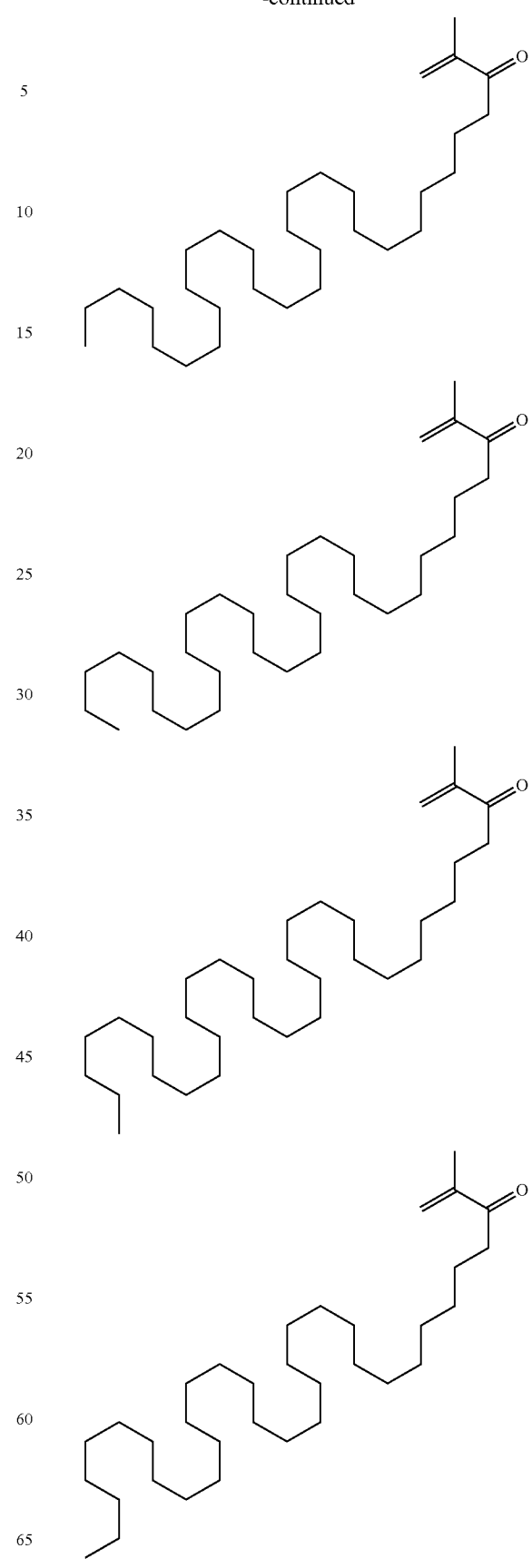

99
-continued
100
-continued
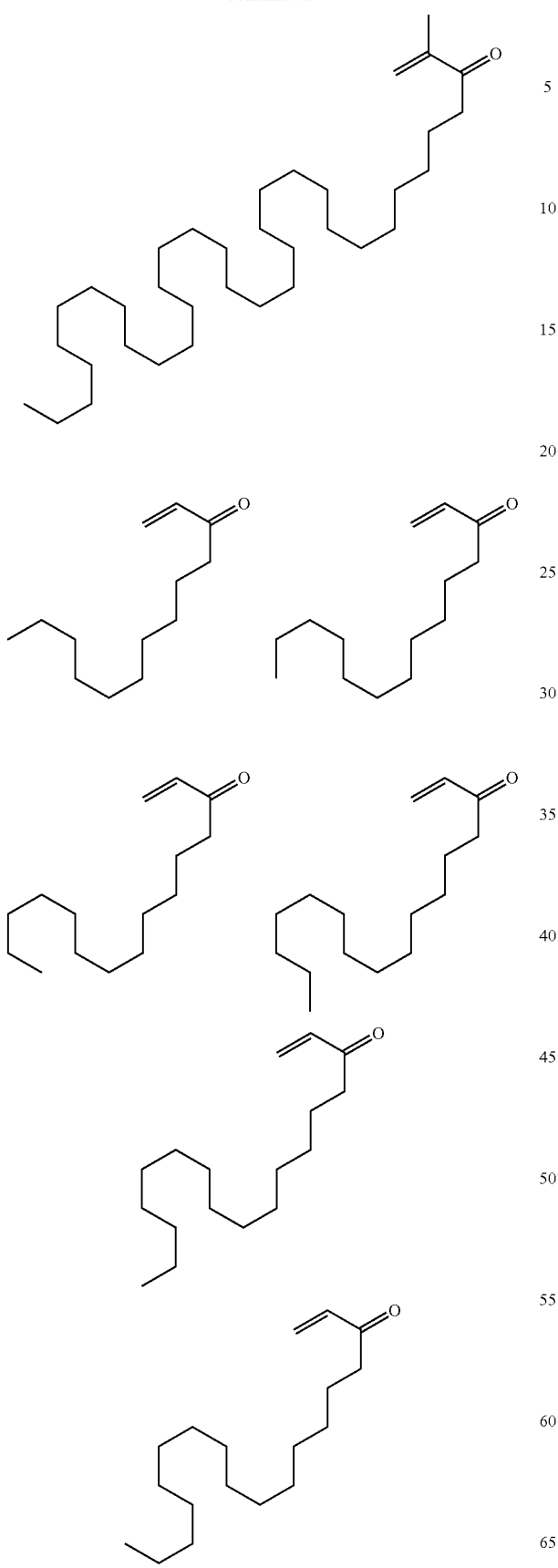
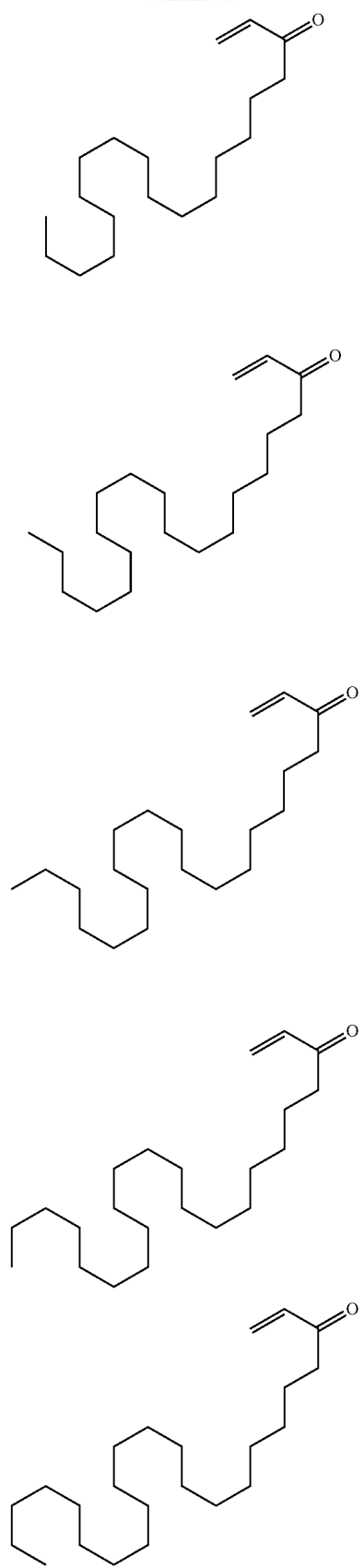

101
-continued
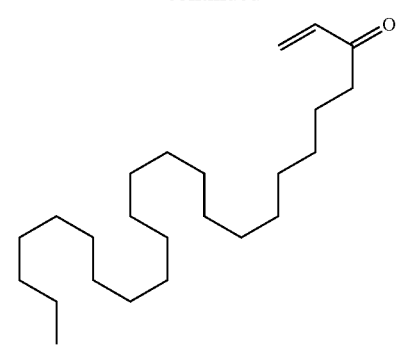
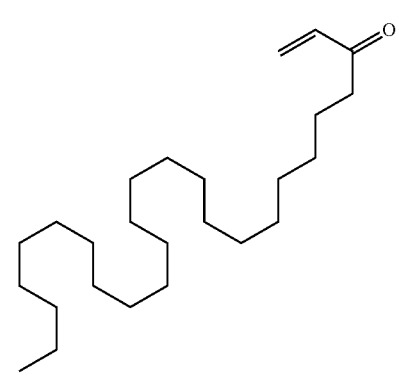
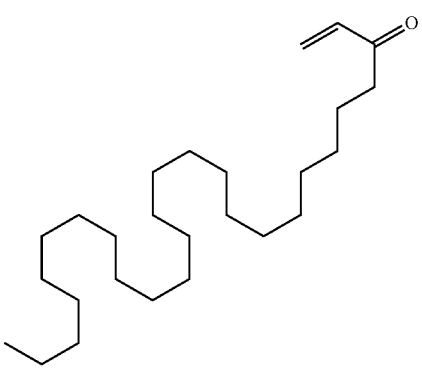
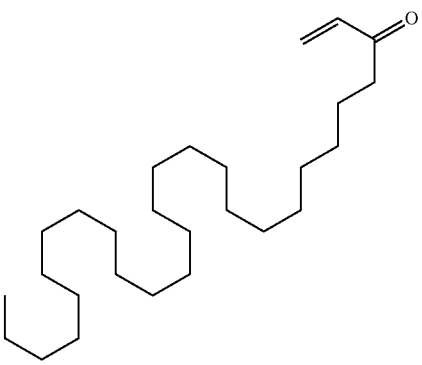
102
-continued
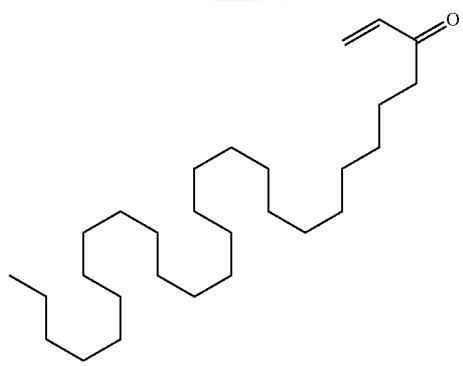
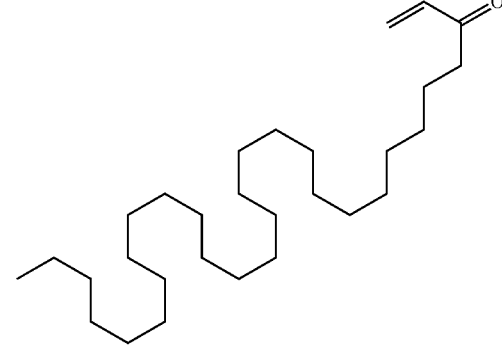
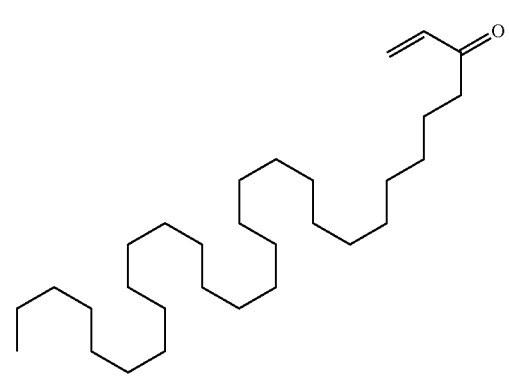
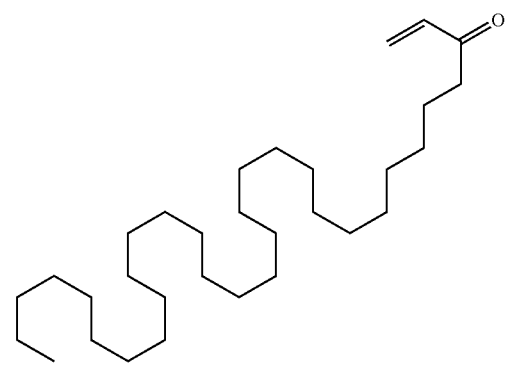

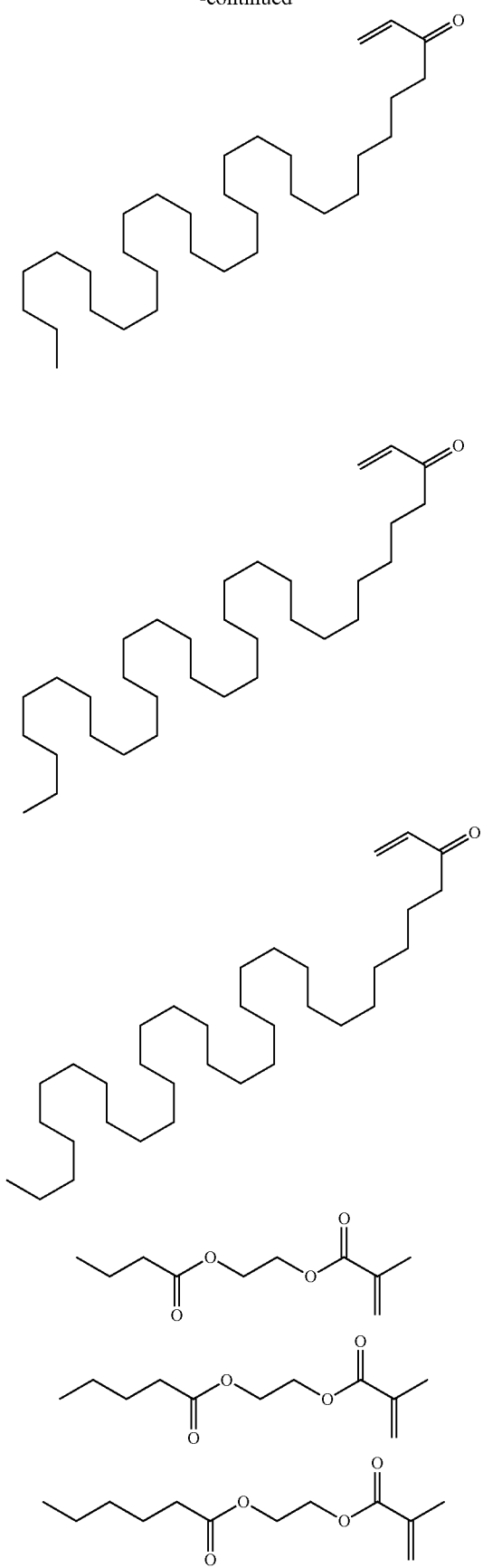
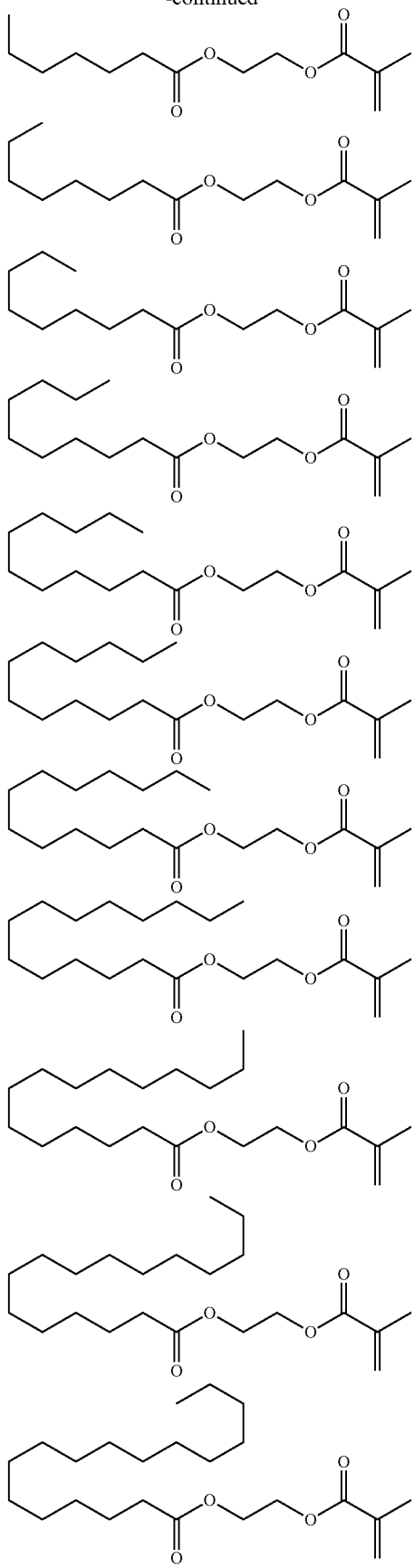

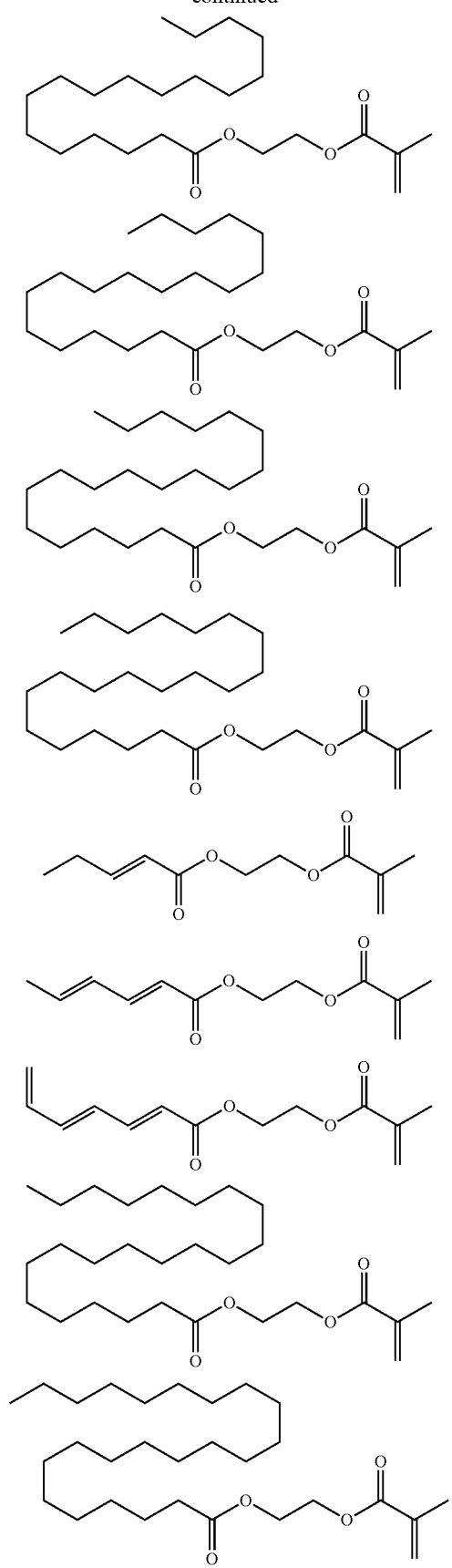
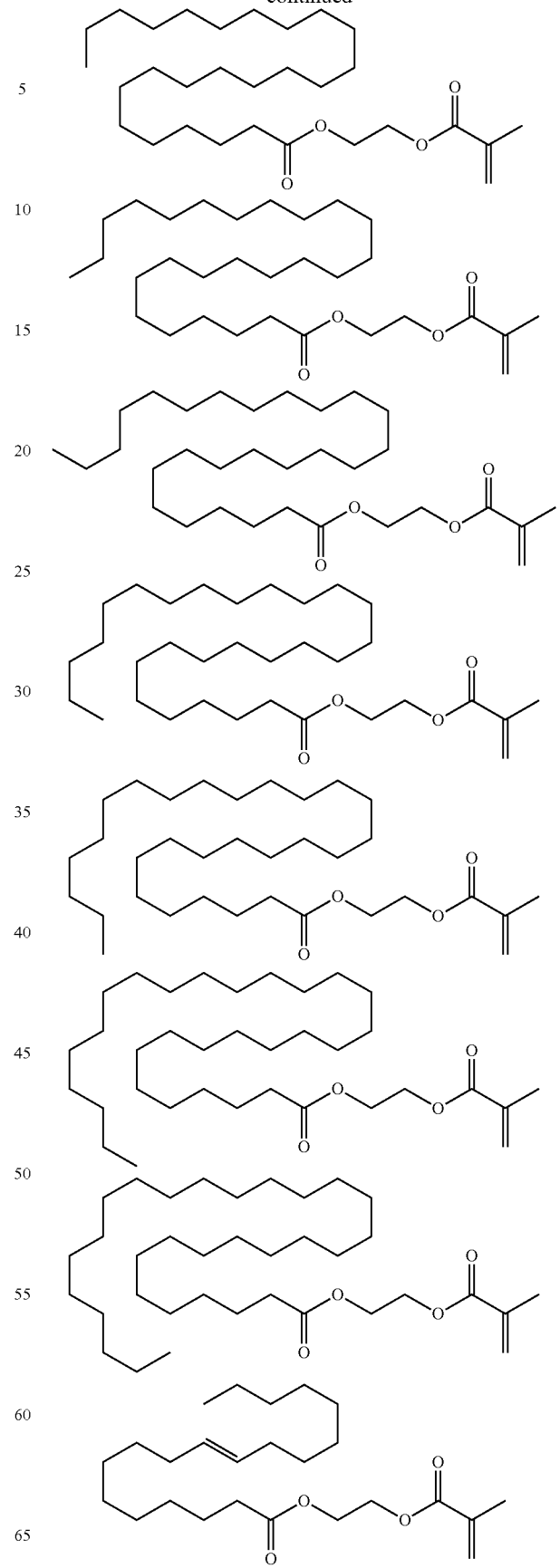

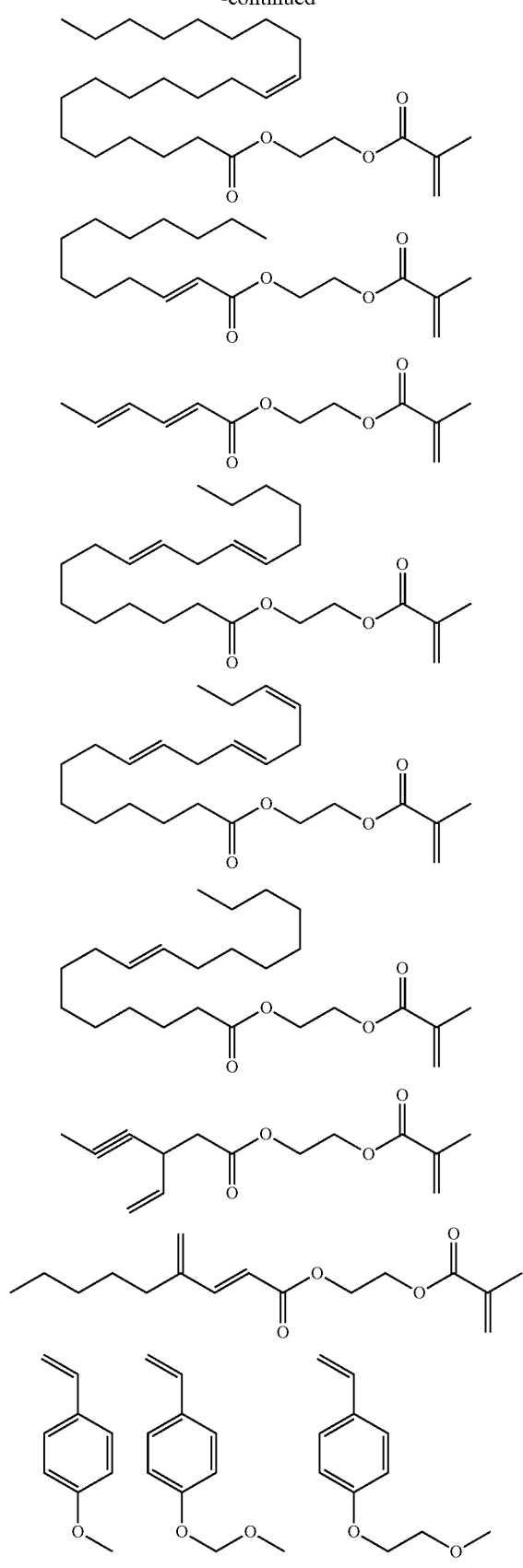
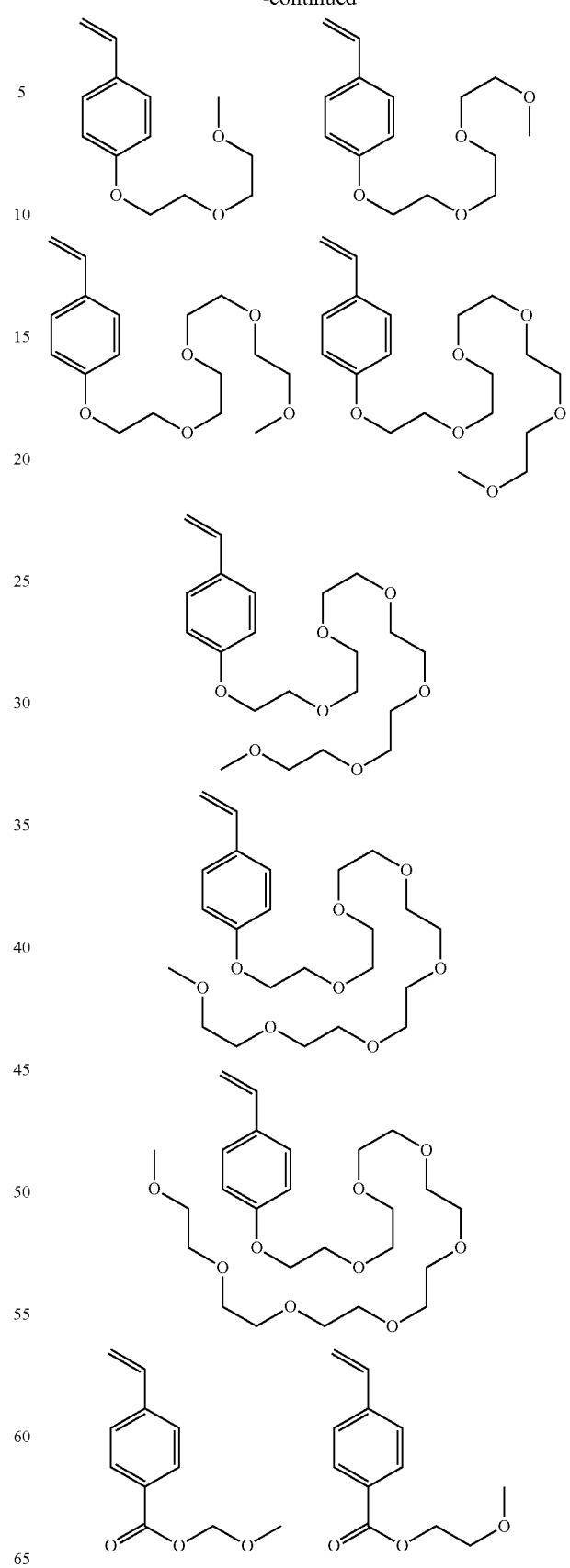

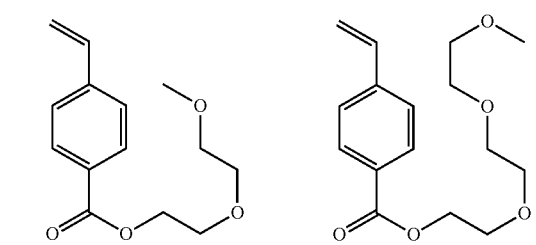
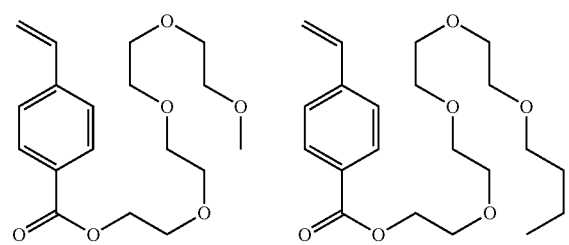
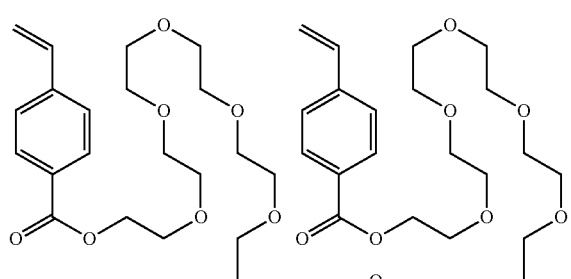
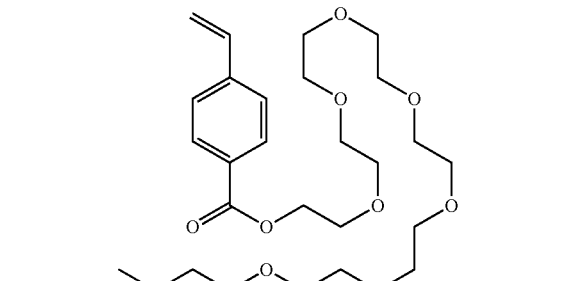
In the component (A) of the inventive bio-electrode composition, a crosslinkable monomer can also be copolymerized. The monomer for obtaining a crosslinkable repeating unit-d is characterized by having any of a hydroxy group, a carboxy group, an oxiran group, or an oxetan group, and illustrative examples thereof include the following.
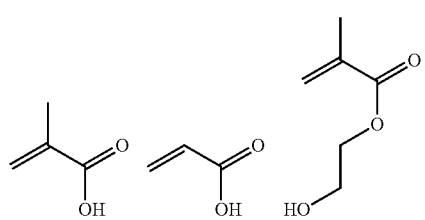
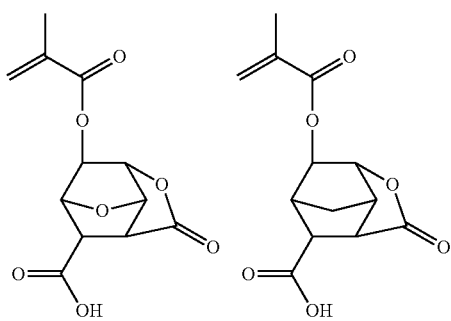
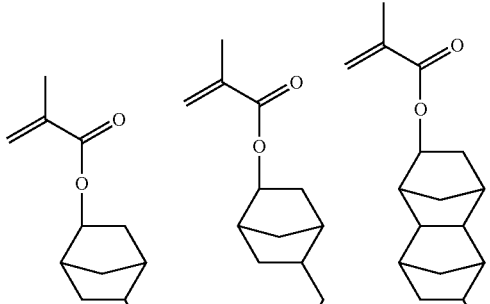
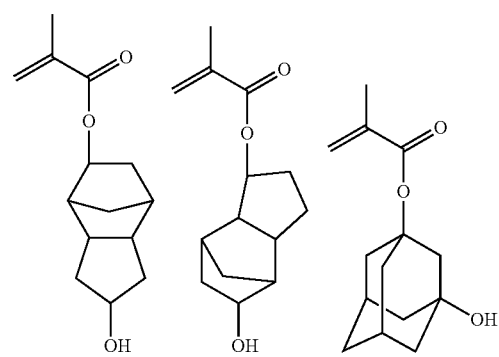
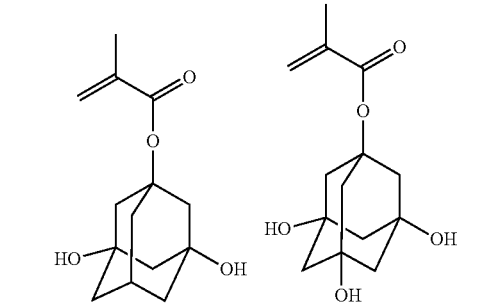
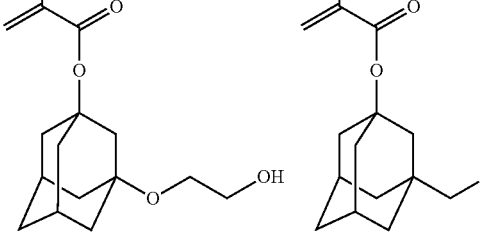

111
-continued
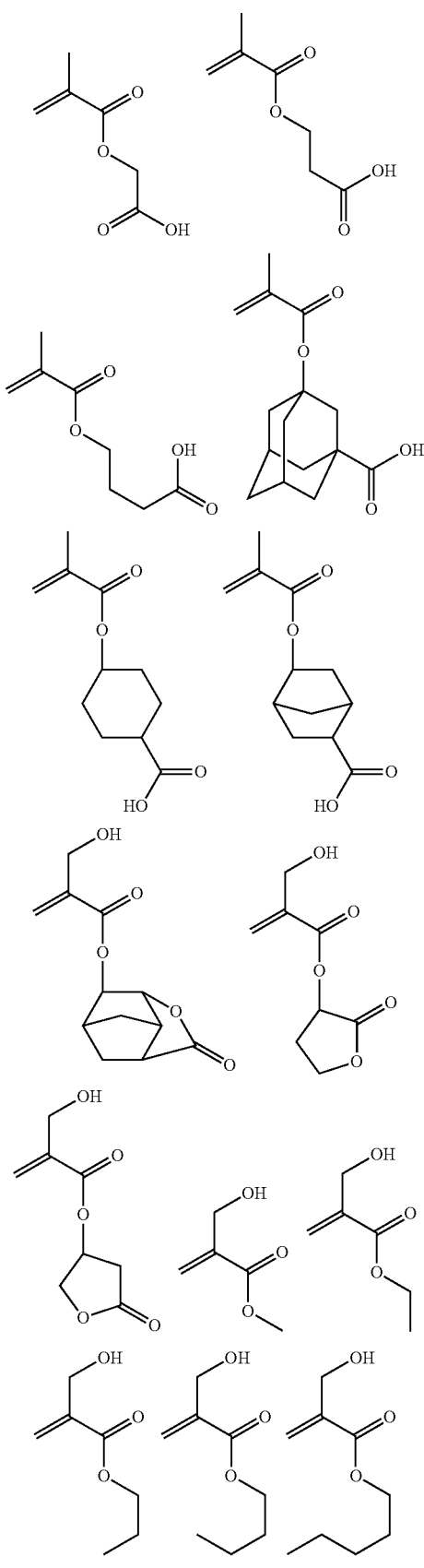
112
-continued
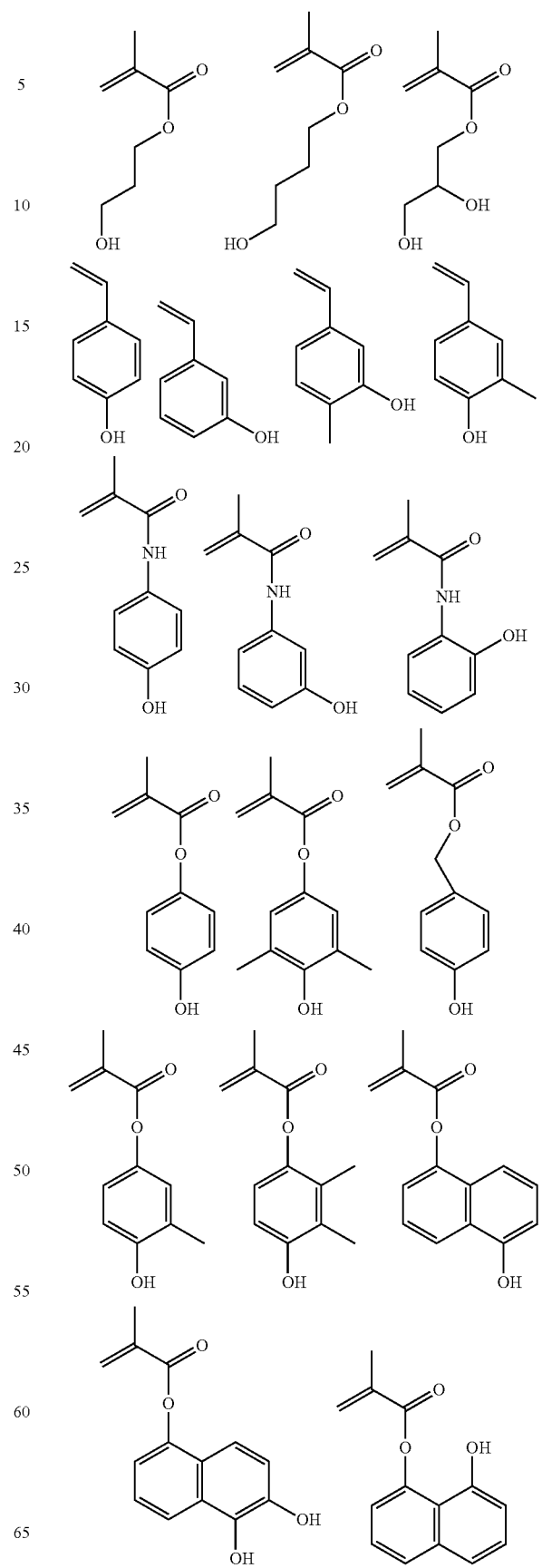

113
-continued
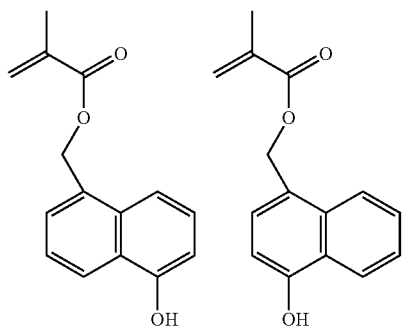
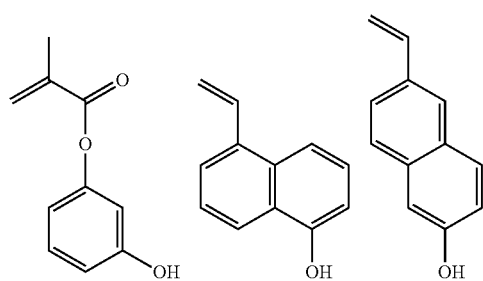
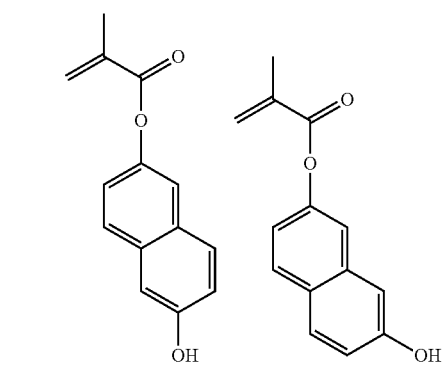
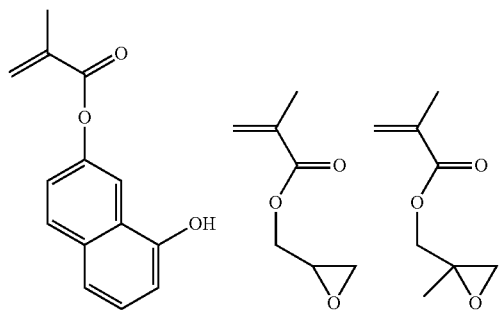
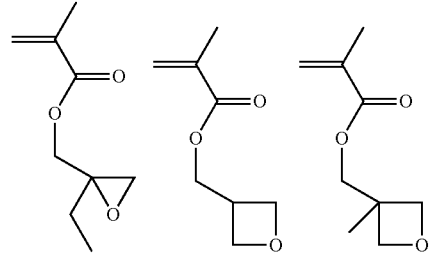
114
-continued
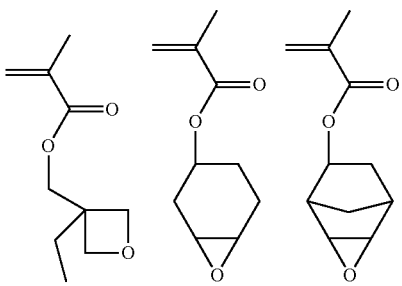
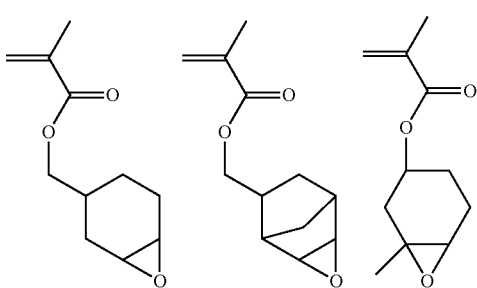
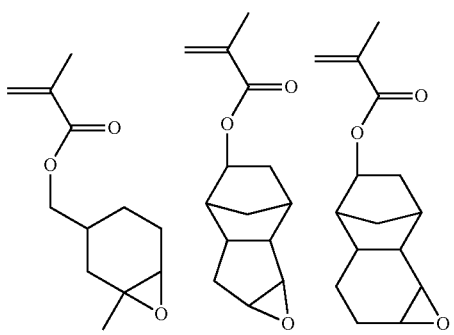
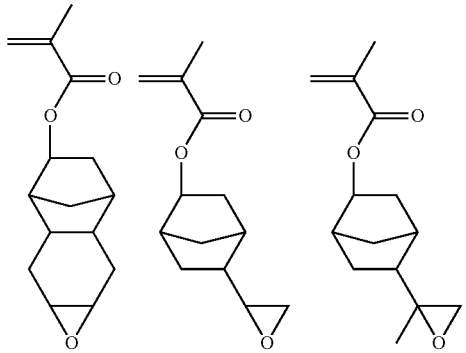
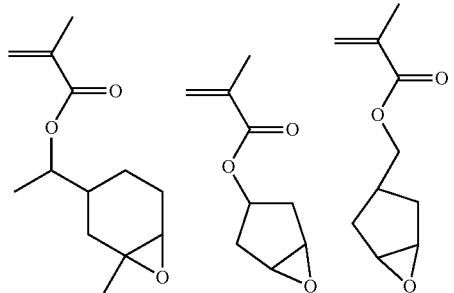

115
-continued
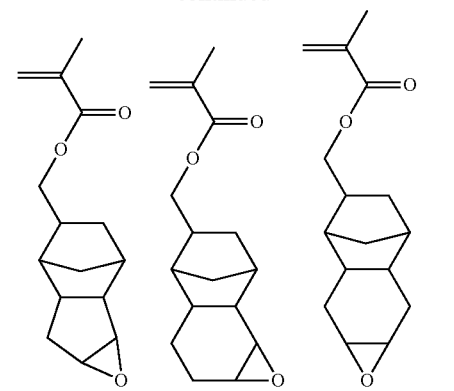
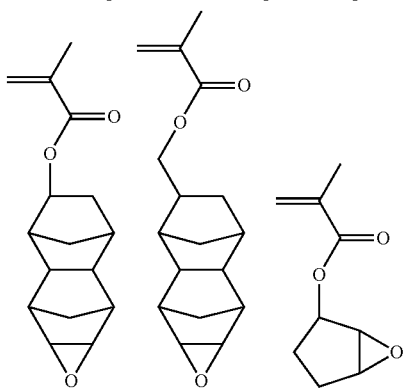
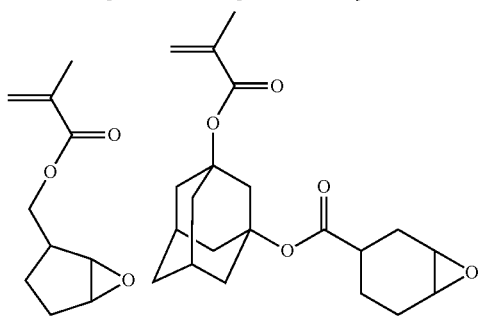
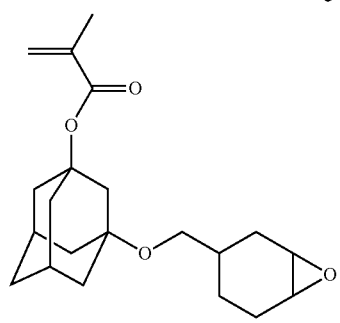
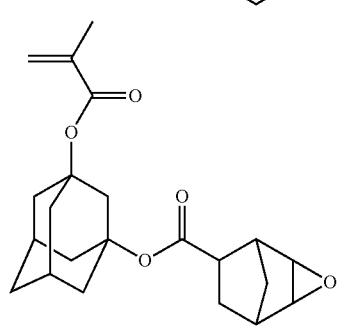
116
-continued
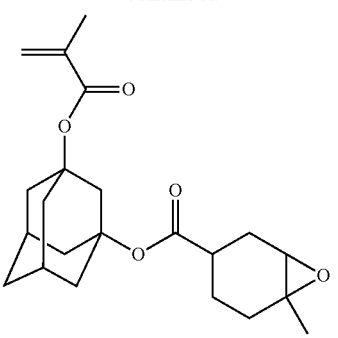
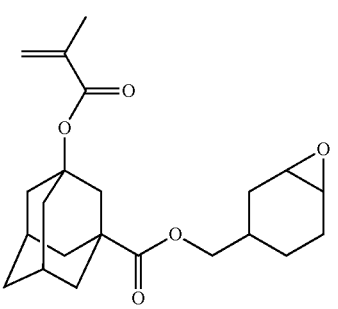
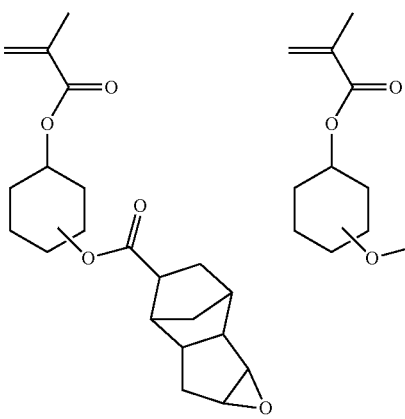
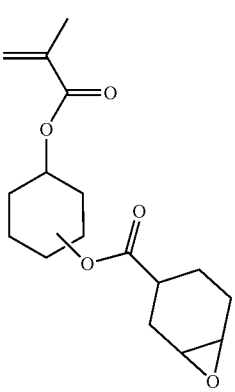

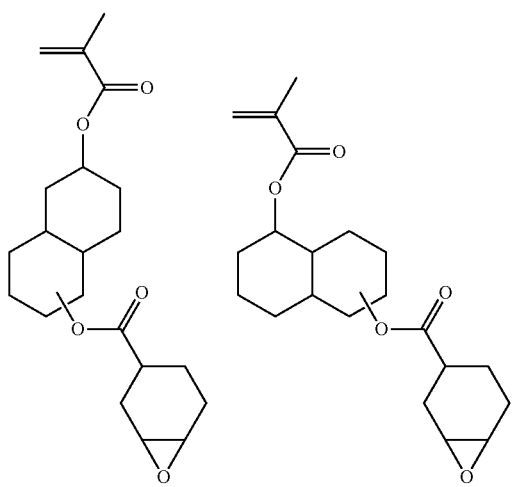
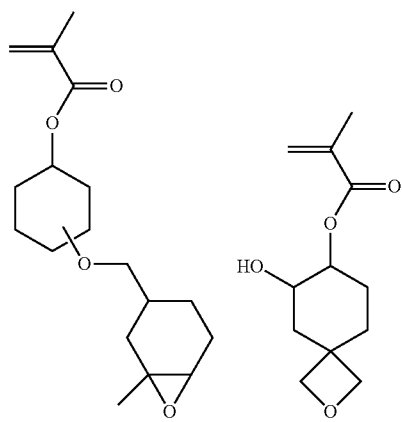
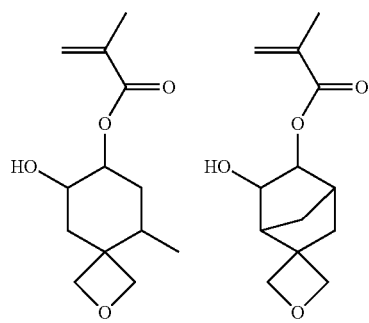
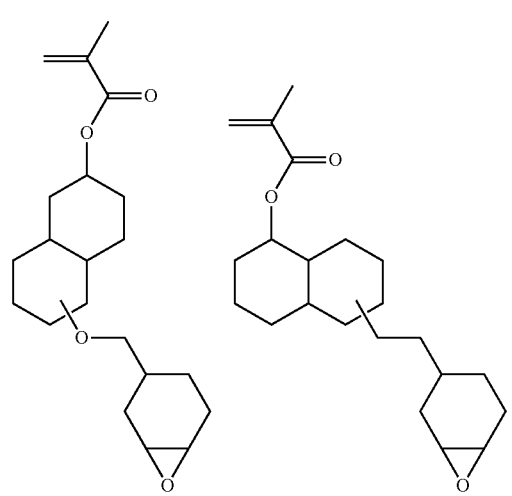
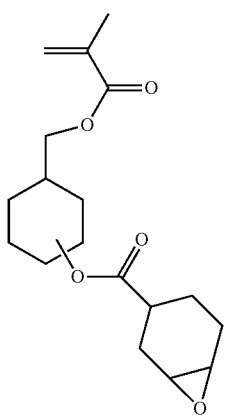
It is also possible to copolymerize a monomer-e having a plurality of polymerizable double bonds. This allows the polymers to be crosslinked after the polymerization. Illustrative examples of the monomer-e having a plurality of double bonds include the following.

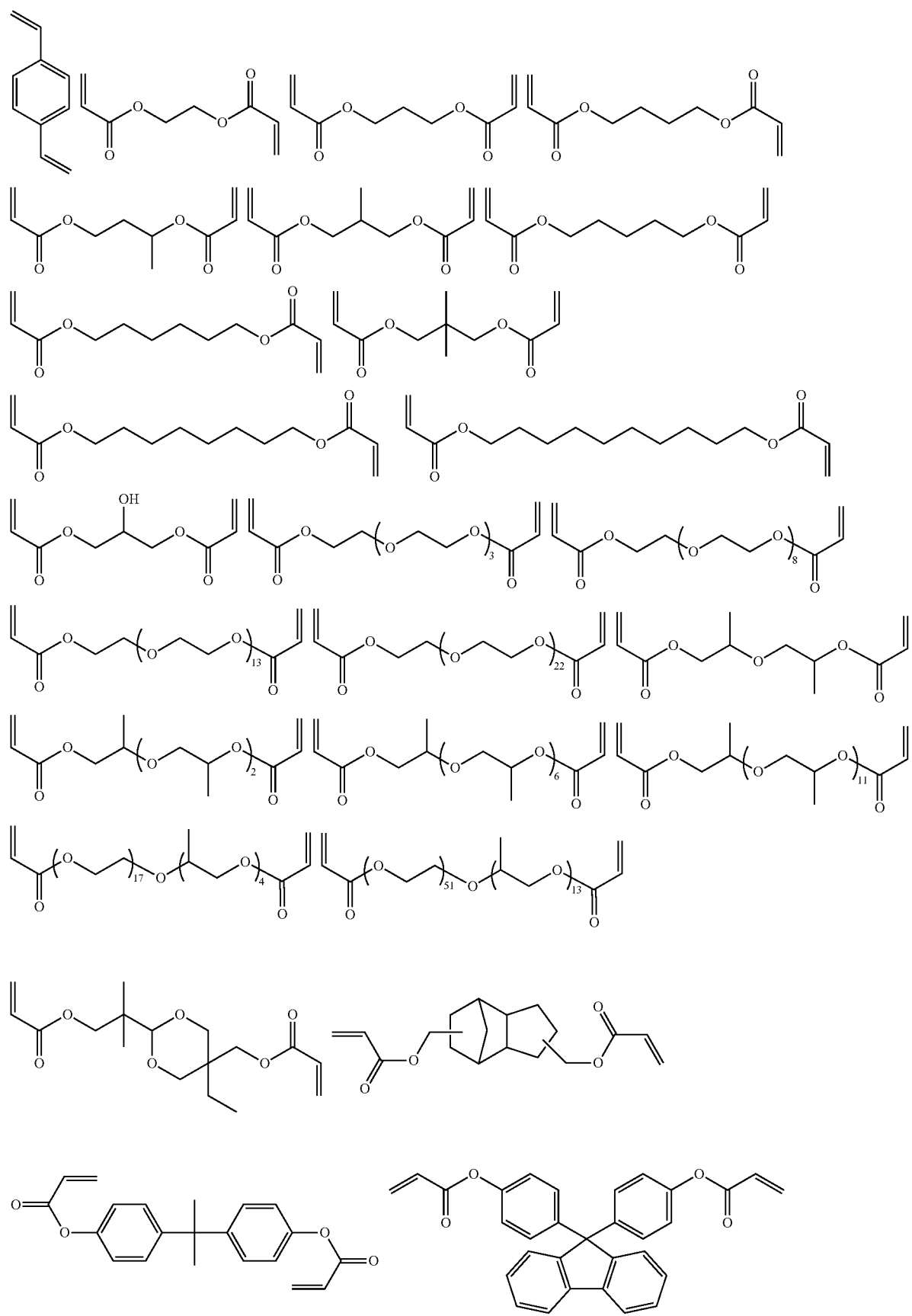

-continued
121
122
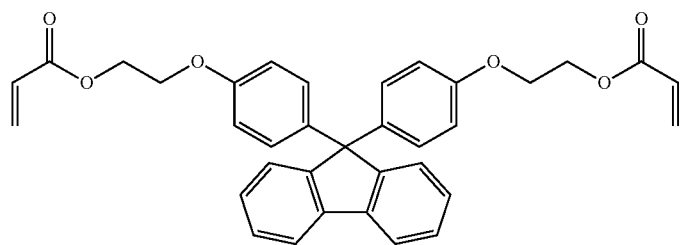
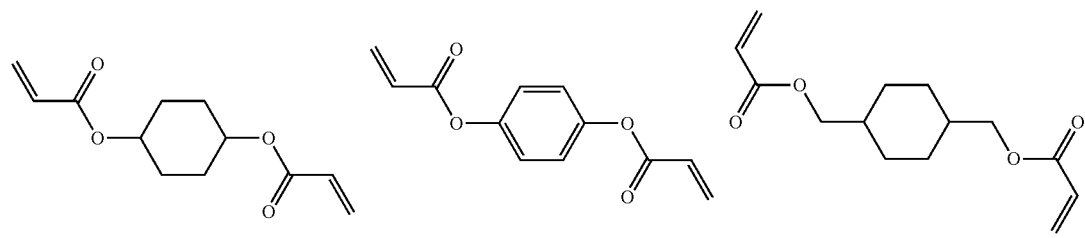
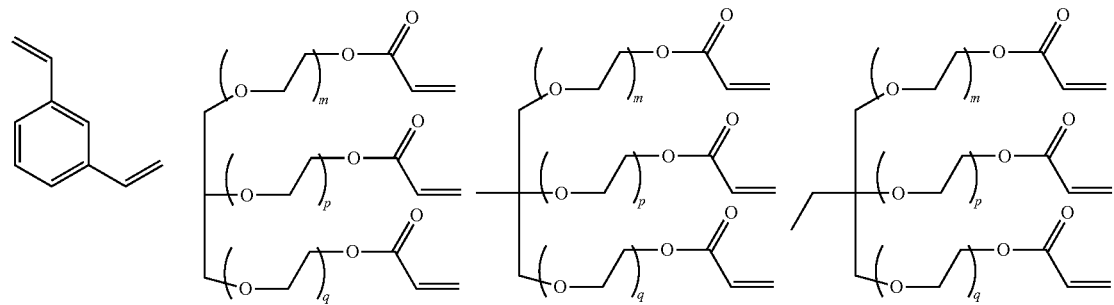
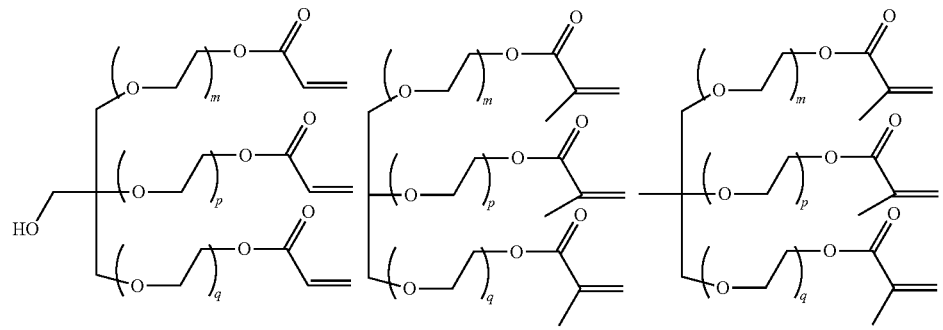
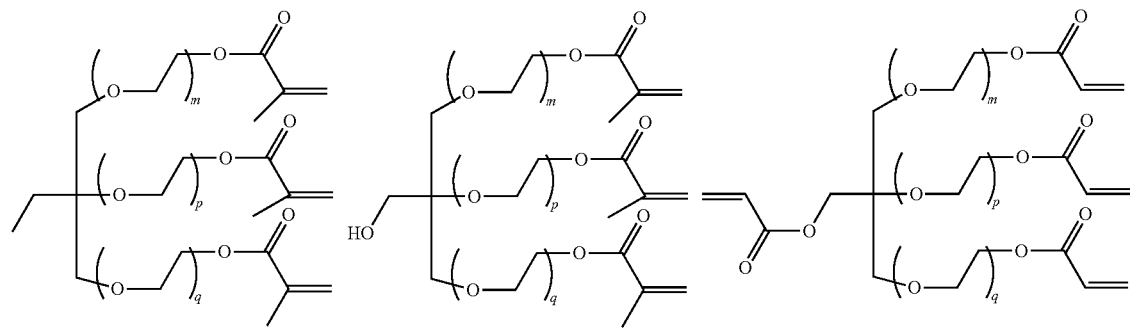

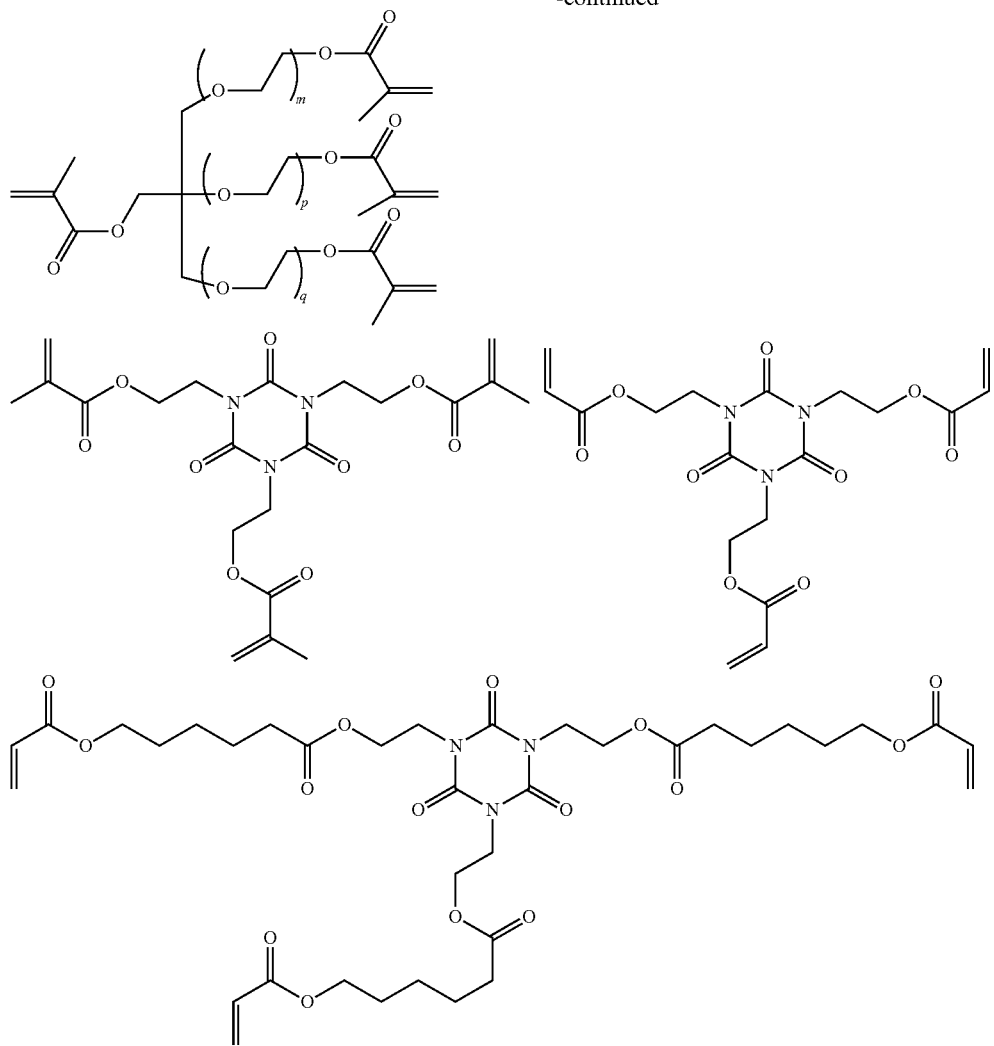
In the formulae, 3 m+p+q<30.
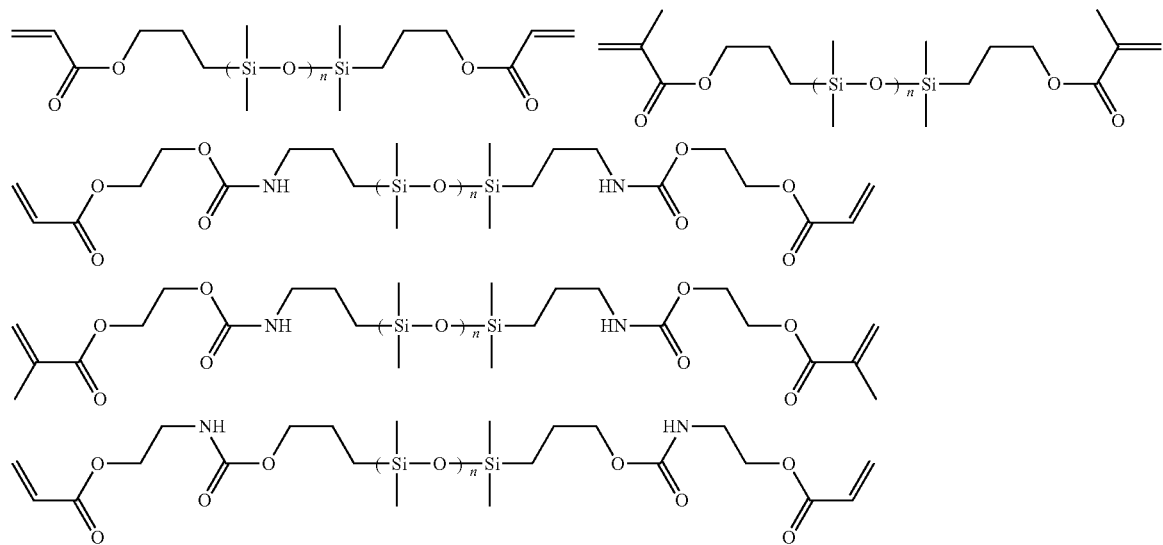

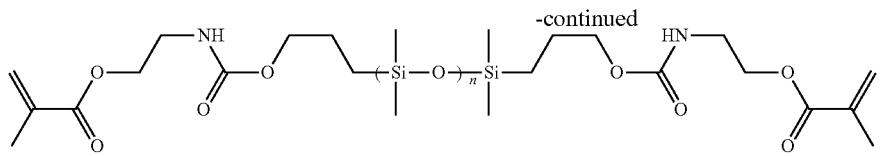

As one of the method for synthesizing the polymer compound of the component (A) (ionic material), the copolymer compound can be obtained by a method of heat polymerization of desired monomers among the monomers to give the repeating units a1 to a7, "b", "c", "d", and "e" through addition of a radical polymerization initiator in an organic solvent.

As the organic solvent used in the polymerization, toluene, benzene, tetrahydrofuran, diethyl ether, dioxane and so on can be exemplified. Illustrative examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. The temperature in the heat polymerization is preferably 50 to 80° C., and the reaction time is preferably 2 to 100 hours, more preferably 5 to 20 hours.

The ratios of the repeating units a1 to a7, "b", "c", "d", and "e" are $0 \leq a1 < 1.0$, $0 \leq a2 < 1.0$, $0 \leq a3 < 1.0$, $0 \leq a4 < 1.0$, $0 \leq a5 < 1.0$, $0 \leq a6 < 1.0$, $0 \leq a7 < 1.0$, $0 \leq a1+a2+a3+a4+a5+a6+a7 < 1.0$, $0 < b < 1.0$, $0 \leq c < 1.0$, $0 \leq d < 1.0$, and $0 \leq e < 1.0$; preferably $0 \leq a1 < 0.9$, $0 \leq a2 < 0.9$, $0 \leq a3 < 0.9$, $0 \leq a4 < 0.9$, $0 \leq a5 < 0.9$, $0 \leq a6 < 0.9$, $0 \leq a7 < 0.9$, $0.1 \leq a1+a2+a3+a4+a5+a6+a7 \leq 0.9$, $0.1 < b < 0.9$, $0 < c < 0.6$, d 0.6, and $0 \leq e \leq 0.6$; and more preferably $0 \leq a1 \leq 0.8$, $0 \leq a2 < 0.8$, $0 \leq a3 < 0.8$, $0 \leq a4 < 0.8$, $0 \leq a5 < 0.8$, $0 \leq a6 < 0.8$, $0 \leq a7 < 0.8$, $0.2 < a1+a2+a3+a4+a5+a6+a7 \leq 0.8$, $0.1 \leq b \leq 0.8$, $0 \leq c \leq 0.5$, $0 < d < 0.5$, and $0 \leq e \leq 0.5$.

Incidentally, $a1+a2+a3+a4+a5+a6+a7+b+c+d+e=1$, for example, means that the total amount of repeating units a1, a2, a3, a4, a5, a6, a7, "b", "c", "d", and "e"' is 100 mol % on the basis of the total amount of the whole repeating units in a polymer compound that contains repeating units a1, a2, a3, a4, a5, a6, a7, "b", "c", "d", and "e"; and $a1+a2+a3+a4+a5+a6+a7+b+c+d+e<1$ means that the total amount of repeating units a1, a2, a3, a4, a5, a6, a7, "b", "c", "d", and "e" is less than 100 mol % on the basis of the total amount of the whole repeating units, and another repeating unit(s) is contained other than the repeating units a1, a2, a3, a4, a5, a6, a7, "b", "c", "d", and "e".

The molecular weight of the component (A), as a weight average molecular weight, is preferably 500 or more, more preferably 1,000 or more and 1,000,000 or less, further preferably 2,000 or more and 500,000 or less. With few amount of the ionic monomer that is not incorporated into the component (A) after polymerization (residual monomer), they are prevented from the risk of permeating to skin in a biocompatibility test to cause allergy. Accordingly, it is preferable to reduce the amount of residual monomer(s). The amount of residual monomer(s) is preferably 10 parts by mass or less on the basis of 100 parts by mass of the whole component (A).

In the inventive bio-electrode composition, the amount of the component (A) is preferably 0.1 to 300 parts by mass, more preferably 1 to 200 parts by mass on the basis of 100 parts by mass of the component (B). The component (A) may be used singly or in admixture of two or more kinds.

[(B) Resin Other than Component (A)]

The component (B) contained in the inventive bio-electrode composition is a component for preventing elution of the salt through mutual dissolution thereof with (A) the ionic material (salt), for holding an electric conductivity improver such as carbon, and for achieving adhesion. It is to be noted that the component (B) may be any of a resin other than the component (A) and is preferably either or both of a thermosetting resin and a photo-curable resin, particularly one or more resins selected from silicone base, acrylic base, and urethane base resins.

The adherent silicone base resin include an addition-curable (addition reaction-curable) type and a radical curable (radical crosslinking reaction-curable) type. As the addition-curable type, it is possible to use one that contains diorganosiloxane having an alkenyl group(s), an MQ resin having an $R_3SiO_{0.5}$ unit and an $SiO_2$ unit, organohydrogenpolysiloxane having a plurality of SiH groups, a platinum catalyst, an addition reaction inhibitor, and organic solvent, for example, described in JP 2015-193803A. As the radical curable type, it is possible to use one that contains diorganopolysiloxane with or without an alkenyl group, an MQ resin having an $R_3SiO_{0.5}$ unit and an $SiO_2$ unit, organic peroxide, and organic solvent, for example, described in JP 2015-193803A. Herein, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanol and improves adhesion by addition of it, but does not bind to polysiloxane in molecular level because it is not crosslinkable. The adhesion can be increased by integrating the polysiloxane and the MQ resin as described above.

The silicone resin may contain modified siloxane that has a group selected from an amino group, an oxiran group, an oxetan group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring. The addition of modified siloxane improves dispersibility of the component (A) in the silicone resin. Any modified siloxane is usable irrespective of being modified at one terminal, the both terminals, or the side chain of the siloxane.

As the adherent acrylic base resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane base resin, it is possible to use one having a urethane bond with a polyether bond, a polyester bond, a polycarbonate bond, or a siloxane bond described in JP 2016-065238A, for example.

In the inventive bio-electrode composition, the component (B) preferably has high compatibility with the component (A) to prevent lowering of the electric conductivity due to elution of the component (A) from the living body contact layer. In the inventive bio-electrode composition, the component (B) preferably has high adhesion to the electro-conductive base material to prevent delamination of the living body contact layer from the electro-conductive base material. In order to increase the compatibility of the component (B) with the electro-conductive base material and the salt, the use of resin with high polarity is effective. Illustrative examples of such resin include resin having one or more moieties selected from an ether bond, an ester bond, an amide bond, an imide bond, an urethane bond, a thiourethane bond, and a thiol group; as well as polyacrylic resin, polyamide resin, polyimide resin, polyurethane resin, and polythiourethane resin. On the other hand, the living body contact layer is in contact with a living body, thereby being susceptible to perspiration. Accordingly, in the inventive bio-electrode composition, the component (B) preferably has high repellency, and is hardly hydrolyzed. To make the resin be highly repellent and hardly hydrolyzed, the use of silicon-containing resin is effective.

The silicon atom-containing polyacrylic resin includes a polymer that has a silicone main chain and a polymer that has a silicon atom(s) on the side chain, each of which can be suitably used. As the polymer that has a silicone main chain, silsesquioxane or siloxane having a (meth)acrylpropyl group and so on can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680, for example. Such a polyamide silicone resin can be synthesized by combining a silicone or non-silicone compound having amino groups at the both terminals and a non-silicone or silicone compound having carboxy groups at the both terminals.

It is also possible to use polyamic acid before cyclization thereof, which is obtained by reacting carboxylic anhydride and amine. The carboxy group of the polyamic acid may be crosslinked by using a crosslinking agent such as an epoxy type and an oxetan type. It is also possible to esterify the carboxy group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Illustrative examples of the silicon atom-containing polyurethane resin include polyurethane silicone resins. These polyurethane silicone resins can be crosslinked through urethane bond by blending a compound having isocyanate groups at the both terminals and a compound having a hydroxy group(s) at the terminal(s), followed by heating thereof. In this case, a silicon atom(s) (siloxane bond) have to be contained in either or both of the compound having isocyanate groups at the both terminals and the compound having a hydroxy group(s) at the terminal(s). Alternatively, an urethane (meth)acrylate monomer and polysiloxane can be blended and photo-crosslinked as described in JP 2005-320418A. It is also possible to photo-crosslink a polymer having both of a siloxane bond(s) and an urethane bond(s), with the terminal having a (meth)acrylate group(s).

The silicon atom-containing polythiourethane resin can be obtained by reaction of a compound having a thiol group(s) and a compound having an isocyanate group(s), provided that either of them have to contain a silicon atom(s). It can also be photo-cured if (meth)acrylate groups are contained at the terminals.

The silicone base resin is improved in compatibility with the foregoing salt by adding modified siloxane that has a group selected from an amino group, an oxiran group, an oxetan group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring in addition to the diorganosiloxane having an alkenyl group(s), the MQ resin having an $R_2SiO_{0.5}$ unit and an $SiO_2$ unit, and the organohydrogenpolysiloxane having a plurality of SiH groups.

As will be described later, the living body contact layer is a cured material of the bio-electrode composition. Curing the same improves the adhesion of the living body contact layer to both of skin and the electro-conductive base material. The curing means is not limited, and common means can be used, including crosslinking reaction by either or both of heat and light, an acid catalyst, or a base catalyst. The crosslinking reaction can be performed by appropriately selecting a crosslinking method described in "Kakyou hannou handbook (handbook of crosslinking reaction)", Chapter 2, pages 51-371, Yasuharu Nakamura, Maruzen shuppan (2013).

The diorganosiloxane having an alkenyl group(s) and organohydrogenpolysiloxane having a plurality of SiH groups can be crosslinked through an addition reaction with a platinum catalyst.

Illustrative examples of the platinum catalyst include platinum-based catalysts such as platinic chloride, alcohol solution of platinic chloride, reaction product of platinic chloride and alcohol, reaction product of platinic chloride and an olefin compound, reaction product of platinic chloride and vinyl group-containing siloxane, a platinum-olefin complex, a complex of platinum and vinyl group-containing siloxane; platinum group metal-based catalysts such as a rhodium complex and a ruthenium complex. These catalysts may be used after dissolved or dispersed in alcohol solvent, hydrocarbon solvent, or siloxane solvent.

The amount of platinum catalyst is preferably in a range of 5 to 2,000 ppm, particularly in a range of 10 to 500 ppm on the basis of 100 parts by mass of the resin.

When the addition curable silicone resin is used, an addition reaction inhibitor may be added. This addition reaction inhibitor is added as a quencher to prevent the platinum catalyst from acting in the solvent or under a low temperature circumstance after forming the coating film and before heat curing. Illustrative examples thereof include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, and 1,1,3,3-tetramethyl-1,3-divinyldisiloxane.

The amount of addition reaction inhibitor is preferably in a range of 0 to 10 parts by mass, particularly in a range of 0.05 to 3 parts by mass on the basis of 100 parts by mass of the resin.

Illustrative examples of photo-curing method include a method of adding a photoradical generator to generate radical by light, together with using resin having a (meth)acrylate terminal(s) or an olefin terminal(s) or adding a crosslinking agent with the terminal(s) being (meth)acrylate, olefin, or a thiol group(s); and a method of adding a photo-acid generator to generate acid by light, together with using resin or a crosslinking agent having an oxiran group (s), an oxetan group(s), or a vinyl ether group(s).

Illustrative examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoic acid, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl) phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type. Illustrative examples of the thermal radical generator include 2,2'-azobis(isobutyronitrile), 2,2'-azobis(2,4-dimethylvaleronitrile), 2,2'-azobis(2-methylbutyronitrile), 4,4'-azobis(4-cyanovaleric acid), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dimethyl-2,2'-azobis(2-methylpropionate), and dicumyl peroxide.

Illustrative examples of the photo-acid generator include sulfonium salt, iodonium salt, sulfonyldiazomethane, N-sulfonyloxyimide, and oxime-O-sulfonate type acid generators. Specific examples of the photo-acid generator is described in paragraphs [0122] to [0142] of JP 2008-111103A, together with JP 2009-080474A.

The amount of radical generator or photo-acid generator is preferably in a range of 0.1 to 50 parts by mass on the basis of 100 parts by mass of the resin.

Among them, particularly preferable resin of the component (B) contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit, diorganosiloxane having an alkenyl group, and organohydrogenpolysiloxane having an SiH group.

[Tackifier]

The inventive bio-electrode composition may contain a tackifier in order to have adhesion to a living body. Illustrative examples of such a tackifier include silicone resin, as well as non-crosslinkable siloxane, non-crosslinkable poly(meth)acrylate, and non-crosslinkable polyether.

[Organic Solvent]

The inventive bio-electrode composition may contain organic solvent. Illustrative examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, 3,9-dodecadiyne, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyn, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-4-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate; lactone solvent such as γ-butyrolactone.

The amount of organic solvent is preferably in a range of 10 to 50,000 parts by mass on the basis of 100 parts by mass of the resin.

[Carbon Material]

The inventive bio-electrode composition can contain a carbon material as an electric conductivity improver to further enhance the electric conductivity. The carbon material may be exemplified by carbon black, carbon nanotube, carbon fiber, and the like. The carbon nanotube may be either single layer or multilayer, and the surface may be modified with an organic group(s). The amount of carbon material is preferably in a range of 1 to 50 parts by mass on the basis of 100 parts by mass of the resin.

[Electric Conductivity Improver Other than Carbon Material]

The inventive bio-electrode composition also can contain an electric conductivity improver other than the carbon material. Illustrative examples thereof include particles, fiber, and nanowire of resin coated with noble metal such as gold, silver, and platinum; nanoparticles of gold, silver, and platinum; as well as particles of metal oxide such as indium-tin oxide (ITO), indium-zinc oxide (IZO), tin oxide, and zinc oxide.

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried. It is possible to improve the electric conductivity still more by adding a carbon material, and to manufacture a bio-electrode with particularly high adhesion and stretchability by combining a resin with adhesion and stretchability. Furthermore, it is possible to improve the stretchability and adhesion to skin by additives, and to control the stretchability and adhesion by adjusting the composition of the resin and the thickness of the living body contact layer appropriately.

<Bio-Electrode>

The present invention also provides a bio-electrode comprising an electro-conductive base material and a living body contact layer formed on the electro-conductive base material; wherein the living body contact layer is a cured material of the inventive bio-electrode composition described above.

Hereinafter, the inventive bio-electrode will be specifically described by reference to the FIGS., but the present invention is not limited thereto.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 is a layer in which the ionic polymer (ionic material) 4 and the carbon material 5 are dispersed in the resin 6.

When using the bio-electrode 1 of FIG. 1 like this, electric signals are picked from the living body 7 through the ionic polymer 4 and the carbon material 5 while bringing the living body contact layer 3 (i.e., the layer in which the ionic polymer 4 and the carbon material 5 are dispersed in the resin 6) into contact with the living body 7, and then conducted to a sensor device (not shown) through the electro-conductive base material 2 as shown in FIG. 2. As described above, the inventive bio-electrode is capable of coping with both electric conductivity and biocompatibility by using the ionic polymer (ionic material) described above, improving the electric conductivity further by adding electric conductivity improver such as a carbon material in accordance with needs, and obtaining electric signals from skin stably in high sensitivity because the contact area with skin is kept constant due to the adhesion thereof.

Hereinafter, each component composing the inventive bio-electrode will be more specifically described.

[Electro-Conductive Base Material]

The inventive bio-electrode comprises an electro-conductive base material. This electro-conductive base material is usually connected electrically with a sensor device and so on, and conducts electrical signals picked from a living body through the living body contact layer to the sensor device and so on.

As the electro-conductive base material, any electro-conductive material can be used without being limited to particular ones. However, it is preferable to comprise one or more species selected from gold, silver, silver chloride, platinum, aluminum, magnesium, tin, tungsten, iron, copper, nickel, stainless steel, chromium, titanium, and carbon, for example.

The electro-conductive base material may be a hard electro-conductive substrate, an electro-conductive film having flexibility, a cloth with the surface being coated with electro-conductive paste, or a cloth into which electro-conductive polymer is kneaded without being limited to particular substrates. The electro-conductive base material may be flat, uneven, or mesh-form of woven metal wires, which can be appropriately selected in accordance with the use of the bio-electrode.

[Living Body Contact Layer]

The inventive bio-electrode comprises a living body contact layer formed on the electro-conductive base material. This living body contact layer is a part to be actually in contact with a living body when using the bio-electrode, and has electric conductivity and adhesion. The living body contact layer is a cured material of the inventive bio-electrode composition described above, that is to say, an adherent resin layer containing the (A) the ionic material (salt) and (B) the resin described above, together with additives such as a carbon material in accordance with needs.

The living body contact layer preferably has adhesion in a range of 0.5 N/25 mm or more and 20 N/25 mm or less. The adhesion is commonly measured by the method shown in JIS Z 0237, in which a metal substrate such as a stainless steel (SUS) substrate or a polyethylene terephthalate (PET) substrate can be used as a base material or, alternatively, human skin can be used for measuring. Human skin has lower surface energy compared to metals and various plastics, which energy is as low as that of Teflon (registered trade mark), and is hard to adhere.

The living body contact layer of the bio-electrode preferably has a thickness of 1 μm or more and 5 mm or less, more preferably 2 μm or more and 3 mm or less. As the living body contact layer is thinner, the adhesion lowers, but the flexibility is improved, and the weight decreases to improve the compatibility with skin. The thickness of the living body contact layer can be selected based on the balance of adhesion and texture.

The inventive bio-electrode may be provided with an adherent film separately on the living body contact layer as previous bio-electrodes (e.g., the bio-electrode described in JP 2004-033468A) in order to prevent peeling off of the bio-electrode from a living body during the use. When the adherent film is prepared separately, the adherent film may be formed by using a raw material for the adherent film such as an acrylic type, a urethane type, and a silicone type. Particularly, the silicone type is suitable because of the high transparency of oxygen, which enables breathing through the skin while pasting the same, the high water repellency, which decreases lowering of adhesion due to perspiration, and the low irritation to skin. It is to be noted that the inventive bio-electrode does not necessarily require the adherent film that is prepared separately described above, because peeling off from a living body can be prevented by adding tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to apply the ones described in JP 2004-033468A.

As described above, the inventive bio-electrode is capable of conducting electric signals from skin efficiently to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried, because the living body contact layer is formed from a cured material of the inventive bio-electrode composition described above. It is possible to improve the electric conductivity still more by adding a carbon material, and to manufacture a bio-electrode with higher adhesion and stretchability by combining a resin that has adhesion and stretchability. It is also possible to improve the stretchability and adhesion to skin by additives, and to control the stretchability and adhesion by adjusting the composition of the resin and the thickness of the living body contact layer appropriately. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, comprising: applying the inventive bio-electrode composition described above onto the electro-conductive base material; and curing the bio-electrode composition; thereby forming the living body contact layer.

Incidentally, the electro-conductive base material, the bio-electrode composition, etc. used for the inventive method for manufacturing a bio-electrode may be the same as those described above.

The method for applying the bio-electrode composition onto the electro-conductive base material is not limited to particular ones; and dip coating, spray coating, spin coating, roll coating, flow coating, doctor coating, screen printing, flexographic printing, gravure printing, and inkjet printing are suitable, for example.

The method for curing the resin can be appropriately selected based on a kind of the component (B) used for the bio-electrode composition without being limited to particular methods. For example, the bio-electrode composition is preferably cured by either or both of heat and light. The foregoing bio-electrode composition can also be cured by adding a catalyst to generate acid or base to the bio-electrode composition, which causes a crosslinking reaction.

In case of heating, the temperature is not particularly limited and may be appropriately selected based on a kind of the component (B) used for the bio-electrode composition, but is preferably about 50 to 250° C., for example.

When the heating and light irradiation are combined, it is possible to perform the heating and the light irradiation simultaneously, to perform the heating after the light irradiation, or to perform the light irradiation after the heating. It is also possible to perform air-drying to evaporate solvent before heating the coating film.

As described above, the inventive method for manufacturing a bio-electrode makes it possible to manufacture the inventive bio-electrode easily and at low cost, with the bio-electrode being excellent in electric conductivity and biocompatibility, light in weight, and free from large lowering of the electric conductivity even when it is wetted with water or dried.

EXAMPLE

Hereinafter, the present invention will be specifically described by giving Examples and Comparative Examples, but the present invention is not limited thereto. Incidentally, "Me" represents a methyl group, and "Vi" represents a vinyl group.

Ionic polymers 1 to 10 and Comparative ionic polymers 1 and 2, which were blended to bio-electrode composition solutions as an ionic material (electro-conductive material), were synthesized as follows. Each 30 mass % monomer solution in PGMEA was introduced into a reaction vessel and mixed. The reaction vessel was cooled to −70° C. under a nitrogen atmosphere, and subjected to vacuum degassing and nitrogen blowing, which were repeated for three times. After raising the temperature to room temperature, azobisisobutyronitrile (AIBN) was added thereto as a polymerization initiator in an amount of 0.01 mole per 1 mole of the whole monomers, this was warmed to a temperature of 60° C. and then allowed to react for 15 hours. The composition of obtained polymer was identified by $^1$H-NMR after drying the solvent. The molecular weight (Mw) and the dispersity (Mw/Mn) of obtained polymer were determined by gel permeation chromatography (GPC) using tetrahydrofuran (THF) as a solvent. Thus synthesized Ionic polymers 1 to 10 and Comparative ionic polymers 1 to 2 are shown below.

Ionic Polymer 1
Mw=36,400
Mw/Mn=2.11
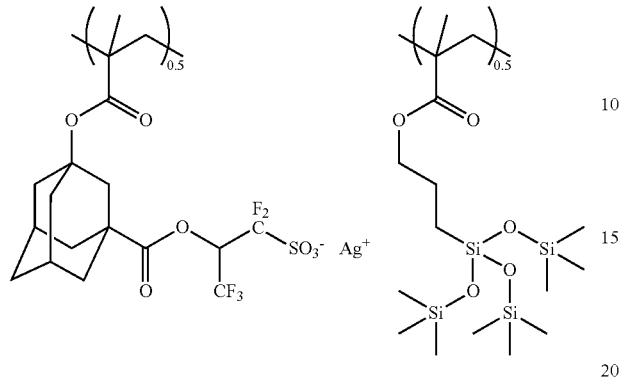
Ionic Polymer 2
Mw=21,700
Mw/Mn=1.91
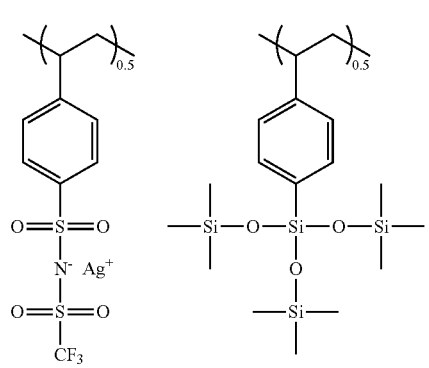
Ionic Polymer 3
Mw=46,700
Mw/Mn=1.84
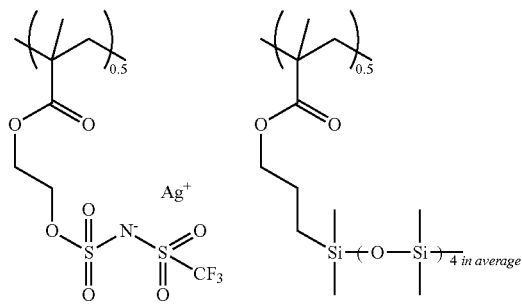
The repeating number in the formula shows the average value.
Ionic Polymer 4
Mw=29,600
Mw/Mn=1.88
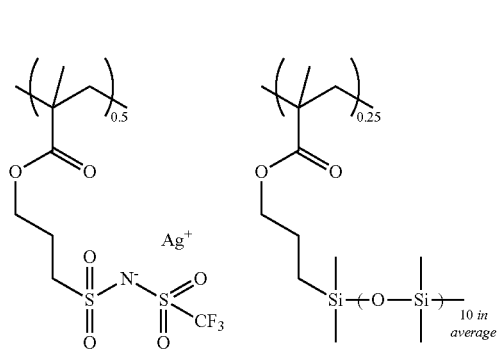
The repeating number in the formula shows the average value.
Ionic Polymer 5
Mw=78,100
Mw/Mn=4.1
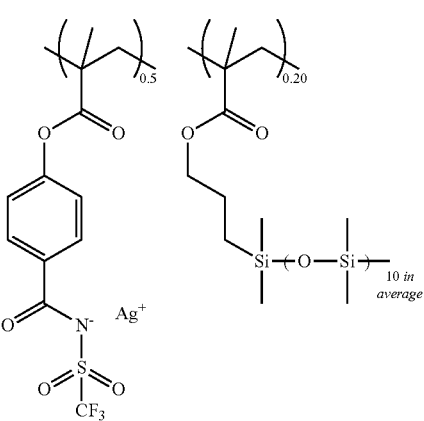

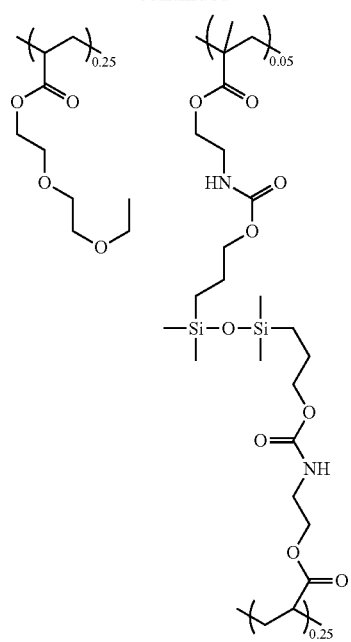
The repeating number in the formula shows the average value.
Ionic polymer 6
Mw=25,100
Mw/Mn=1.86
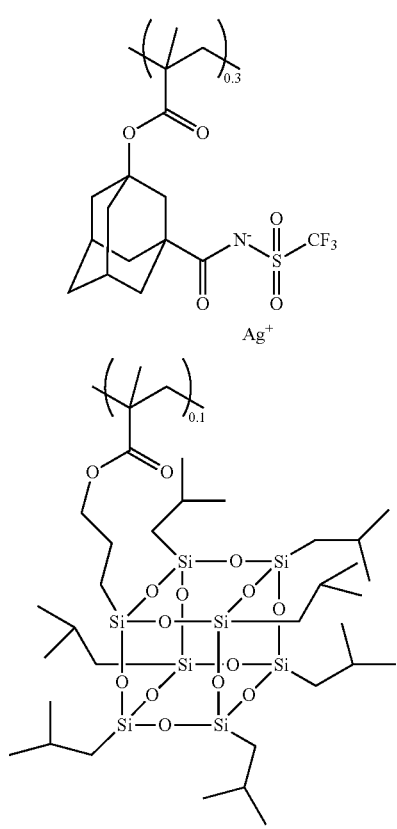
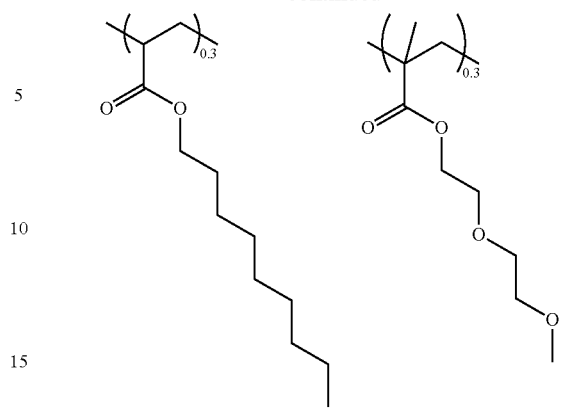
Ionic Polymer 7
Mw=56,300
Mw/Mn=2.10
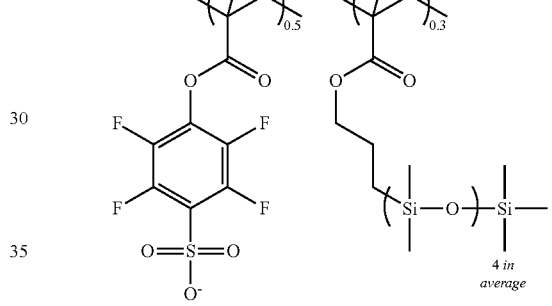
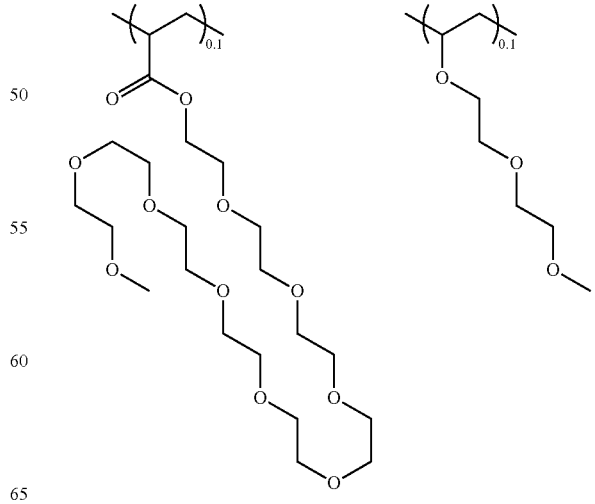

Ionic Polymer 8
Mw=43,300
Mw/Mn=1.98
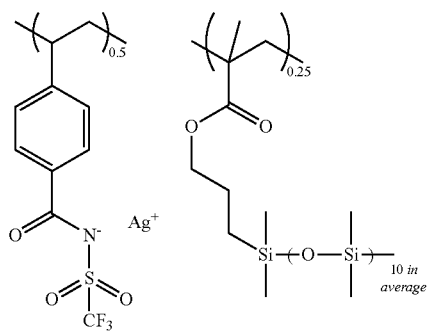
Ionic Polymer 9
Mw=67,800
Mw/Mn=2.05
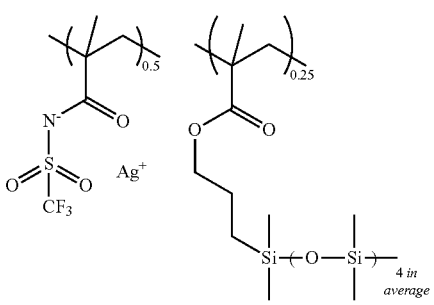
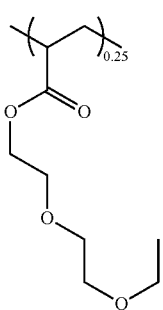
Ionic Polymer 10
Mw=78,300
Mw/Mn=2.11
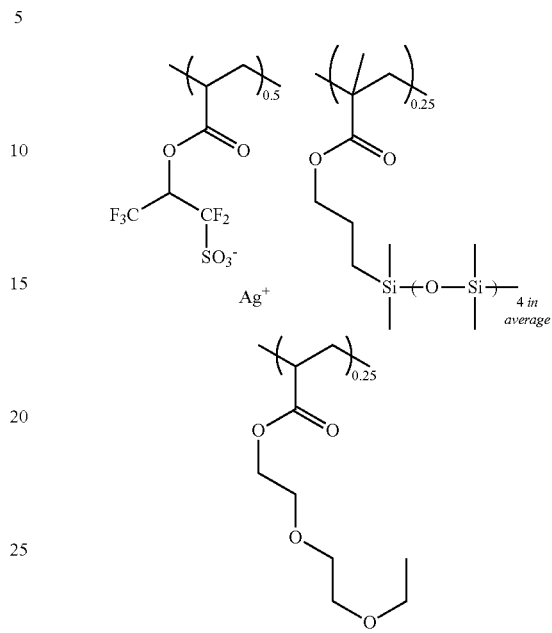
Comparative salts 1 to 4, which were blended as an ionic material to the bio-electrode composition solutions of Comparative Examples, are shown below.
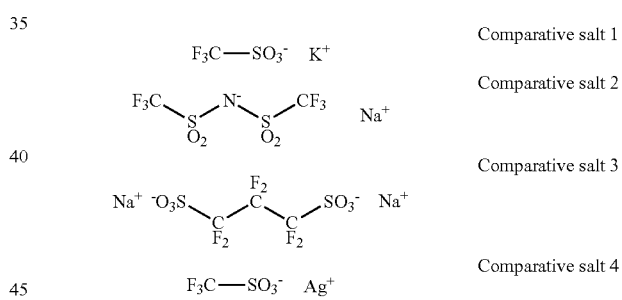
Comparative Polymer 1
Mw=116,000, Mw/Mn=2.20
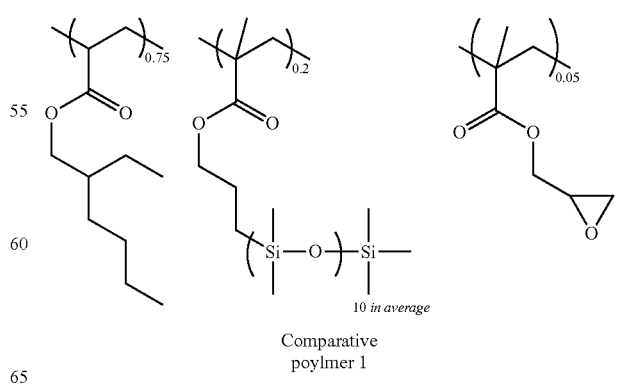
Comparative poylmer 1

Comparative Ionic Polymer 1
  Mw=44,900
  Mw/Mn=2.59

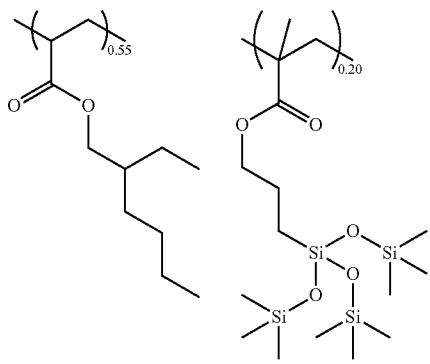

Comparative Ionic Polymer 2
  Mw=57,900
  Mw/Mn=1.89

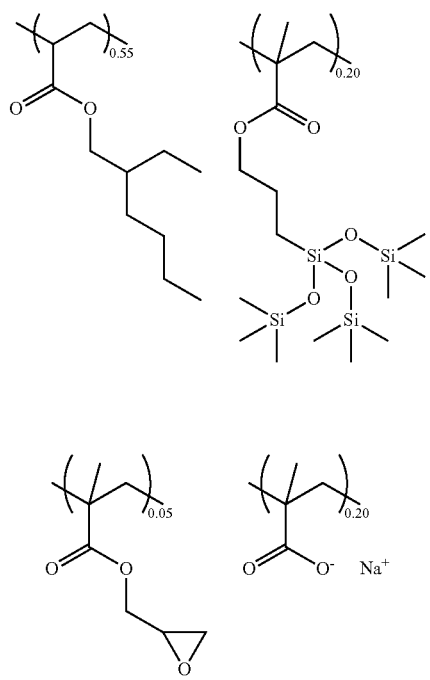

Siloxane compounds 1 to 4, which were blended to the bio-electrode composition solutions as a silicone base resin, are shown below.

(Siloxane Compound 1)

Siloxane compound 1 was vinyl group-containing polydimethylsiloxane having an alkenyl group-content of 0.007 mol/100 g in which the terminals of molecular chain were blocked with $SiMe_2Vi$ groups, with the 30% toluene solution having a viscosity of 27,000 mPa·s.

(Siloxane Compound 2)

Siloxane compound 2 was a 60% toluene solution of polysiloxane of MQ resin composed of an $Me_3SiO_{0.5}$ unit and an $SiO_2$ unit ($Me_3SiO_{0.5}$ unit/$SiO_2$ unit=0.8).

(Siloxane Compound 3)

Siloxane compound 3 was a polydimethylsiloxane-bonded MQ resin obtained by heating a solution composed of 40 parts by mass of vinyl group-containing polydimethylsiloxane having an alkenyl group-content of 0.007 mol/100 g in which the terminals of molecular chain were blocked with OH groups, with the 30% toluene solution having a viscosity of 42,000 mPa·s; 100 parts by mass of 60% toluene solution of polysiloxane of MQ resin composed of an $Me_3SiO_{0.5}$ unit and an $SiO_2$ unit ($Me_3SiO_{0.5}$ unit/$SiO_2$ unit=0.8); and 26.7 parts by mass of toluene with refluxing for 4 hours, followed by cooling.

(Siloxane Compound 4)

As methylhydrogensilicone oil, KF-99 manufactured by Shin-Etsu Chemical Co., Ltd. was used.

As a silicone base resin, KF-353 manufactured by Shin-Etsu Chemical Co., Ltd. was used, which is polyether type silicone oil with the side chain being modified with polyether.

Acrylic polymer blended as an acrylic base polymer to the bio-electrode composition solution is shown below.

Acrylic polymer 1
  Mw=108,000
  Mw/Mn=2.32

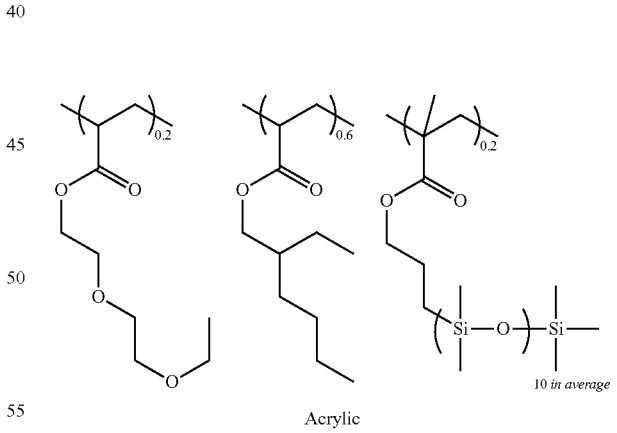

Acrylic polymer 1

The repeating number in the formula shows the average value.

Silicone-urethane acrylates 1 and 2, which were each blended to the bio-electrode composition solutions as a silicone base, acrylic base, or urethane base resin, are shown below.

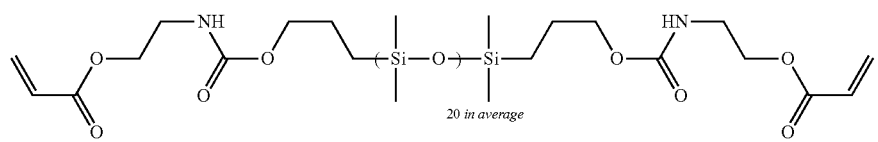

Silicone-urethane acrylate 1

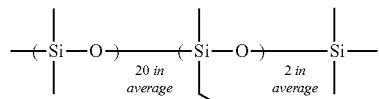

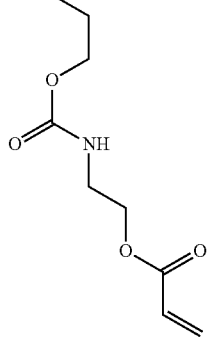

Silicone-urethane acrylate 2

The repeating number in the formula shows the average value.

Organic solvents, which were blended to the bio-electrode composition solutions, are shown below.

PGMEA: propylene glycol-1-monomethyl ether-2-acetate

PGME: propylene glycol-1-monomethyl ether

PGEE: propylene glycol-1-monoethyl ether

The following are a radical generator, a platinum catalyst, and electric conductivity improvers (carbon black, carbon nanotube, Au-coated particle, Ag-coated particle, and ITO particle) blended to the bio-electrode composition solution as an additive.

Radical generator: V-601 manufactured by Wako Pure Chemical Industries, Ltd.

Platinum catalyst: CAT-PL-50T manufactured by Shin-Etsu Chemical Co., Ltd.

Carbon black: DENKA BLACK HS-100 manufactured by Denka Co., Ltd.

Multilayer carbon nanotube: manufactured by Sigma-Aldrich Co. LLC., with the diameter of 110 to 170 nm and the length of 5 to 9 μm Au-coated particle: Micropearl AU (the diameter of 100 μm) manufactured by SEKISUI CHEMICAL CO. LTD.

Ag-coated particle: Ag-coated powder (the diameter of 30 μm) manufactured by Mitsubishi Materials Electronic Chemicals Co., Ltd.

ITO particle: ITO powder (the diameter of 0.03 μm) manufactured by Mitsubishi Materials Electronic Chemicals Co., Ltd.

Examples 1 to 14, Comparative Examples 1 to 8

On the basis of each composition described in Table 1 and Table 2, the ionic material (salt), the resin, the organic solvent, and the additive (radical generator, platinum catalyst, electric conductivity improver) were blended to prepare each bio-electrode composition solution (Bio-electrode composition solutions 1 to 14, Comparative bio-electrode composition solutions 1 to 8).

TABLE 1

| Bio-electrode composition solution | Ionic material (parts by mass) | Resins (parts by mass) | Organic solvent (parts by mass) | Additives (parts by mass) |
|---|---|---|---|---|
| Bio-electrode composition solution 1 | Ionic polymer 1 (20) | Siloxane compound 1 (40) Siloxane compound 2 (100) Siloxane compound 4 (3) | toluene (30) | CAT-PL-50T (1.5) Carbon black (10) |
| Bio-electrode composition solution 2 | Ionic polymer 2 (20) | Siloxane compound 3 (126) Siloxane compound 4 (3) | heptane (30) PGMEA (14) | CAT-PL-50T (0.7) Carbon black (10) |
| Bio-electrode composition solution 3 | Ionic polymer 3 (22.5) | Siloxane compound 1 (40) Siloxane compound 2 (100) Siloxane compound 4 (3) | toluene (30) PGMEA (14) | CAT-PL-50T (0.7) Carbon black (10) |
| Bio-electrode composition solution 4 | Ionic polymer 4 (20) | Siloxane compound 1 (40) Siloxane compound 2 (100) Siloxane compound 4 (3) | toluene (30) PGMEA (14) | CAT-PL-50T (0.7) Carbon black (10) |

TABLE 1-continued

| Bio-electrode composition solution | Ionic material (parts by mass) | Resins (parts by mass) | Organic solvent (parts by mass) | Additives (parts by mass) |
|---|---|---|---|---|
| Bio-electrode composition solution 5 | Ionic polymer 5 (20) | Siloxane compound 3 (126) Siloxane compound 4 (3) | toluene (44) | CAT-PL-50T (1.0) Carbon black (10) |
| Bio-electrode composition solution 6 | Ionic polymer 6 (20) | Siloxane compound 3 (126) Siloxane compound 4 (3) EF-353 (26) | toluene (30) 2-heptanone (14) | CAT-PL-50T (2.0) Carbon black (10) |
| Bio-electrode composition solution 7 | Ionic polymer 7 (25) | Siloxane compound 3 (126) Siloxane compound 4 (3) | toluene (30) PGME (14) | CAT-PL-50T (1.0) Carbon black (10) |
| Bio-electrode composition solution 8 | Ionic polymer 8 (24) | Siloxane compound 3 (126) Siloxane compound 4 (3) | toluene (30) PGME (14) | CAT-PL-50T (1.5) Carbon black (10) |
| Bio-electrode composition solution 9 | Ionic polymer 8 (24) | Siloxane compound 3 (126) Siloxane compound 4 (3) | toluene (30) PGME (14) | CAT-PL-50T (1.5) Multilayer carbon nanotube (6) |
| Bio-electrode composition solution 10 | Ionic polymer 1 (20) | Acrylic polymer 1 (60) Silicone-urethane acrylate 1 (20) | PGMEA (100) | Radical generator V-601 (4) Ag-coated particle (40) |
| Bio-electrode composition solution 11 | Ionic polymer 1 (20) | Acrylic polymer 1 (55) Silicone-urethane acrylate 1 (25) | PGMEA (100) | Radical generator V-601 (4) Au-coated particle (40) |
| Bio-electrode composition solution 12 | Ionic polymer 1 (20) | Acrylic polymer 1 (60) Silicone-urethane acrylate 2 (20) | PGMEA (100) | Radical generator V-601 (4) ITO particle (40) |
| Bio-electrode composition solution 13 | Ionic polymer 9 (25) | Siloxane compound 3 (126) Siloxane compound 4 (3) | toluene (30) PGEE (14) | CAT-PL-50T (1.0) Carbon black (10) |
| Bio-electrode composition solution 14 | Ionic polymer 10 (25) | Siloxane compound 3 (126) Siloxane compound 4 (3) | toluene (30) PGEE (14) | CAT-PL-50T (1.0) Carbon black (10) |

TABLE 2

| Bio-electrode composition solution | Ionic material (parts by mass) | Resins (parts by mass) | Organic solvent (parts by mass) | Additives (parts by mass) |
|---|---|---|---|---|
| Comparative bio-electrode composition solution 1 | Comparative salt 1 (4.7) | Siloxane compound 3 (126) Siloxane compound 4 (3) | toluene (30) PGME (14) | CAT-PL-50T (1.0) Carbon black (10) |
| Comparative bio-electrode composition solution 2 | Comparative salt 2 (8.2) | Siloxane compound 3 (126) Siloxane compound 4 (3) | toluene (30) PGME (14) | CAT-PL-50T (1.0) Carbon black (10) |
| Comparative bio-electrode composition solution 3 | Comparative salt 3 (8.4) | Siloxane compound 3 (126) Siloxane compound 4 (3) | toluene (30) PGME (14) | CAT-PL-50T (1.0) Carbon black (10) |
| Comparative bio-electrode composition solution 4 | Comparative salt 4 (8.4) | Siloxane compound 3 (126) Siloxane compound 4 (3) | toluene (30) PGME (14) | CAT-PL-50T (1.0) Carbon black (10) |
| Comparative bio-electrode composition solution 5 | — | Siloxane compound 3 (126) Siloxane compound 4 (3) | toluene (30) PGME (14) | CAT-PL-50T (1.0) Carbon black (10) |
| Comparative bio-electrode composition solution 6 | Ionic polymer 1 (100) | — | PGMEA (100) | Carbon black (10) |

TABLE 2-continued

| Bio-electrode composition solution | Ionic material (parts by mass) | Resins (parts by mass) | Organic solvent (parts by mass) | Additives (parts by mass) |
|---|---|---|---|---|
| Comparative bio-electrode composition solution 7 | Comparative ionic polymer 1 (20) | Siloxane compound 3 (126) Siloxane compound 4 (3) | toluene (30) PGME (14) | CAT-PL-50T (1.0) Carbon black (10) |
| Comparative bio-electrode composition solution 8 | Comparative ionic polymer 2 (20) | Siloxane compound 3 (126) Siloxane compound 4 (3) | toluene (30) PGME (14) | CAT-PL-50T (1.0) Carbon black (10) |

(Evaluation of Electric Conductivity)

Each bio-electrode composition solution was applied onto an aluminum disk having a diameter of 3 cm and a thickness of 0.2 mm by using an applicator. This was air-dried at room temperature for 6 hours and then baked at 120° C. for 30 minutes under a nitrogen atmosphere by using an oven to be cured, thereby producing four pieces of bio-electrodes for each bio-electrode composition solution. Thus obtained bio-electrode had the living body contact layer 3 at one side and the aluminum disk 8 at the other side as an electro-conductive base material as shown in FIGS. 3A and 3B. Then, the copper wiring 9 was pasted on the surface of the aluminum disk 8 with self-adhesive tape at the side that had not been coated with the living body contact layer to form a lead-out electrode, which was connected to an impedance measurement apparatus as shown in FIG. 3B. Two pieces of the bio-electrodes 1' were pasted on a human arm at a distance of 15 cm from each other such that the side of each living body contact layer was in contact with the skin of the human arm as shown in FIG. 4. The initial impedance was measured while altering the frequency by using an AC impedance measurement apparatus SI1260 manufactured by Solartron. Then, the remained two pieces of the bio-electrodes were immersed in pure water for 1 hour, and used for measuring the impedance on skin by the same method described above after drying the water. Each impedance at the frequency of 1,000 Hz is shown in Table 3.

(Evaluation of Adhesion)

Each bio-electrode composition solution was applied onto a polyethylene naphthalate (PEN) substrate having a thickness of 100 μm by using an applicator. This was air dried at room temperature for 6 hours, followed by curing through baking at 120° C. for 30 minutes under a nitrogen atmosphere by using an oven to produce an adhesive film. From this adhesive film, a tape with a width of 25 mm was cut out. This was pressed to a stainless (SUS304) board and allowed to stand at room temperature for 20 hours. Then, the force (N/25 mm) for peeling the tape, which had been produced from the adhesive film, from the stainless board was measured at an angle of 180° and a speed of 300 ram/min by using a tensile tester. The results are shown in Table 3.

(Measurement of Thickness of Living Body Contact Layer)

On each bio-electrode produced in the evaluation test of electric conductivity described above, the thickness of the living body contact layer was measured by using a micrometer. The results are shown in Table 3.

TABLE 3

| Example | Bio-electrode composition solution | Adhesion (N/25 mm) | Thickness of resin (μm) | Initial impedance (Ω) | Impedance after water immersion (Ω) |
|---|---|---|---|---|---|
| Example 1 | Bio-electrode composition solution 1 | 3.3 | 520 | $8.8E^4$ | $8.3E^4$ |
| Example 2 | Bio-electrode composition solution 2 | 3.2 | 550 | $7.8E^4$ | $7.5E^4$ |
| Example 3 | Bio-electrode composition solution 3 | 3.9 | 540 | $7.1E^4$ | $6.9E^4$ |
| Example 4 | Bio-electrode composition solution 4 | 4.1 | 490 | $5.1E^4$ | $5.2E^4$ |
| Example 5 | Bio-electrode composition solution 5 | 4.4 | 610 | $7.1E^4$ | $7.9E^4$ |
| Example 6 | Bio-electrode composition solution 6 | 5.2 | 560 | $8.0E^4$ | $9.1E^4$ |
| Example 7 | Bio-electrode composition solution 7 | 3.1 | 510 | $6.9E^4$ | $6.0E^4$ |
| Example 8 | Bio-electrode composition solution 8 | 3.3 | 610 | $7.5E^4$ | $7.4E^4$ |
| Example 9 | Bio-electrode composition solution 9 | 2.1 | 520 | $3.2E^4$ | $3.9E^4$ |
| Example 10 | Bio-electrode composition solution 10 | 2.9 | 630 | $8.2E^4$ | $8.3E^4$ |
| Example 11 | Bio-electrode composition solution 11 | 3.3 | 680 | $8.4E^4$ | $8.8E^4$ |
| Example 12 | Bio-electrode composition solution 12 | 3.1 | 660 | $7.1E^4$ | $7.6E^4$ |
| Example 13 | Bio-electrode composition solution 13 | 3.0 | 560 | $4.1E^4$ | $4.6E^4$ |

TABLE 3-continued

| Example | Bio-electrode composition solution | Adhesion (N/25 mm) | Thickness of resin (μm) | Initial impedance (Ω) | Impedance after water immersion (Ω) |
|---|---|---|---|---|---|
| Example 14 | Bio-electrode composition solution 14 | 3.2 | 550 | $6.1E^4$ | $6.6E^4$ |
| Comparative Example 1 | Comparative bio-electrode composition solution 1 | 2.3 | 520 | $4.2E^4$ | $5.3E^5$ |
| Comparative Example 2 | Comparative bio-electrode composition solution 2 | 2.2 | 530 | $5.2E^4$ | $7.3E^5$ |
| Comparative Example 3 | Comparative bio-electrode composition solution 3 | 2.6 | 520 | $5.1E^4$ | $8.3E^5$ |
| Comparative Example 4 | Comparative bio-electrode composition solution 4 | 2.6 | 560 | $1.1E^5$ | $1.1E^6$ |
| Comparative Example 5 | Comparative bio-electrode composition solution 5 | 4.6 | 430 | $8.9E^6$ | $8.8E^6$ |
| Comparative Example 6 | Comparative bio-electrode composition solution 6 | 0 | 330 | $5.9E^5$ | $5.8E^5$ |
| Comparative Example 7 | Comparative bio-electrode composition solution 7 | 4.1 | 530 | $9.9E^6$ | $9.8E^6$ |
| Comparative Example 8 | Comparative bio-electrode composition solution 8 | 3.8 | 430 | $9.1E^6$ | $8.8E^6$ |

As shown in Table 3, in each of Examples 1 to 14, the living body contact layer of which was formed by using the inventive bio-electrode composition containing the salt (ionic material) having particular structure and resins, the initial impedance was low and did not cause large change after the bio-electrodes were immersed to water and dried. That is, Examples 1 to 14 each gave a bio-electrode that had high initial electric conductivity and did not cause large lowering of the electric conductivity even when it is wetted with water or dried. These bio-electrodes of Examples 1 to 14 had good adhesion similar to that of bio-electrode of Comparative Examples 1 to 5, 7, and 8, in which previous salt and resin were blended.

On the other hand, in each Comparative Examples 1 to 4, the living body contact layer of which was formed by using a bio-electrode composition containing previous salt and resins, the initial impedance was relatively low, but large increase of the impedance occurred such that the order of magnitude was changed after water immersion and drying. That is, each of Comparative Examples 1 to 4 only gave a bio-electrode, the electric conductivity of which was largely decreased when it was wetted by water and dried, although the initial electric conductivity was high.

Comparative Example 5, in which the living body contact layer was formed by using a bio-electrode composition that contained resins without containing salt, did not cause large increase of impedance by an order of magnitude after it was immersed to water and dried because it did not contain salt, but the initial impedance was high. That is, Comparative Example 5 only gave a bio-electrode with low initial electric conductivity.

Comparative Example 6, in which the living body contact layer was formed by using a bio-electrode composition that contained salt without containing a resin, did not cause large increase of impedance by an order of magnitude after it was immersed to water and dried because it contained the same salt as in Examples, but completely lacked adhesion since it did not contain an adherent resin, making the impedance with skin (initial impedance) high. That is, Comparative Example 6 only gave a bio-electrode with low initial electric conductivity.

In Comparative Examples 7 and 8, each containing an ion polymer without the repeating unit of the present invention, the adhesion was high, but the initial electric conductivity was low.

As described above, it was revealed that the bio-electrode, with the living body contact layer being formed by using the inventive bio-electrode composition, was excellent in electric conductivity, biocompatibility, and adhesion to an electro-conductive base material; excellent in holding the ionic material to prevent large lowering of electric conductivity even when it was wetted with water or dried; light in weight; and manufacturable at low cost.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A bio-electrode composition comprising:
(A) an ionic material; and
(B) a resin other than the component (A);
the component (A) comprising both of
  a repeating unit-a having a structure of a silver salt selected from the group consisting of silver salts of fluorosulfonic acid, fluorosulfonimide, and fluorosulfonamide; and
  a repeating unit-b having silicon and shown by the following general formula (3) as the repeating unit-b:

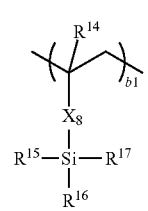

(3)

wherein $R^{14}$ represents a hydrogen atom or a methyl group; $X_8$ represents a —C(=O)—O—$R^{18}$— group, or a —C(=O)—NH—$R^{18}$— group; $R^{18}$ represents any of a single bond, a linear, branched, or cyclic alkylene group having 2 to 12 carbon atoms, or a phenylene group, optionally having one or more groups selected from an ether group, a carbonyl group, an ester group, and an amide group; $R^{15}$, $R^{16}$, and $R^{17}$ each represent a linear, branched, or cyclic alkyl group having 1 to 21 carbon atoms or an aryl group having 6 to 10 carbon atoms, optionally having one or more species selected from a siloxane bond, a silicon atom, and a halogen atom; $R^{15}$ and $R^{16}$, or $R^{15}$, $R^{16}$, and $R^{17}$ are optionally bonded to each other to form a ring or a three dimensional structure; and b1 is a number satisfying $0<b1<1.0$.

2. The bio-electrode composition according to claim 1, wherein the repeating unit-a has one or more structures selected from the structures shown by the following general formulae (1)-1 to (1)-4,

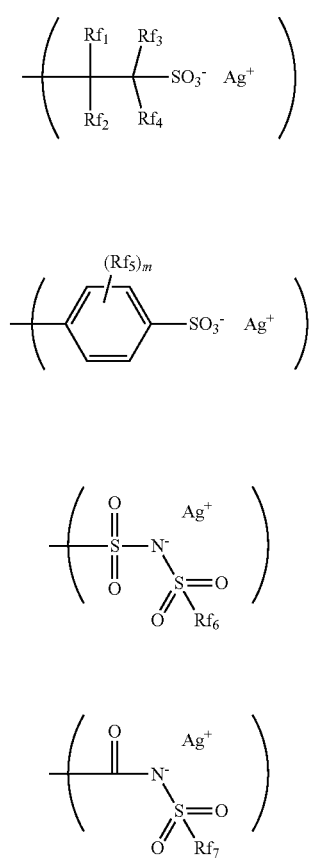

wherein $R_{f1}$ and $R_{f2}$ each represent a hydrogen atom, a methyl group, a fluorine atom, a trifluoromethyl group, or an oxygen atom, provided that when $R_{f1}$ represents the oxygen atom, $R_{f2}$ also represents the oxygen atom to form a carbonyl group together with a carbon atom bonded therewith; $R_{f3}$ and $R_{f4}$ each represent a hydrogen atom, a fluorine atom, or a trifluoromethyl group, provided that one or more fluorine atoms are contained among the total number of atoms in $R_{f1}$ to $R_{f4}$; $R_{f5}$, $R_{f6}$, and $R_{f7}$ each represent a fluorine atom, or a linear or branched alkyl group having 1 to 4 carbon atoms, provided that one or more fluorine atoms are contained; and "m" is an integer of 1 to 4.

3. The bio-electrode composition according to claim 1, wherein the component (A) contains one or more repeating units selected from repeating units a1 to a7 shown by the following general formulae (2) as the repeating unit-a,

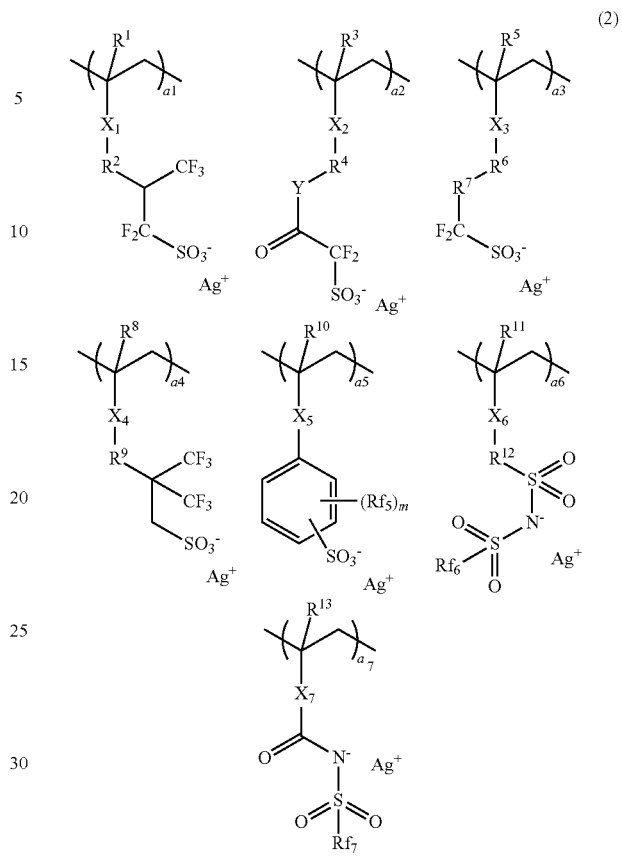

wherein $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 13 carbon atoms, optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $X_1$, $X_2$, $X_3$, $X_4$, and $X_6$ each independently represent any of a single bond, a phenylene group, a naphthylene group, an ether group, an ester group, or an amide group; $X_5$ represents any of a single bond, an ether group, or an ester group; $X_7$ represents a single bond, an arylene group having 6 to 12 carbon atoms, or —C(=O)—O—$X_{10}$—; and $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; Y represents an oxygen atom or an —$NR^{19}$— group, optionally bonded to $R^4$ to form a ring; $R^{19}$ represents a hydrogen atom, or a linear or branched alkyl group having 1 to 4 carbon atoms; $R_{f5}$, $R_{f6}$, and $R_{f7}$ each represent a fluorine atom or a linear or branched alkyl group having 1 to 4 carbon atoms, and at least one fluorine atom is contained in $R_{f5}$, $R_{f6}$, and $R_{f7}$; "m" is an integer of 1 to 4; a1, a2, a3, a4, a5, a6, and a7 are numbers satisfying $0 \leq a1<1.0$, $0 \leq a2<1.0$, $0 \leq a3<1.0$, $0 \leq a4<1.0$, $0 \leq a5<1.0$, $0 \leq a6<1.0$, $0 \leq a7<1.0$, and $0<a1+a2+a3+a4+a5+a6+a7<1.0$.

4. The bio-electrode composition according to claim 2, wherein the component (A) contains one or more repeating units selected from repeating units a1 to a7 shown by the following general formulae (2) as the repeating unit-a,

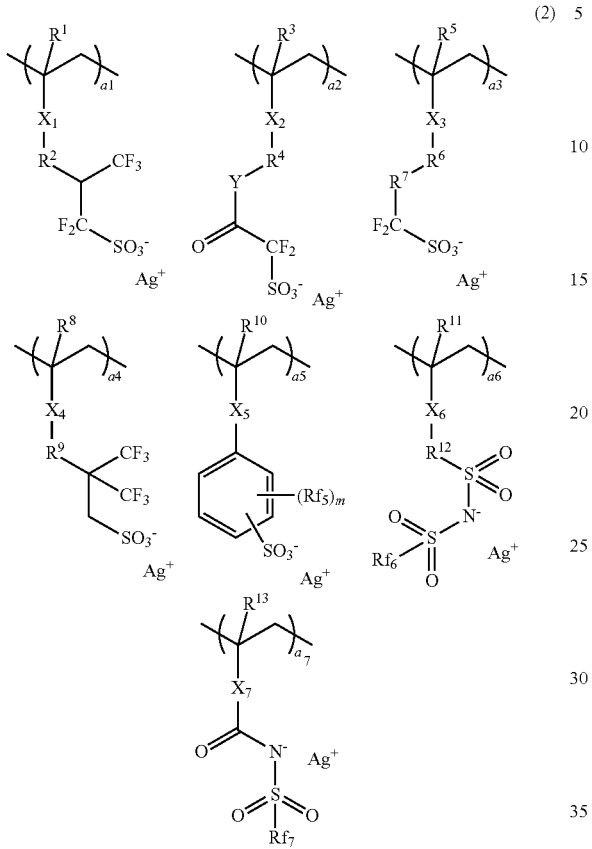

(2)

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 13 carbon atoms, optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $X_1$, $X_2$, $X_3$, $X_4$, and $X_6$ each independently represent any of a single bond, a phenylene group, a naphthylene group, an ether group, an ester group, or an amide group; $X_5$ represents any of a single bond, an ether group, or an ester group; $X_7$ represents a single bond, an arylene group having 6 to 12 carbon atoms, or —C(=O)—O—$X_{10}$—; and $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; Y represents an oxygen atom or an —$NR^{19}$— group, optionally bonded to $R^4$ to form a ring; $R^{19}$ represents a hydrogen atom, or a linear or branched alkyl group having 1 to 4 carbon atoms; $R_{f5}$, $R_{f6}$, and $R_{f7}$ each represent a fluorine atom or a linear or branched alkyl group having 1 to 4 carbon atoms, and at least one fluorine atom is contained in $R_{f5}$, $R_{f6}$, and $R_{f7}$; "m" is an integer of 1 to 4; a1, a2, a3, a4, a5, a6, and a7 are numbers satisfying $0 \leq a1 < 1.0$, $0 \leq a2 < 1.0$, $0 \leq a3 < 1.0$, $0 \leq a4 < 1.0$, $0 \leq a5 < 1.0$, $0 \leq a6 < 1.0$, $0 \leq a7 < 1.0$, and $0 < a1+a2+a3+a4+a5+a6+a7 < 1.0$.

5. The bio-electrode composition according to claim 1, wherein the component (A) contains a repeating unit-c shown by the following general formula (4) in addition to the repeating unit-a and the repeating unit-b,

(4)

wherein $R^{20}$ represents a hydrogen atom or a methyl group; $X_9$ represents any of a single bond, a phenylene group, a naphthylene group, an ether group, an ester group, a phenylene group having an ester group, or an amide group; $R^{21}$ represents a linear, branched, or cyclic alkyl group having 1 to 40 carbon atoms, a linear, branched, or cyclic alkenyl group having 2 to 40 carbon atoms, a linear, branched, or cyclic alkynyl group having 2 to 40 carbon atoms, or an aryl group having 6 to 20 carbon atoms, optionally having an ether group, an ester group, or a hydroxy group; and "c" is a number satisfying $0 < c < 1.0$.

6. The bio-electrode composition according to claim 2, wherein the component (A) contains a repeating unit-c shown by the following general formula (4) in addition to the repeating unit-a and the repeating unit-b,

(4)

wherein $R^{20}$ represents a hydrogen atom or a methyl group; $X_9$ represents any of a single bond, a phenylene group, a naphthylene group, an ether group, an ester group, a phenylene group having an ester group, or an amide group; $R^{21}$ represents a linear, branched, or cyclic alkyl group having 1 to 40 carbon atoms, a linear, branched, or cyclic alkenyl group having 2 to 40 carbon atoms, a linear, branched, or cyclic alkynyl group having 2 to 40 carbon atoms, or an aryl group having 6 to 20 carbon atoms, optionally having an ether group, an ester group, or a hydroxy group; and "c" is a number satisfying $0 < c < 1.0$.

7. The bio-electrode composition according to claim 3, wherein the component (A) contains a repeating unit-c shown by the following general formula (4) in addition to the repeating unit-a and the repeating unit-b,

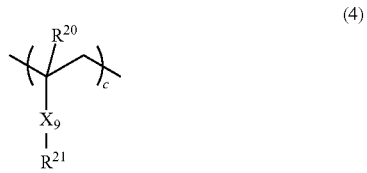

(4)

wherein $R^{20}$ represents a hydrogen atom or a methyl group; $X_9$ represents any of a single bond, a phenylene group, a naphthylene group, an ether group, an ester group, a phenylene group having an ester group, or an amide group; $R^{21}$ represents a linear, branched, or cyclic alkyl group having 1 to 40 carbon atoms, a linear, branched, or cyclic alkenyl group having 2 to 40 carbon atoms, a linear, branched, or cyclic alkynyl group having 2 to 40 carbon atoms, or an aryl group having 6 to 20 carbon atoms, optionally having an ether group, an ester group, or a hydroxy group; and "c" is a number satisfying 0<c<1.0.

8. The bio-electrode composition according to claim 4, wherein the component (A) contains a repeating unit-c shown by the following general formula (4) in addition to the repeating unit-a and the repeating unit-b,

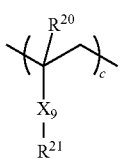
(4)

wherein $R^{20}$ represents a hydrogen atom or a methyl group; $X_9$ represents any of a single bond, a phenylene group, a naphthylene group, an ether group, an ester group, a phenylene group having an ester group, or an amide group; $R^{21}$ represents a linear, branched, or cyclic alkyl group having 1 to 40 carbon atoms, a linear, branched, or cyclic alkenyl group having 2 to 40 carbon atoms, a linear, branched, or cyclic alkynyl group having 2 to 40 carbon atoms, or an aryl group having 6 to 20 carbon atoms, optionally having an ether group, an ester group, or a hydroxy group; and "c" is a number satisfying 0<c<1.0.

9. The bio-electrode composition according to claim 1, wherein the component (B) contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit, diorganosiloxane having an alkenyl group, and organohydrogenpolysiloxane having an SiH group.

10. The bio-electrode composition according to claim 2, wherein the component (B) contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit, diorganosiloxane having an alkenyl group, and organohydrogenpolysiloxane having an SiH group.

11. The bio-electrode composition according to claim 3, wherein the component (B) contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit, diorganosiloxane having an alkenyl group, and organohydrogenpolysiloxane having an SiH group.

12. The bio-electrode composition according to claim 4, wherein the component (B) contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit, diorganosiloxane having an alkenyl group, and organohydrogenpolysiloxane having an SiH group.

13. The bio-electrode composition according to claim 1, further comprising an organic solvent.

14. The bio-electrode composition according to claim 2, further comprising an organic solvent.

15. The bio-electrode composition according to claim 1, further comprising a carbon material.

16. The bio-electrode composition according to claim 15, wherein the carbon material is either or both of carbon black and carbon nanotube.

17. A bio-electrode comprising an electro-conductive base material and a living body contact layer formed on the electro-conductive base material;
wherein the living body contact layer is a cured material of the bio-electrode composition according to claim 1.

18. The bio-electrode according to claim 17, wherein the electro-conductive base material comprises one or more species selected from gold, silver, silver chloride, platinum, aluminum, magnesium, tin, tungsten, iron, copper, nickel, stainless steel, chromium, titanium, and carbon.

19. A method for manufacturing a bio-electrode having an electro-conductive base material and a living body contact layer formed on the electro-conductive base material, comprising:
applying the bio-electrode composition according to claim 1 onto the electro-conductive base material; and curing the bio-electrode composition; thereby forming the living body contact layer.

20. The method for manufacturing a bio-electrode according to claim 19, wherein the electro-conductive base material comprises one or more species selected from gold, silver, silver chloride, platinum, aluminum, magnesium, tin, tungsten, iron, copper, nickel, stainless steel, chromium, titanium, and carbon.

* * * * *